United States Patent
Oestergaard Tange et al.

(10) Patent No.: US 10,190,140 B2
(45) Date of Patent: *Jan. 29, 2019

(54) INCREASED PRODUCTION OF TERPENES AND TERPENOIDS

(71) Applicant: Evolva SA, Reinach (CH)

(72) Inventors: Thomas Oestergaard Tange, Reihen (CH); Michael Naesby, Huningue (FR); Christophe Folly, Basel (CH); Fanny Delegrange, Hagenthal-le-Haut (FR); Jens Houghton-Larsen, Birkerod (DK); Simon Carlsen, Copenhagen (DK)

(73) Assignee: EVOLVA SA, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/665,674

(22) Filed: Aug. 1, 2017

(65) Prior Publication Data

US 2018/0080054 A1 Mar. 22, 2018

Related U.S. Application Data

(62) Division of application No. 14/421,220, filed as application No. PCT/EP2013/067262 on Aug. 19, 2013, now Pat. No. 9,834,800.

(60) Provisional application No. 61/684,422, filed on Aug. 17, 2012, provisional application No. 61/745,164, filed on Dec. 21, 2012.

(51) Int. Cl.
| | |
|---|---|
| *C12N 1/16* | (2006.01) |
| *C12N 9/10* | (2006.01) |
| *C12N 9/88* | (2006.01) |
| *C12P 5/00* | (2006.01) |
| *C12P 5/02* | (2006.01) |
| *C12P 7/00* | (2006.01) |
| *C12P 7/04* | (2006.01) |
| *C12P 9/00* | (2006.01) |
| *C12N 15/52* | (2006.01) |
| *C12N 15/63* | (2006.01) |
| *C12N 15/81* | (2006.01) |
| *C12P 15/00* | (2006.01) |
| *C12P 17/10* | (2006.01) |
| *C12P 23/00* | (2006.01) |

(52) U.S. Cl.
CPC .......... *C12P 9/00* (2013.01); *C12N 1/16* (2013.01); *C12N 9/1007* (2013.01); *C12N 9/1085* (2013.01); *C12N 9/88* (2013.01); *C12N 15/52* (2013.01); *C12N 15/63* (2013.01); *C12N 15/81* (2013.01); *C12P 5/007* (2013.01); *C12P 5/026* (2013.01); *C12P 7/00* (2013.01); *C12P 7/04* (2013.01); *C12P 15/00* (2013.01); *C12P 17/10* (2013.01); *C12P 23/00* (2013.01); *C12Y 205/01068* (2013.01)

(58) Field of Classification Search
None
See application file for complete search history.

(56) References Cited

U.S. PATENT DOCUMENTS

| | | |
|---|---|---|
| 2013/0164808 A1 | 6/2013 | Mcauliffe et al. |
| 2015/0225754 A1 | 8/2015 | Tange et al. |

FOREIGN PATENT DOCUMENTS

| | | |
|---|---|---|
| EP | 1354955 | 10/2003 |
| IE | 62461 | 2/1995 |
| WO | 2000/001649 | 1/2000 |
| WO | 2011/123567 | 10/2011 |
| WO | 2013/096925 | 6/2013 |

OTHER PUBLICATIONS

Albermann et al., "Strategies for strain improvement in Fusarium fujikuroi: overexpression and localization of key enzymes of the isoprenoid pathway and their impact on gibberellin biosynthesis," Appl Microbiol Biotechnol. 97(7):2979-95 (2013).
Farmer et al., "Improving lycopene production in *Escherichia coli* by engineering metabolic control," Nat Biotechnol. 18(5):533-7 (2000).
Nyati et al. "Negative Feedbacks by Isoprenoids on a Mevalonate Kinase Expressed in the Corpora Allata of Mosquitoes," PLoS One 10(11):e0143107 (2015).
Weinberger, "A model for farnesoid feedback control in the mevalonate pathway," Trends Endocrinol Metab 7(1):1-6 (1996).
Bonitz et al., "Evolutionary relationships of microbial aromatic prenyltransferases," PLoS One 6(11):e27336 (Nov. 2011).
Burg & Espenshade, "Regulation of HMG-CoA reductase in mammals and yeast," Prog Lipid Res. 50(4):403-10 (Oct. 2011).
Chambon et al., "Isolation and properties of yeast mutants affected in farnesyl diphosphate synthetase," Curr Genet. 18(1):41-6 (Jul. 1990).
Chambon et al., "Sterol pathway in yeast. Identification and properties of mutant strains defective in mevalonate diphosphate decarboxylase and farnesyl diphosphate synthetase," Lipids 26(8):633-6 (Aug. 1991).
Chang et al., "Structure of a heterotetrameric geranyl pyrophosphate synthase from mint (*Mentha piperita*) reveals intersubunit regulation," Plant Cell 22(2):454-67 (Feb. 2010).
Degenhardt et al., "Monoterpene and sesquiterpene synthases and the origin of terpene skeletal diversity in plants," Phytochemistry 70(15-16):1621-37 (Oct.-Nov. 2009).
GenBank Accession No. AF513112 (pp. 1-2).
GenBank Accession No. Q8L5K3 (pp. 1-3).
Hedl et al., "Enterococcus faecalis acetoacetyl-coenzyme A thiolase/3-hydroxy-3-methylglutaryl-coenzyme A reductase, a dual-function protein of isopentenyl diphosphate biosynthesis,"J Bacteriol. 184(8):2116-22 (Apr. 2002).
Orlova et al., "The small subunit of snapdragon geranyl diphosphate synthase modifies the chain length specificity of tobacco geranylgeranyl diphosphate synthase in planta," Plant Cell 21(12):4002-17 (Dec. 2009).
Paradise et al., "Redirection of flux through the FPP branch-point in *Saccharomyces cerevisiae* by down-regulating squalene synthase," Biotechnol Bioeng. 100(2):371-8 (Jun. 2008).

(Continued)

Primary Examiner — Iqbal H Chowdhury
(74) Attorney, Agent, or Firm — McDonnell Boehnen Hulbert & Berghoff LLP

(57) ABSTRACT

This invention provides recombinant cells and methods for producing terpenes and terpenoids by increasing production or accumulation or both of isoprenoid precursors thereof.

18 Claims, 10 Drawing Sheets

Specification includes a Sequence Listing.

(56) References Cited

OTHER PUBLICATIONS

Rico et al., "Enhanced production of a plant monoterpene by overexpression of the 3-hydroxy-3-methylglutaryl coenzyme A reductase catalytic domain in *Saccharomyces cerevisiae*," Appl Environ Microbiol. 76(19):6449-54 (Oct. 2010).

Shalgi et al., "A catalog of stability-associated sequence elements in 3' UTRs of yeast mRNAs," Genome Biol. 6(10):R86 (Sep. 2005).

Sutherlin et al., "Enterococcus faecalis 3-hydroxy-3-methylglutaryl coenzyme A synthase, an enzyme of isopentenyl diphosphate biosynthesis," J Bacteriol. 184(15):4065-70 (Aug. 2002).

Thompson et al., "Clustal W: improving the sensitivity of progressive multiple sequence alignment through sequence weighting, position-specific gap penalties and weight matrix choice," Nucleic Acids Res. 22(22):4673-80 (Nov. 1994).

Wang & Dixon, "Heterodimeric geranyl(geranyl)diphosphate synthase from hop (*Humulus lupulus*) and the evolution of monoterpene biosynthesis," Proc Natl Acad Sci USA 106:9914-9 (Jun. 2009).

Yang et al., "Enhancing production of bio-isoprene using hybrid MVA pathway and isoprene synthase in *E. coli*," PLoS One 7(4):e33509 (Apr. 2012).

International Search Report of the International Searching Authority for International Application No. PCT/EP2013/067262, dated Jan. 7, 2014 (pp. 1-6).

Written Opinion of the International Searching Authority for International Application No. PCT/EP2013/067262, dated Jan. 7, 2014 (pp. 1-7).

Ishimoto et al., "Sterol-regulatory-element-binding protein 2 and nuclear factor Y control human farnesyl diphosphate synthase expression and affect cell proliferation in hepatoblastoma cells", Biochem J., 429:247-257 (2010).

Kuranda, "The isoprenoid pathway and transcriptional response to its inhibitors in the yeast *Saccharomyces cerevisiae*", FEMS Yeast Res. 10:14-27 (2010).

Wang et al., "Small interfering RNA locks down the molecular target of alendronate, farnesyl pysophosphate synthase, in osteoclast and osteoblast cultures", Mol. Pharm. 8:1016-1024 (2011).

Jordao et al., "Cloning and characterization of bifuntional enzyme farnesyl diphosphate/geranylgeranyl diphosphate synthase from Plasmodium falciparum", Malaria J., 12:184-189 (2013).

Gibbs et al., "The Potential of farnesyltransferase inhibitors as cancer chemotherapeutics", Annu. Rev. Pharmacol. Toxicol. 37:143-166 (1997).

Coxon et al., "Protein geranylgeranylation is required for osteoclast formation, function, and survival: inhibition by bisphosphonates and GGTI-298", J. Bone Miner. res. 15(8):1467-76 (2000).

Montalvetti et al., "Farnesyl pyrophosphate synthase is an essential enzyme in Trypanosoma brucei", J. Bio. Chem., 278:17075-17083 (2003).

Whisstock et al., "Prediction of protein function from protein sequence and structure", Quarterly Reviews of Biophysics, 36(3):307-340 (2003).

Witkowski et al., "Conversion of beta-ketoacyl synthase to a malonyl decarboxylase by replacement of the active-site cysteine with glutamine", Biochemistry, 38(36):11643-50 (Sep. 1999).

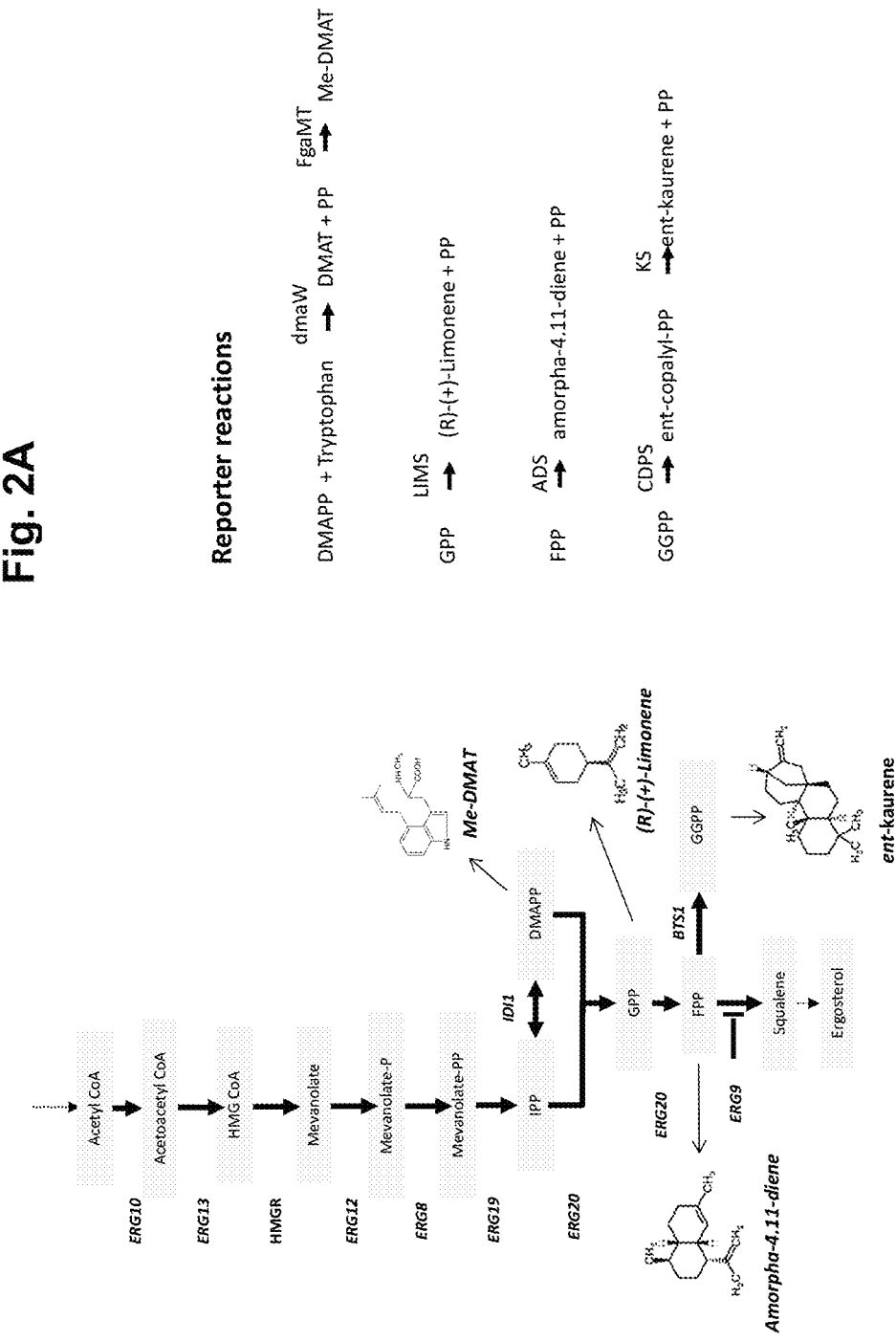

INCREASED PRODUCTION OF TERPENES AND TERPENOIDS

This application is divisional of U.S. Ser. No. 14/421,220, filed Feb. 12, 2015, now U.S. Pat. No. 9,834,800, issued Dec. 5, 2017, which is a U.S. national phase of International Application No. PCT/EP2013/067262 filed Aug. 19, 2013, which claims the benefit of U.S. Provisional Application No. 61/684,422 filed Aug. 17, 2012 and U.S. Provisional Application No. 61/745,164, filed Dec. 21, 2012. The entire disclosure contents of these applications are herewith incorporated by reference in their entirety into the present application.

BACKGROUND OF INVENTION

Field of the Invention

The invention set forth herein relates to genetic engineering and recombinant cells useful in producing terpenes and terpenoids by increasing production or accumulation or both of isoprenoid precursors thereof. The invention provides recombinant cells and methods for using such cells having reduced enzymatic activity for farnesyl diphosphate synthase, geranyl diphosphate synthase or an enzyme having both farnesyl diphosphate synthase and geranyl diphosphate synthase activities, and methods of use thereof. The recombinant cells provided by the invention generally have higher metabolic flux through the mevalonate biochemical pathway, and can also comprise additional recombinant expression constructs encoding enzymes useful for increasing products of the mevalonate pathway, particularly isoprenoids.

Background of the Related Art

Terpenes and the related terpenoids comprise a large class of biologically derived organic molecules. Terpenes and terpenoids are derived from five-carbon isoprene units and are accordingly also referred to as isoprenoids. They are produced from isoprenoid pyrophosphates which are organic molecules that serve as precursors in the biosynthesis of a number of biologically and commercially important molecules.

Terpenoids can be found in all classes of living organisms, and comprises the largest group of natural products. Plant terpenoids are used extensively for their aromatic qualities and play a role in traditional herbal remedies and are under investigation for antibacterial, antineoplastic, and other pharmaceutical functions. Terpenoids contribute to the scent of eucalyptus, the flavors of cinnamon, cloves, and ginger, and the color of yellow flowers. Well-known terpenoids include citral, menthol, camphor, Salvinorin A in the plant *Salvia divinorum*, and cannabinoids.

While the biosynthetic steps leading from isopentenylpyrophosphate (IPP) and/or dimethylallylpyrophosphate (DMAPP) to terpenoids are universal, two different pathways leading to IPP and DMAPP exist—the mevalonic acid pathway and the non-mevalonic, 2-C-methyl-D-erythritol 4-phosphate/1-deoxy-D-xylulose 5-phosphate (MEP/DOXP) pathway. The mevalonate pathway is responsible for the production of isoprenoid-derived molecules in numerous organisms. Many isoprenoid molecules have high commercial value and production of some of these molecules in genetically engineered hosts rather than in the natural host is highly desirable for economical and sustainability reasons.

The part of the mevalonate pathway that generates the basic C5 isoprenoid pyrophosphates, isopentenyl pyrophosphate (IPP) and dimethylallyl pyrophosphate (DMAPP) comprises seven enzymatic steps. The seven *S. cerevisiae* genes involved in these steps are (in consecutive order in the pathway): ERG10, ERG13, HMGR, ERG12, ERG8, ERG19 and IDI1. IPP and DMAPP are the isoprene units that form the basis for synthesis of higher order isoprenoid pyrophosphate precursors containing any number of isoprene units between two and ten. The most important ones are geranyl pyrophosphate (GPP), farnesyl pyrophosphate (FPP) and geranylgeranyl pyrophosphate (GGPP).

SUMMARY OF INVENTION

The present invention comprises methods for increased production of terpenes and terpenoids, advantageously in recombinant cells resulting from increasing production of isoprenoid pyrophosphate precursors. In particular, the invention relates to methods for increasing the production or accumulation or both of isopentenyl pyrophosphate (IPP), dimethylallyl pyrophosphate (DMAPP), geranyl pyrophosphate (GPP), farnesyl pyrophosphate (FPP) and geranylgeranyl pyrophosphate (GGPP) in said recombinant cells.

In one aspect, the invention relates to a method for producing a terpene or terpenoid in a recombinant cell, the method comprising the steps of culturing the cell under conditions wherein the terpene or terpenoid is produced in a genetically engineered cell having reduced expression of endogenous prenyl diphosphate synthase, such as farnesyl diphosphate synthase, geranyl diphosphate synthase or an enzyme having both farnesyl diphosphate synthase and geranyl diphosphate synthase activity, and further comprising one or more recombinant expression constructs encoding heterologous enzymes for producing said terpene or terpenoid.

In an embodiment of the invention, the cell is genetically engineered to reduce expression of farnesyl diphosphate synthase, geranyl diphosphate synthase or an enzyme having both farnesyl diphosphate synthase and geranyl diphosphate synthase activity.

In another embodiment, reduced expression of endogenous farnesyl diphosphate synthase, geranyl diphosphate synthase or an enzyme having both farnesyl diphosphate synthase and geranyl diphosphate synthase activity is produced in the recombinant cell by introducing into the cell a recombinant genetic construct wherein nucleic acid encoding farnesyl diphosphate synthase, geranyl diphosphate synthase or an enzyme having both farnesyl diphosphate synthase and geranyl diphosphate synthase activity is operably linked in the construct to a promoter sequence that directs expression of said farnesyl diphosphate synthase, geranyl diphosphate synthase or an enzyme having both farnesyl diphosphate synthase and geranyl diphosphate synthase activity at levels that are less than the levels of the promoter for the endogenous gene encoding farnesyl diphosphate synthase, geranyl diphosphate synthase or an enzyme having both farnesyl diphosphate synthase and geranyl diphosphate synthase activity.

In a further embodiment, the reduced expression of endogenous farnesyl diphosphate synthase, geranyl diphosphate synthase or an enzyme having both farnesyl diphosphate synthase and geranyl diphosphate synthase activity is produced in the recombinant cell by introducing into the cell a recombinant genetic construct wherein nucleic acid encoding farnesyl diphosphate synthase, geranyl diphosphate synthase or an enzyme having both farnesyl diphosphate synthase and geranyl diphosphate synthase activity is operably linked in the construct to a promoter sequence that directs expression of said farnesyl diphosphate synthase, geranyl diphosphate synthase or an enzyme having both farnesyl diphosphate synthase and geranyl diphosphate synthase activity, wherein between said promoter and nucleic acid sequences encoding farnesyl diphosphate synthase, geranyl diphosphate synthase or an enzyme having both farnesyl diphosphate synthase and geranyl diphosphate synthase activity is a heterologous insert sequence having the formula:

$$-X_1-X_2-X_3-X_4-X_5-$$

wherein $X_2$ comprises at least 4 consecutive nucleotides being complementary to, and forming a hairpin secondary structure element with at least 4 consecutive nucleotides of $X_4$, and
wherein $X_3$ either comprises zero nucleotides or one or more unpaired nucleotides forming a hairpin loop between $X_2$ and $X_4$, and
$X_4$ comprises at least 4 consecutive nucleotides being complementary to, and forming a hairpin secondary structure element with at least 4 consecutive nucleotides of $X_2$; and
wherein $X_1$ and $X_5$ comprises zero, one or more nucleotides.

In certain embodiments, the reduced expression of endogenous farnesyl diphosphate synthase, geranyl diphosphate synthase or an enzyme having both farnesyl diphosphate synthase and geranyl diphosphate synthase activity is produced in the cell by introducing into the cell a recombinant genetic construct wherein nucleic acid farnesyl diphosphate synthase, geranyl diphosphate synthase or an enzyme having both farnesyl diphosphate synthase and geranyl diphosphate synthase activity is operably linked in the construct to a messenger RNA destabilizing motif.

In another embodiment, the invention further or alternatively comprises introducing into the cell a recombinant expression construct encoding a truncated version of 3-hydroxy-3-methyl-glutaryl coenzyme A reductase (HMGR) comprising the catalytically active carboxyl terminal portion thereof. In additional embodiments, the invention further or alternatively comprises introducing into the cell a recombinant expression construct encoding a heterologous nucleic acid sequence encoding a dual function enzyme, wherein said dual function enzyme is an acetoacetyl-CoA thiolase and a HMG-CoA reductase. In a non-limiting example, the dual function enzyme is the mvaE gene encoded by *E. faecalis* or a functional homologue thereof.

In other embodiments, the host cell is a eukaryotic cell or a prokaryotic cell. In an embodiment, the host cell is a eukaryotic cell and is a mammalian cell, a plant cell, a fungal cell or a yeast cell. In a further embodiment, the eukaryotic cell is a yeast cell and the yeast cell is a yeast of species *Saccharomyces cerevisiae, Schizosaccharomyces pombe, Yarrowia lipolytica, Candida glabrata, Candida Hansenula polymorpha, Kluyveromyces lactis, Pichia pastoris, Ashbya gossypii, Arxula adeninivorans, Cyberlindnera jadinii,* or *Candida albicans*. In a particular embodiment, the yeast cell is *Saccharomyces cerevisiae* and the prenyl diphosphate synthase is ERG20, ERG9 or BTS1.

In an embodiment of the invention, the terpene or terpenoid is a monoterpene, a diterpene, a sesquiterpene, a triperpenoid or a tetraterpenoid. Non-limiting embodiments of a monoterpene produced by the methods of the invention are pinene, myrcene or geraniol. Non-limiting embodiments of a diterpene produced by the methods of the invention are geranylgeranyl pyrophosphate, retinol, retinal, phytol, taxol, forskolin or aphidicolin. Non-limiting embodiments of a sesquiterpene produced by the methods of the invention are amorphadiene, patchoulol, santalol, longifolene or thujopsene. Non-limiting embodiments of a triterpenoid produced by the methods of the invention are squalene and the tetraterpenoid is carotenoid.

In a second aspect, the invention relates to a recombinant cell for producing a terpene or terpenoid genetically engineered to have reduced expression of endogenous farnesyl diphosphate synthase, geranyl diphosphate synthase or an enzyme having both farnesyl diphosphate synthase and geranyl diphosphate synthase activity, and further comprising one or more recombinant expression constructs encoding heterologous enzymes for producing said terpene or terpenoid.

In an embodiment of the invention, the reduced expression of endogenous farnesyl diphosphate synthase, geranyl diphosphate synthase or an enzyme having both farnesyl diphosphate synthase and geranyl diphosphate synthase activity is produced in the recombinant cell by introducing into the cell a recombinant genetic construct wherein nucleic acid encoding farnesyl diphosphate synthase, geranyl diphosphate synthase or an enzyme having both farnesyl diphosphate synthase and geranyl diphosphate synthase activity is operably linked in the construct to a promoter sequence that directs expression of said farnesyl diphosphate synthase, geranyl diphosphate synthase or an enzyme having both farnesyl diphosphate synthase and geranyl diphosphate synthase activity at levels that are less than the levels of the promoter for the endogenous gene encoding farnesyl diphosphate synthase, geranyl diphosphate synthase or an enzyme having both farnesyl diphosphate synthase and geranyl diphosphate synthase activity.

In additional embodiments of the invention, the reduced expression of endogenous farnesyl diphosphate synthase, geranyl diphosphate synthase or an enzyme having both farnesyl diphosphate synthase and geranyl diphosphate synthase activity is produced in the recombinant cell by introducing into the cell a recombinant genetic construct wherein nucleic acid encoding farnesyl diphosphate synthase, geranyl diphosphate synthase or an enzyme having both farnesyl diphosphate synthase and geranyl diphosphate synthase activity is operably linked in the construct to a promoter sequence that directs expression of said farnesyl diphosphate synthase, geranyl diphosphate synthase or an enzyme having both farnesyl diphosphate synthase and geranyl diphosphate synthase activity, wherein between said promoter and nucleic acid sequences encoding farnesyl diphosphate synthase, geranyl diphosphate synthase or an enzyme having both farnesyl diphosphate synthase and geranyl diphosphate synthase activity is a heterologous insert sequence having the formula:

$$-X_1-X_2-X_3-X_4-X_5-$$

wherein $X_2$ comprises at least 4 consecutive nucleotides being complementary to, and forming a hairpin secondary structure element with at least 4 consecutive nucleotides of $X_4$, and
wherein $X_3$ either comprises zero nucleotides or one or more unpaired nucleotides forming a hairpin loop between $X_2$ and $X_4$, and
$X_4$ comprises at least 4 consecutive nucleotides being complementary to, and forming a hairpin secondary structure element with at least 4 consecutive nucleotides of $X_2$; and
wherein $X_1$ and $X_5$ comprises zero, one or more nucleotides.

In another embodiment, the reduced expression of endogenous farnesyl diphosphate synthase, geranyl diphosphate synthase or an enzyme having both farnesyl diphosphate synthase and geranyl diphosphate synthase activity is produced in the cell by introducing into the cell a recombinant genetic construct wherein nucleic acid farnesyl diphosphate synthase, geranyl diphosphate synthase or an enzyme having both farnesyl diphosphate synthase and geranyl diphosphate synthase activity is operably linked in the construct to a messenger RNA destabilizing motif.

Further or alternative embodiments of the recombinant cells provided by this invention in addition comprise a recombinant expression construct encoding a truncated version of 3-hydroxy-3-methyl-glutaryl coenzyme A reductase (HMGR) comprising the catalytically active carboxyl terminal portion thereof. In other additional or alternative embodiments, the recombinant cell comprises a recombinant expression construct encoding a heterologous nucleic acid sequence encoding a dual function enzyme, wherein said dual function enzyme is an acetoacetyl-CoA thiolase and a HMG-CoA reductase. In a non-limiting example, the dual function enzyme is the mvaE gene encoded by E. faecalis or a functional homologue thereof.

In certain embodiments, the host cell is a eukaryotic cell or a prokaryotic cell. In particular embodiments, the host cell is a eukaryotic cell that is a mammalian cell, a plant cell, a fungal cell or a yeast cell. In a further embodiment, the eukaryotic cell is a yeast cell and the yeast cell is a yeast of species *Saccharomyces cerevisiae, Schizosaccharomyces pombe, Yarrowia lipolytica, Candida glabrata, Candida Hansenula polymorpha, Kluyveromyces lactis, Pichia pastoris, Ashbya gossypii, Arxula adeninivorans, Cyberlindnera jadinii,* or *Candida albicans*. In an embodiment yeast cell is *Saccharomyces cerevisiae* and the prenyl diphosphate synthase is ERG20, ERG9 or BTS1.

The invention described here relates to recombinant cells genetically engineered to have increased mevalonate production and/or have higher metabolic flux through the mevalonate biochemical pathway, and can also comprise additional recombinant expression constructs encoding enzymes useful for increasing products of the mevalonate pathway, particularly isoprenoids. In some embodiments the genetically engineered recombinant cells express a phenotype of increased mevalonate production or accumulation or both.

Specific preferred embodiments of the present invention will become evident from the following more detailed description of certain preferred embodiments and the claims.

BRIEF DESCRIPTION OF THE DRAWINGS

FIG. 2A shows part of the endogenous mevalonate pathway including the pathway to various alkaloids and terpenoids (left panel). In addition various reactions to yield said alkaloids and terpenoids and the enzymes involved are shown (right panel).

DETAILED DESCRIPTION

Figure 1A:
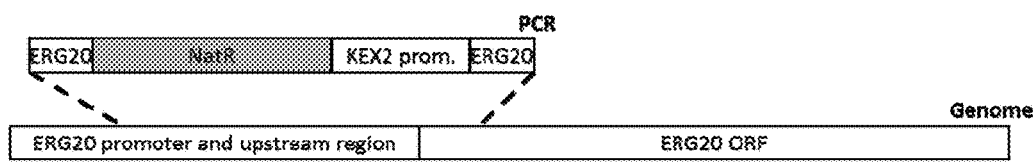
FIG. 1A shows an overview of a construct for homologous recombination useful for inserting the weak KEX2 promoter or (FIG. 1B) the CYC1+SL in front of the ORF encoding farnesyl diphosphate synthase.

All publications, patents and patent applications cited herein are hereby expressly incorporated by reference for all purposes.

Methods well known to those skilled in the art can be used to construct genetic expression constructs and recombinant cells according to this invention. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

Before describing the present invention in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the term "terpenoid" shall be taken to include molecules in which at least part of the molecule is derived from a prenyl pyrophosphate, such as IPP, DMAPP, etc.

It is noted that the terms "pyrophosphate" and "diphosphate" are used interchangeably herein.

Regarding sequence identity between nucleotide and amino acid sequences as set forth herein, and as would be understood by the skilled worker, a high level of sequence identity indicates likelihood that a first sequence is derived from a second sequence. Amino acid sequence identity requires identical amino acid sequences between two aligned sequences. Thus, a candidate sequence sharing 70% amino acid identity with a reference sequence requires that, following alignment, 70% of the amino acids in the candidate sequence are identical to the corresponding amino acids in the reference sequence. Identity according to the present invention is determined by aid of computer analysis, such as, without limitations, the ClustalW computer alignment program (Higgins et al., 1994, Nucleic Acids Res. 22: 4673-4680), and the default parameters suggested therein. The ClustalW software is available from as a ClustalW WWW Service at the European Bioinformatics Institute http://www.ebi.ac.uk/clustalw. Using this program with its default settings, the mature (bioactive) part of a query and a reference polypeptide are aligned. The number of fully conserved residues are counted and divided by the length of the reference polypeptide. The ClustalW algorithm can similarly be used to align nucleotide sequences. Sequence identities can be calculated in a similar way as indicated for amino acid sequences. In certain embodiments, the cell of the present invention comprises a nucleic acid sequence encoding modified, heterologous and additional enzymatic components of terpene and terpenoid biosynthetic pathways, as defined herein.

In one aspect, the invention relates to a method for producing a terpene or terpenoid in a recombinant host cell, the method comprising the steps of culturing under conditions wherein the terpene or terpenoid is produced in a genetically engineered cell having reduced expression of endogenous farnesyl diphosphate synthase, geranyl diphosphate synthase or an enzyme having both farnesyl diphosphate synthase and geranyl diphosphate synthase activity, and further comprising one or more recombinant expression constructs encoding heterologous enzymes for producing said terpene or terpenoid.

The methods of the invention can be used, for example, for large-scale production of a terpene and/or a terpenoid and/or an isoprenoid by a recombinant host cell, as described for the methods of the invention. As shown in the examples that follow, the methods of the invention can be used to produce recombinant host cells with increased metabolic flux through the pathway of interest and efficient production of a terpene and/or a terpenoid and/or an isoprenoid of interest at unexpectedly higher levels in a recombinant host cell.

The increased metabolic flux described herein means at least 2-fold increase in the terpene and/or a terpenoid and/or an isoprenoid of interest flux in a recombinant host cell compared with flux towards a terpene and/or a terpenoid and/or an isoprenoid of interest in a reference host cell.

Downregulation of Farnesyl Diphosphate Synthase and/or Geranyl Diphosphate Synthase In one aspect, the invention relates to host cells having reduced activity or expression of endogenous farnesyl diphosphate synthase and/or geranyl diphosphate synthase or an enzyme having both farnesyl diphosphate synthase and geranyl diphosphate synthase activity. In particular embodiments, when a wild type host cell expresses an enzyme with both farnesyl diphosphate synthase and geranyl diphosphate synthase activity, then the host cells of the invention preferably have reduced activity of said enzyme with both farnesyl diphosphate synthase and geranyl diphosphate synthase activity. A non-limiting example of this is the host cell is *S. cerevisiae* and the endogenous enzyme encoded by the ERG20 gene.

In some embodiments of the invention, the wild type host cells do not express any enzyme with both farnesyl diphosphate synthase and geranyl diphosphate synthase activity. In such an embodiment, the host cells preferably have reduced activity of farnesyl diphosphate synthase and/or geranyl diphosphate synthase.

Said reduced activity results in production or accumulation or both of IPP and DMAPP and thus the host cells of the invention are useful in methods for accumulating and producing IPP, DMAPP as well as compounds having IPP or DMAPP as precursors, and for producing increased amounts of terpenes or terpenoids produced from said isoprenoid precursors.

The farnesyl diphosphate synthase can be any of the farnesyl pyrophosphate synthases described herein. In general the host cell carries an endogenous gene encoding farnesyl diphosphate synthase, where the recombinant cell as provided by the invention has been genetically engineered in order to reduce the activity of farnesyl diphosphate synthase.

The geranyl diphosphate synthase can be any of the geranyl pyrophosphate synthases described herein. In general the recombinant cell as provided by the invention has been genetically engineered in order to reduce the activity of geranyl diphosphate synthase.

Some host cells comprise a geranyl diphosphate synthase which also has some GGPP synthase activity. In embodiments of the invention using such host cells, then the geranyl diphosphate synthase can be an enzyme having both geranyl diphosphate synthase and GGPP synthase activity When the host cell carriers an endogenous gene encoding an enzyme with both farnesyl diphosphate synthase and geranyl diphosphate synthase activity, then the recombinant cell as provided by the invention has been genetically engineered to reduce the activity of said enzyme.

A recombinant cell having reduced activity of farnesyl diphosphate synthase activity according to the invention can have an activity of farnesyl diphosphate synthase, which is about 80%, about 50%, about 30%, for example in the range of 10 to 50% of the activity of farnesyl diphosphate synthase in a similar cell having wild type farnesyl diphosphate synthase activity. It is in general important that the recombinant cell retains at least some farnesyl diphosphate synthase activity, since this is essential for most cells. As shown herein, farnesyl diphosphate synthase activity can be greatly reduced without significantly impairing cell viability. Recombinant cells with greatly reduced farnesyl diphosphate synthase activity can have a somewhat slower growth rate than corresponding wild type cells. Thus it is preferred that recombinant cells of the invention have a growth rate which is at least 50% of the growth of a similar cell having wild type farnesyl diphosphate synthase activity.

In certain embodiments of the invention the host cell having reduced activity of an enzyme with both farnesyl diphosphate synthase and geranyl diphosphate synthase activity according to the invention has an activity of said enzyme, which is at the most 80%, preferably at the most 50%, such as at the most 30%, for example in the range of 10 to 50% of the activity of said enzyme in a similar host cell having a wild type enzyme with both farnesyl diphosphate synthase and geranyl diphosphate synthase activity. It is in general important that recombinant cells retain at least some farnesyl diphosphate synthase and at least some geranyl diphosphate synthase activity, since this is essential for most host cells. As shown herein, both the farnesyl diphosphate synthase and geranyl diphosphate synthase activity can be greatly reduced without significantly impairing cell viability. Recombinant cells with greatly reduced activity can have a somewhat slower growth rate than corresponding wild type cells. Thus it is preferred that the recombinant cells of the invention have a growth rate which is at least 50% of the growth of a similar cell having a wild enzyme with both farnesyl diphosphate synthase and geranyl diphosphate synthase activity.

In other embodiments of the invention, recombinant cells having reduced activity of geranyl diphosphate synthase activity according to the invention has an activity of geranyl diphosphate synthase, which is at the most 80%, preferably at the most 50%, such as at the most 30%, for example in the range of 10 to 50% of the activity of geranyl diphosphate synthase in a similar host cell having a wild type geranyl diphosphate synthase activity. It is in general important that the recombinant cell retains at least some geranyl diphosphate synthase activity, since this is essential for most host cells. As shown herein, geranyl diphosphate synthase activity can be greatly reduced without significantly impairing viability. Recombinant cells with greatly reduced geranyl diphosphate synthase activity can have a somewhat slower growth rate than corresponding wild type cells. However, it is preferred that recombinant cells of the invention have a growth rate which is at least 50% of the growth of a similar host cell having wild type geranyl diphosphate synthase activity.

The activity of farnesyl diphosphate synthase can be reduced in a number of different ways. In certain embodiments, the wild type promoter of a gene encoding farnesyl diphosphate synthase can be exchanged for a weak promoter, such as any of the weak promoters described herein below in the section "Promoter sequence". The endogenous gene can therefore be inactivated by introduction of a construct including a weak promoter, either by homologous recombination or by deletion and insertion. Accordingly, the recombinant cell can comprise an ORF encoding farnesyl diphosphate synthase under the control of a weak promoter, which for example can be any of the weak promoters described in the section "Promoter sequence". In general, cells of the invention only contain one ORF encoding the farnesyl diphosphate synthase endogenous to the host cell, ensuring that the overall level of the endogenous farnesyl diphosphate synthase activity is reduced.

In other embodiments, alternatively or simultaneously, the recombinant cell can comprise a heterologous insert sequence, which reduces the expression of mRNA encoding farnesyl diphosphate synthase. In particular embodiments, the heterologous nucleic acid insert sequence can be positioned between the promoter sequence and the ORF encoding farnesyl diphosphate synthase. Said heterologous insert sequence can be any of the heterologous insert sequences described herein below in the section "Heterologous insert sequence".

In further embodiments, farnesyl diphosphate synthase activity can be reduced using a motif that de-stabilizes mRNA transcripts. Thus, recombinant cells of this invention can comprise a nucleic acid comprising a promoter sequence operably linked to an open reading frame (ORF) encoding farnesyl diphosphate synthase, and a nucleotide sequence comprising a motif that de-stabilizes mRNA transcripts. Said motif can be any of the motif that de-stabilize mRNA transcripts described herein below in the section "Motif that de-stabilize mRNA transcripts".

Similarly, the activity of an enzyme with both farnesyl diphosphate synthase and geranyl diphosphate activity or an enzyme with geranyl diphosphate synthase activity can be reduced using the same or similar methods.

In particular embodiments of the invention, the recombinant cell can also have inactivated and/or no endogenous farnesyl diphosphate synthase activity and/or no endogenous geranyl diphosphate synthase activity. This can for example be accomplished by:
  a) deletion of the entire gene encoding endogenous farnesyl diphosphate synthase; or
  b) deletion of the entire coding region encoding endogenous farnesyl diphosphate synthase; or
  c) deletion of part of the gene encoding farnesyl diphosphate synthase leading to a total loss of endogenous farnesyl diphosphate synthase activity; or
  d) deletion of the entire gene encoding endogenous geranyl diphosphate synthase; or
  e) deletion of the entire coding region encoding endogenous geranyl diphosphate synthase; or
  f) deletion of part of the gene encoding endogenous geranyl diphosphate synthase leading to a total loss of farnesyl diphosphate synthase activity; or
  g) deletion of the entire gene encoding an endogenous enzyme with both farnesyl diphosphate synthase and geranyl diphosphate synthase activity; or
  h) deletion of the entire coding region encoding an endogenous enzyme with both farnesyl diphosphate synthase and geranyl diphosphate synthase activity; or
  i) deletion of part of the gene encoding an endogenous enzyme with both farnesyl diphosphate synthase and geranyl diphosphate synthase activity leading to a total loss of activity of said enzyme.

Farnesyl diphosphate synthase activity and geranyl synthase activity are generally essential for host cells, since FPP and GPP are precursors for essential cellular constituents, e.g. ergosterol. Accordingly, in embodiments of the invention where the host cell or recombinant cell have no endogenous farnesyl diphosphate synthase activity:
  a) cells are cultivated in the presence of ergosterol; or
  b) cells comprise a heterologous nucleic acid encoding an enzyme with farnesyl diphosphate activity.

Similarly, in embodiments of the invention where the host cell or recombinant have no endogenous geranyl diphosphate synthase activity, in advantageous embodiments
  a) cells are cultivated in the presence of ergosterol; or
  b) cells comprise a heterologous nucleic acid encoding an enzyme with geranyl diphosphate and farnesyl diphosphate activity.

In a second aspect, the invention provides recombinant cells for producing a terpene or terpenoid that are genetically engineered to have reduced expression of endogenous farnesyl diphosphate synthase, geranyl diphosphate synthase or an enzyme having both farnesyl diphosphate synthase and geranyl diphosphate synthase activity, and further comprising one or more recombinant expression constructs encoding heterologous enzymes for producing said terpene or terpenoid.

Host and Recombinant Cells

Host and recombinant cells provided herein can be any cell suitable for protein expression (i.e., expression of heterologous genes) including, but not limited to, eukaryotic cells, prokaryotic cells, yeast cells, fungal cells, mammalian cells, plant cells, microbial cells and bacterial cells. Furthermore, cells according to the invention meet one or more of the following criteria: said cells should be able grow rapidly in large fermentors, should produce small organic molecules in an efficient way, should be safe and, in case of pharmaceutical embodiments, should produce and modify the products to be as similar to "human" as possible. Furthermore, a host cell is a cell that can be genetically engineered according to the invention to produce a recombinant cell, which is a cell wherein a nucleic acid has been disabled (by deletion or otherwise), or substituted (for example, by homologous recombination at a genetic locus to change the phenotype of the cell, inter alia, to produce reduced expression of a cellular enzyme or any gene of interest), or a heterologous nucleic acid, inter alia, encoding an enzyme or enzymes to confer a novel or enhanced phenotype on the cell has been introduced.

In further and particular embodiments, recombinant cells are yeast cells that are of yeast species *Saccharomyces cerevisiae, Schizosaccharomyces pombe, Yarrowia lipolytica, Candida glabrata, Ashbya gossypii, Cyberlindnera jadinii, Candida albicans, Arxula adeninivorans, Candida boidinii, Hansenula polymorpha, Kluyveromyces lacti* and *Pichia pastoris*. Yeasts are known in the art to be useful as host cells for genetic engineering and recombinant protein expression. Yeast of different species differ in productivity and with respect to their capabilities to process and modify proteins and to secrete metabolic products thereof. The different 'platforms' of types of yeast make them better suited for different industrial applications. In general, yeasts and fungi are excellent host cells to be used with the present invention. They offer a desired ease of genetic manipulation and rapid growth to high cell densities on inexpensive media. As eukaryotes, they are able to perform protein modifications like glycosylation (addition of sugars), thus producing even complex foreign proteins that are identical or very similar to native products from plant or mammalian sources.

In other embodiments, the host cell for genetic engineering as set forth herein is a microalgal cell such as a cell from *Chlorella* or *Prototheca* species. In other embodiment, the host cell is a cell of a filamentous fungus, for example *Aspergillus* species. In other embodiments, the host cell is a plant cell. In yet additional embodiments, the host cell is a mammalian cell, such as a human, feline, porcine, simian, canine, murine, rat, mouse or rabbit cell. The host cell can also be a CHO, CHO-K1, HEI193T, HEK293, COS, PC12, HiB5, RN33b, BHK cell. In other embodiments, the host cell can be a prokaryotic cell, such as a bacterial cell, including, but not limited to *E. coli* or cells of *Corynebacterium, Bacillus, Pseudomonas* and *Streptomyces* species.

In certain embodiments, the host cell is a cell that, in its nonrecombinant form comprises a gene encoding at least one of the following:
a) farnesyl diphosphate synthase
b) geranyl diphosphate synthase
c) an enzyme having both farnesyl diphosphate synthase and geranyl diphosphate synthase activity In other embodiments, the host cell is a cell that in its nonrecombinant form comprises a gene encoding an enzyme having both farnesyl diphosphate synthase and geranyl diphosphate synthase activity. For example, the host cell can be *S. cerevisiae* that comprises non-recombinant, endogenous ERG20, and which according to this invention can be recombinantly manipulated for reduced expression of the ERG20 gene.

Additional Aspects of Recombinant Cells

In addition to the genetic engineering performed as set forth herein to reduce expression of farnesyl diphosphate synthase, geranyl diphosphate synthase, or an enzyme having both farnesyl diphosphate synthase and geranyl diphosphate synthase activities, the invention provides recombinant cells, in particular embodiments recombinant prokaryotic or eukaryotic cells, having increased levels of mevalonate. In certain embodiments, the invention provides recombinant cells comprising a heterologous nucleic acid sequence encoding a dual function enzyme, wherein the dual function enzyme is an acetoacetyl-CoA thiolase and a HMG-CoA reductase, including, but not limited to, the mvaE gene encoded by *E. faecalis* or a functional homologue thereof. In addition to the heterologous nucleic acid sequence encoding a dual function enzyme, the recombinant cell also can also comprise a heterologous nucleic acid sequence encoding a 3-hydroxy-3-methyl-glutaryl coenzyme A synthase (HMGS), including but not limited to, mvaS gene encoded by *E. faecalis* or a functional homologue thereof.

In yet further embodiments, the invention provides recombinant cells comprising a recombinant expression construct encoding a truncated version of 3-hydroxy-3-methyl-glutaryl coenzyme A reductase (HMGR) comprising the catalytically active carboxyl terminal portion thereof.

Heterologous Insert Sequence

In some embodiments the recombinant cells of the invention comprise a heterologous nucleic acid insert sequence positioned between the promoter sequence and the ORF encoding farnesyl diphosphate synthase, geranyl diphosphate synthase, or an enzyme having both farnesyl diphosphate synthase and geranyl diphosphate synthase activities. In these embodiments of the invention the promoter can be any promoter directing expression of said ORF in the host cell, such as any of the promoters described herein in the section "Promoter sequence". Thus, the promoter can be a weak promoter wherein the promoter activity is less than the promoter activity of the wild type promoter in strength. In a non-limiting example, said weak promoter has decreased promoter activity compared to the ERG20 promoter in *S. cerevisiae*. Thus, in embodiments of the invention wherein the nucleic acid comprises a heterologous nucleic acid insert sequence between the promoter sequence and the ORF encoding farnesyl diphosphate synthase, geranyl diphosphate synthase, or an enzyme having both farnesyl diphosphate synthase and geranyl diphosphate synthase activities, then the promoter sequence can be a promoter directing expression of said ORF in a wild type host cell, e.g. the wild type ERG20 promoter. The heterologous nucleic acid insert sequence can be any nucleic acid sequence that adapts the secondary structure element of a hairpin.

In particular embodiments, the heterologous insert sequence can be a nucleic acid sequence having the general formula (I):

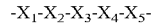

wherein $X_2$ comprises at least 4 consecutive nucleotides being complementary to, and forming a hairpin secondary structure element with at least 4 consecutive nucleotides of $X_4$, and wherein $X_3$ either comprises zero nucleotides or one or more unpaired nucleotides forming a hairpin loop between $X_2$ and $X_4$, and wherein $X_4$ comprises or comprises at least 4 consecutive nucleotides being complementary to, and forming a hairpin secondary structure element with at least 4 consecutive nucleotides of $X_2$, and wherein $X_1$ and $X_5$ comprises zero, one or more nucleotides.

$X_2$ and $X_4$ in general comprises a sequence of nucleotides. Preferably the heterologous nucleic acid insert sequence comprises sections $X_2$ and $X_4$ which are complementary and hybridizes to one another, thereby forming a hairpin. Sections $X_2$ and $X_4$ can be directly connected to each other. In other embodiments $X_2$ and $X_4$ can flank section $X_3$, which forms a loop—the hairpin loop. In general $X_3$ comprises unpaired nucleic acids.

Advantageously, the heterologous insert sequence is long enough to allow a loop to be completed, but short enough to allow a limited translation rate of the ORF following the heterologous insert sequence. In general the longer the stem of the insert stem loop sequence, the lower the translation rate. Thus, in embodiments of the invention, where a very low translation rate of the ORF is desired, then a long heterologous insert sequence should be selected and in particular a heterologous insert sequence with long $X_2$ and $X_4$ sequences complementary to each other should be selected. Thus, in certain embodiments of the present invention the heterologous nucleic acid insert sequence comprises in the range of 10 to 50 nucleotides, preferably in the range of 10 to 30 nucleotides, more preferably in the range of 15 to 25 nucleotides, more preferably in the range of 17 to 23 nucleotides, more preferably in the range of 18 to 22 nucleotides, for example in the range of 18 to 21 nucleotides, such as 19 to 20 nucleotides.

$X_2$ and $X_4$ can individually comprise any suitable number of nucleotides, so long as a consecutive sequence of at least 4 nucleotides of $X_2$ is complementary to a consecutive sequence of at least 4 nucleotides of $X_4$. In a preferred embodiment $X_2$ and $X_4$ comprise the same number of nucleotides. It is preferred that a consecutive sequence of at least 6 nucleotides, more preferably at least 8 nucleotides, even more preferably at least 10 nucleotides, such as in the range of 8 to 20 nucleotides of $X_2$ is complementary to a consecutive sequence of the same amount of nucleotides of $X_4$.

$X_2$ can for example comprise in the range of 4 to 25, such as in the range of 4 to 20, for example of in the range of 4 to 15, such as in the range of 6 to 12, for example in the range of 8 to 12, such as in the range of 9 to 11 nucleotides.

$X_4$ can for example comprise in the range of 4 to 25, such as in the range of 4 to 20, for example of in the range of 4 to 15, such as in the range of 6 to 12, for example in the range of 8 to 12, such as in the range of 9 to 11 nucleotides.

In one preferred embodiment $X_2$ comprises a nucleotide sequence, which is complementary to the nucleotide sequence of $X_4$, i.e., it is preferred that all nucleotides of $X_2$ are complementary to the nucleotide sequence of $X_4$.

In one preferred embodiment $X_4$ comprises a nucleotide sequence, which is complementary to the nucleotide sequence of $X_2$, i.e., it is preferred that all nucleotides of $X_4$ are complementary to the nucleotide sequence of $X_2$. Very preferably, $X_2$ and $X_4$ comprises the same number of nucleotides, wherein $X_2$ is complementary to $X_4$ over the entire length of $X_2$ and $X_4$.

$X_3$ can be absent, i.e., $X_3$ can comprise zero nucleotides. It is also possible that $X_3$ comprises in the range of 1 to 5, such as in the range of 1 to 3 nucleotides. As mentioned above, then it is preferred that X3 does not hybridise with either $X_2$ or $X_4$.

$X_1$ can be absent, i.e., $X_1$ can comprise zero nucleotides. It is also possible that $X_1$ comprises in the range of 1 to 25, such as in the range of 1 to 20, for example in the range of 1 to 15, such as in the range of 1 to 10, for example in the range of 1 to 5, such as in the range of 1 to 3 nucleotides.

$X_5$ can be absent, i.e., $X_5$ can comprise zero nucleotides. It is also possible that $X_5$ can comprise in the range 1 to 5, such as in the range of 1 to 3 nucleotides.

The sequence can be any suitable sequence fulfilling the requirements defined herein above. In one non-limiting example the heterologous insert sequence comprises or comprises SEQ ID NO: 2.

Farnesyl Diphosphate Synthase and Geranyl Diphosphate Synthase

Recombinant cells of the invention in general comprise an open reading frame (ORF) encoding farnesyl diphosphate synthase, geranyl diphosphate synthase, or an enzyme having both farnesyl diphosphate synthase and geranyl diphosphate synthase. Said farnesyl diphosphate synthase, geranyl diphosphate synthase, or an enzyme having both farnesyl diphosphate synthase and geranyl diphosphate synthase can be any farnesyl diphosphate synthase, geranyl diphosphate synthase, or an enzyme having both farnesyl diphosphate synthase and geranyl diphosphate synthase. Frequently it will be a farnesyl diphosphate synthase, geranyl diphosphate synthase, or an enzyme having both farnesyl diphosphate synthase and geranyl diphosphate synthase endogenous to the host cell. Thus, by way of example, in embodiments of the invention wherein the host cell is *S. cerevisiae*, then preferably the ORF encoding farnesyl diphosphate synthase encodes an *S. cerevisiae* farnesyl diphosphate synthase.

The farnesyl diphosphate synthase can be any enzyme, which is capable of catalysing the following chemical reaction:

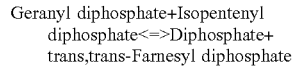
Geranyl diphosphate+Isopentenyl diphosphate<=>Diphosphate+ trans,trans-Farnesyl diphosphate It is preferred that the farnesyl diphosphate synthase according to the present invention is an enzyme categorised under EC 2.5.1.10.

The geranyl diphosphate synthase can be any enzyme, which is capable of catalysing the following chemical reaction:

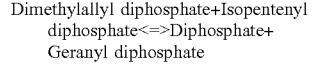
Dimethylallyl diphosphate+Isopentenyl diphosphate<=>Diphosphate+ Geranyl diphosphate It is preferred that the farnesyl diphosphate synthase and/or a geranyl diphosphate synthase according to the present invention is an enzyme categorised under EC 2.5.1.1.

An enzyme having both farnesyl diphosphate synthase and geranyl diphosphate synthase activity is capable of catalysing both of the afore-mentioned reactions is particularly advantageous, and that said enzyme thus is an enzyme categorised under both EC 2.5.1.1 and EC 2.5.1.10.

Farnesyl diphosphate synthase, geranyl diphosphate synthase or an enzyme having both farnesyl diphosphate synthase and geranyl diphosphate synthase activity can be from a variety of sources, such as from bacteria, fungi, plants or mammals. Farnesyl diphosphate synthase, geranyl diphosphate synthase or an enzyme having both farnesyl diphosphate synthase and geranyl diphosphate synthase activity can be wild type embodiments thereof or a functional homologue thereof.

For example, an enzyme having both farnesyl diphosphate synthase and geranyl diphosphate synthase activity can be an enzyme having both farnesyl diphosphate synthase and geranyl diphosphate synthase activity of S. cerevisiae. Thus, said enzyme can be an enzyme of SEQ ID NO:4 or a functional homologue thereof sharing at least 70%, for example at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as at least 99.5%, such as at least 99.6%, such as at least 99.7%, such as at least 99.8%, such as at least 99.9%, such as 100% sequence identity therewith. The sequence identity is preferably calculated as described herein.

A functional homologue of an enzyme having both farnesyl diphosphate synthase and geranyl diphosphate synthase activity is also capable of catalysing one or both of the following chemical reactions:

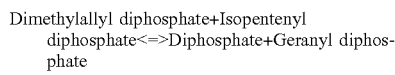

Dimethylallyl diphosphate+Isopentenyl diphosphate<=>Diphosphate+Geranyl diphosphate and/or

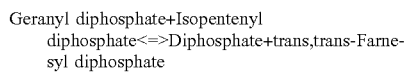

Geranyl diphosphate+Isopentenyl diphosphate<=>Diphosphate+trans,trans-Farnesyl diphosphate Embodiments comprising such a homolog are advantageous as set forth further herein.

Promoter Sequence

In certain embodiments, this invention provides recombinant host cells comprising a nucleic acid comprising a promoter sequence operably linked to an ORF encoding farnesyl diphosphate synthase, geranyl diphosphate synthase, or an enzyme having both farnesyl diphosphate synthase and geranyl diphosphate synthase activities, wherein said ORF preferably is endogenous to said host cell. The invention also relates to recombinant cells comprising a nucleic acid comprising a promoter sequence operably linked to an ORF, wherein said ORF encodes farnesyl diphosphate synthase, geranyl diphosphate synthase, or an enzyme having both farnesyl diphosphate synthase and geranyl diphosphate synthase activities. In these embodiments, a promoter sequence can be any sequence capable of directing expression of said ORF in the particular host cell.

As used herein, the term "promoter" is intended to mean a region of DNA that facilitates transcription of a particular gene. Promoters are generally located in close proximity to the genes they regulate, being encoded on the same strand as the transcribed ORF and typically upstream (towards the 5' region of the sense strand). In order for transcription to take place, the enzyme that synthesizes RNA, known as RNA polymerase, must attach to the DNA 5' to the beginning of the ORF. Promoters contain specific DNA sequences and response elements that provide an initial binding site for RNA polymerase and for proteins called transcription factors that recruit RNA polymerase. These transcription factors have specific activator or repressor sequences of corresponding nucleotides that attach to specific promoters and regulate gene expressions.

The promoter sequence can in general be positioned immediately adjacent to the open reading frame (ORF), or a heterologous nucleic acid insert sequence can be positioned between the promoter sequence and the ORF. Positions in the promoter are in general designated relative to the transcriptional start site, where transcription of RNA begins for a particular gene (i.e., positions upstream are negative numbers counting back from −1, for example −100 is a position 100 base pairs upstream).

The promoter sequence according to the present invention in general comprises at least a core promoter, which is the minimal portion of the promoter required to properly initiate transcription. In addition the promoter sequence can comprise one or more of the following promoter elements:
  transcription start site (TSS)
  a binding site for RNA polymerase
  general transcription factor binding sites
  proximal promoter sequence upstream of the gene that tends to contain primary regulatory elements
  specific transcription factor binding sites
  distal promoter sequence upstream of the gene that can contain additional regulatory elements, often with a weaker influence than the proximal promoter
  binding sites for repressor proteins
  Prokaryotic Promoters In prokaryotes, the promoter comprises two short sequences at −10 and −35 positions upstream from the transcription start site. Sigma factors not only help in enhancing RNA polymerase binding to the promoter, but also help RNAP target specific genes to transcribe. The sequence at −10 is called the Pribnow box, or the −10 element, and usually comprises the six nucleotides TATAAT. The other sequence at −35 (the −35 element) usually comprises the seven nucleotides TTGACAT. Both of the above consensus sequences, while conserved on average, are not found intact in most promoters. On average only 3 of the 6 base pairs in each consensus sequence is found in any given promoter. No naturally occurring promoters have been identified to date having an intact consensus sequences at both the −10 and −35; artificial promoters with complete conservation of the −10/−35 hexamers has been found to promote RNA chain initiation at very high efficiencies.

Some promoters also contain a UP element (consensus sequence 5'-AAAWWTWTTTTNNNAAANNN-3'; W=A or T; N=any base) centered at −50; the presence of the −35 element appears to be unimportant for transcription from the UP element-containing promoters.

Eukaryotic Promoters

Eukaryotic promoters are also typically located upstream of the ORF and can have regulatory elements several kilobases (kb) away from the transcriptional start site. In eukaryotes, the transcriptional complex can cause the DNA to fold back on itself, which allows for placement of regulatory sequences far from the actual site of transcription. Many eukaryotic promoters contain a TATA box (sequence TATAAA), which in turn binds a TATA binding protein which assists in the formation of the RNA polymerase transcriptional complex. The TATA box typically lies very close to the transcriptional start site (often within 50 bases).

Host and recombinant cells of the present invention comprise recombinant expression constructs having a promoter sequence operably linked to a nucleic acid sequence encoding a protein including inter alia, farnesyl diphosphate synthase, geranyl diphosphate synthase, or an enzyme having both farnesyl diphosphate synthase and geranyl diphosphate synthase activities. The promoter sequence is not limiting for the invention and can be any promoter suitable for the host cell of choice.

In certain embodiments of the present invention the promoter is a constitutive or inducible promoter. The promoter sequence can also be a synthetic promoter.

In a further embodiment of the invention, the promoter is, in non-limiting examples, an endogenous promoter, KEX2, PGK-1, GPD1, ADH1, ADH2, PYK1, TPI1, PDC1, TEF1, TEF2, FBA1, GAL1-10, CUP1, MET2, MET14, MET25, CYC1, GAL1-S, GAL1-L, TEF1, ADH1, CAG, CMV, human UbiC, RSV, EF-1 alpha, SV40, Mt1, Tet-On, Tet-Off, Mo-MLV-LTR, Mx1, progesterone, RU486 or Rapamycin-inducible promoter.

In particular embodiments of the invention, the recombinant cell comprises a heterologous insert sequence between the promoter sequence and the ORF encoding farnesyl diphosphate synthase, geranyl diphosphate synthase, or an enzyme having both farnesyl diphosphate synthase and geranyl diphosphate synthase activities. Promoter sequences can comprise a wild type promoter, for example the promoter sequence can be the promoter directing expression of said ORF in a wild type host cell. Thus, the promoter sequence can for example be the wild type ERG20 promoter.

In another embodiment of the invention, the promoter sequence is a weak promoter. In particular, in embodiments of the invention wherein the nucleic acid does not contain a heterologous nucleic acid insert sequence, then the promoter sequence is preferably a weak promoter. A weak promoter according to the present invention is a promoter, which directs a lower level of transcription in the host cell. In particular it is preferred that the promoter sequence directs expression of an ORF encoding farnesyl diphosphate synthase, geranyl diphosphate synthase, or an enzyme having both farnesyl diphosphate synthase and geranyl diphosphate synthase activities at an expression level significantly lower than the expression level obtained with the wild type promoter (e.g., in yeast an ERG20 promoter). Said ORF is preferably an ORF encoding native farnesyl diphosphate synthase, native geranyl diphosphate synthase, or a native enzyme having both farnesyl diphosphate synthase and geranyl diphosphate synthase activities, and accordingly the ORF is preferably endogenous to the host or recombinant cell.

It can be determined whether a promoter sequence is a weak promoter or directs a lower level of transcription in the host cell, by determining the expression level of mRNA encoding farnesyl diphosphate synthase, geranyl diphosphate synthase, or an enzyme having both farnesyl diphosphate synthase and geranyl diphosphate synthase activities in a host cell, comprising an ORF encoding farnesyl diphosphate synthase, geranyl diphosphate synthase, or an enzyme having both farnesyl diphosphate synthase and geranyl diphosphate synthase activities operably linked to the potential weak promoter, and by determining the expression level of mRNA encoding farnesyl diphosphate synthase, geranyl diphosphate synthase, or an enzyme having both farnesyl diphosphate synthase and geranyl diphosphate synthase activities in a second reference cell comprising an ORF encoding farnesyl diphosphate synthase, geranyl diphosphate synthase, or an enzyme having both farnesyl diphosphate synthase and geranyl diphosphate synthase activities operably linked to the wild type ERG20 promoter. The second reference cell can be a wild type cell and preferably the tested recombinant cell is of the same species as the second cell. The expression level of mRNA encoding farnesyl diphosphate synthase, geranyl diphosphate synthase, or an enzyme having both farnesyl diphosphate synthase and geranyl diphosphate synthase activities can be determined using any useful method known to the skilled person such as by quantitative PCR. If the expression level of said mRNA in the host cell comprising the potential weak promoter is significantly lower than in the second reference cell, then the promoter is a weak promoter.

It is preferred that the promoter sequence to be used with the present invention directs expression of the ORF encoding farnesyl diphosphate synthase, geranyl diphosphate synthase, or an enzyme having both farnesyl diphosphate synthase and geranyl diphosphate synthase activities at an expression level, which is at the most 70%, such as at the most 60%, for example at the most 50%, such as at the most 40% of the expression level obtained with the wild type ERG20 promoter. The expression level is preferably determined as described above.

Thus, in certain embodiments it is preferred that the promoter sequence to be used with the present invention, when contained in a host cell and operably linked to an ORF encoding farnesyl diphosphate synthase, geranyl diphosphate synthase, or an enzyme having both farnesyl diphosphate synthase and geranyl diphosphate synthase activities, directs expression of said ORF in said host cell so the level of mRNA encoding farnesyl diphosphate synthase in said host cell is at the most 70%, such as at the most 60%, for example at the most 50%, such as at the most 40%, preferably in the range of 10 to 50% of the level of mRNA encoding farnesyl diphosphate synthase, geranyl diphosphate synthase, or an enzyme having both farnesyl diphosphate synthase and geranyl diphosphate synthase activities present in a second cell containing a wild type ERG20 gene, wherein the host cell and the second cell is of the same species.

Thus, in certain embodiments it is preferred that the heterologous promoter sequence to be used with the present invention, when contained in a host cell and operably linked to an ORF encoding farnesyl diphosphate synthase, geranyl diphosphate synthase, or an enzyme having both farnesyl diphosphate synthase and geranyl diphosphate synthase activities, directs expression of said ORF in said host cell so the level of mRNA encoding farnesyl diphosphate synthase, geranyl diphosphate synthase, or an enzyme having both farnesyl diphosphate synthase and geranyl diphosphate synthase activities in said recombinant cell is at the most 70%, preferably at the most 60%, even more preferably at the most 50%, such as at the most 40%, preferably is in the range of 10 to 50% of the level of mRNA encoding farnesyl diphosphate synthase, geranyl diphosphate synthase, or an enzyme having both farnesyl diphosphate synthase and geranyl diphosphate synthase activities present in a second cell containing a wild type gene encoding farnesyl diphosphate synthase, geranyl diphosphate synthase, or an enzyme having both farnesyl diphosphate synthase and geranyl diphosphate synthase activities, wherein the recombinant cell and the second cell is of the same species.

It can also be determined whether a promoter sequence is a weak promoter or directs a lower level of transcription in the host cell, by determining the expression level of any test protein, including but not limited to a reporter gene (a non-limiting example of a reporter gene is green fluorescent protein, GFP) in a recombinant cell, comprising an ORF encoding said test protein operably linked to the potential weak promoter, and by determining the expression level of the same test protein in a second cell comprising an ORF encoding said test protein operably linked to the wild type ERG20 promoter. The second cell can be a wild type cell and preferably the tested recombinant cell is of the same species as the second cell. The expression level of test protein can be determined using any useful method known to the skilled person. For example the test protein can be a fluorescent protein and the expression level can be assessed by determining the level of fluorescence.

Thus, in a preferred embodiment of the invention the heterologous promoter sequence to be used with the present invention, when contained in a recombinant cell and operably linked to an ORF encoding a test protein, directs expression of said ORF in said recombinant cell so the level of the test protein in said recombinant cell is at the most 70%, such as at the most 60%, for example at the most 50%, such as at the most 40%, preferably in the range of 10 to 50% of the level of the test protein present in a second cell containing an ORF encoding the test protein operably linked to a wild type ERG20 promoter, wherein the host cell and the second cell is of the same species. The test protein is preferably a fluorescent protein, e.g. GFP.

Non-limiting examples of weak promoters useful with the present include the CYC-1 promoter or the KEX-2 promoter; in particular the promoter sequence can be the KEX-2 promoter. Thus in certain embodiments of the invention the heterologous promoter sequence comprises or comprises the KEX-2 promoter.

Thus, in embodiments of the invention where the ORF encodes a farnesyl diphosphate synthase, then preferably said farnesyl diphosphate synthase is a farnesyl diphosphate synthase native to the host or recombinant cell, and the heterologous promoter sequence is a weak promoter directing expression of said native farnesyl diphosphate synthase at a level, which is significantly lower than the native expression level.

In embodiments of the invention where the ORF encodes a geranyl diphosphate synthase, then preferably said geranyl diphosphate synthase is a geranyl diphosphate synthase native to the host or recombinant cell, and the heterologous promoter sequence is a weal promoter directing expression of said native geranyl diphosphate synthase at a level, which is significantly lower than the native expression level.

The term "significantly lower" as used herein preferably means at the most 70%, preferably at the most 60%, even more preferably at the most 50%, such as at the most 40%. In particular the term "significantly lower" can be used to mean in the range of 10 to 50%.

Motifs that De-Stabilize mRNA Transcripts

In certain embodiments the recombinant cells of the invention comprises a nucleic acid comprising a promoter sequence operably linked to an open reading frame (ORF) encoding farnesyl diphosphate synthase, geranyl diphosphate synthase or an enzyme having both farnesyl diphosphate synthase and geranyl diphosphate synthase activity, and a nucleotide sequence comprising a motif that de-stabilizes mRNA transcripts.

In this embodiment the promoter can be any of the promoters described herein in the section "Promoter sequence", for example the promoter can be the wild type ERG20 promoter. Thus, the host cell can comprise the native farnesyl diphosphate gene, geranyl diphosphate synthase gene or a gene encoding an enzyme having both farnesyl diphosphate synthase and geranyl diphosphate synthase activity, which has been further modified to contain, downstream of its ORF, a DNA sequence motif that reduces the half-life of the mRNA produced from this gene, such as a motif that de-stabilize mRNA transcripts. The motif that de-stabilizes mRNA transcripts can be any motif, which when positioned in the 3'-UTR of a mRNA transcript can de-stabilize the mRNA transcript and lead to reduced half-life of the transcript (see e.g. Shalgi et al., 2005 *Genome Biology* 6:R86). Thus, to further reduce the activity of the farnesyl diphosphate synthase, geranyl diphosphate synthase or an enzyme having both farnesyl diphosphate synthase and geranyl diphosphate synthase activity, a nucleotide sequence containing a motif that de-stabilizes mRNA transcripts can be inserted into the native farnesyl diphosphate gene, geranyl diphosphate synthase gene or a gene encoding an enzyme having both farnesyl diphosphate synthase and geranyl diphosphate synthase activity, downstream of the ORF. Examples of such destabilizing sequences in yeast include, but are not limited to the M1 motif consensus sequence of TATATATATATAT (SEQ ID NO: 28) and the M24 motif consensus sequence of TGTATAATA (SEQ ID NO: 29).

Additional Heterologous Nucleic Acid

Recombinant cells of the invention can in addition to the nucleic acid comprising an ORF encoding farnesyl diphosphate synthase and/or a geranyl diphosphate synthase operably linked to a promoter sequence also comprise one of more additional heterologous nucleic acids. In alternative embodiments, said recombinant cells can comprise additional recombinant expression constructs that direct expression in the cell of enzymes, inter alia, for producing terpenes or terpenoids as described herein.

In particular embodiments, said additional heterologous nucleic acid can contain a nucleic acid encoding an enzyme useful in the biosynthesis of a compound, which is desirable to synthesize from mevalonate The heterologous nucleic acid preferably contains a nucleic acid encoding an enzyme useful in the biosynthesis of a compound, which is desirable to synthesize from either IPP or DMAPP or from both IPP and DMAPP. Thus, the additional heterologous nucleic acid can encode an enzyme useful in the biosynthesis of a terpene, a terpenoid or an alkaloid from IPP or DMAPP.

Thus, the additional heterologous nucleic acid can encode any enzyme using IPP or DMAPP as a substrate. Such enzymes can be any enzyme classified under EC 2.5.1.— using IPP or DMAPP as a substrate. Examples of such enzymes include GPP synthases, FPP synthases, GGPP synthases, synthases capable of catalysing incorporation of longer isoprenoid chains (e.g. chains of up to around 10 isoprenoids) and prenyl transferases.

In particular, the additional heterologous nucleic acid can be selected according to the particular isoprenoid compound or terpene or terpenoid to be produced by the recombinant cell. Thus, if the recombinant cell is to be used in the production of a particular isoprenoid compound or terpene or terpenoid, then the cell can comprise one or more additional heterologous nucleic acid sequences encoding one or more enzymes of the biosynthesis pathway of that particular isoprenoid compound or terpene or terpenoid.

Thus, the additional heterologous nucleic acid can in certain embodiments of the invention encode a terpene synthase. In particular, in embodiments of the invention wherein the recombinant cell is to be employed in methods for production of a terpene, then it is preferred that the recombinant cell comprises an additional heterologous nucleic acid encoding a terpene synthase. Said terpene can for example be any of the terpenes described herein below in the section "Terpenoids and terpenes". Examples of useful terpene synthases to be used with the present invention are described in Degenhardt et al., 2009, *Phytochemistry* 70:1621-1637. Thus, the additional heterologous nucleic acid can for example encode any of the terpene synthases described Degenhardt et al., 2009.

In certain embodiments of the invention one additional heterologous nucleic acid can encode a monoterpene synthase. In particular, in embodiments of the invention wherein the host cell is to be employed in methods for production of a monoterpene, then it is preferred that the host cell comprise a heterologous nucleic encoding a monoterpene synthase. Said monoterpene can for example be any of the monoterpenes described herein below in the section "Terpenoids and terpenes". Said monoterpene synthase can be any monoterpene synthase, for example any of the monoterpene synthases described in Table 1 of Degenhardt et al., 2009. Said table also outlines for synthesis of which particular monoterpene each monoterpene synthase is useful.

In certain embodiments of the invention, an additional heterologous nucleic acid can encode a monoterpenoid synthase. In particular, in embodiments of the invention wherein the recombinant cell is to be employed in methods for production of a monoterpenoid, then it is preferred that the cell comprise a heterologous nucleic encoding a monoterpenoid synthase. Said monoterpenoid can for example be any of the monoterpenoids described herein below in the section "Terpenoids and terpenes". Thus, the monoterpenoid can for example be limonene, in which case the cell can comprise an additional nucleic acid encoding limonene synthase. A limonene synthase according to the invention is an enzyme capable of catalysing the following reaction:

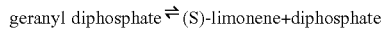
geranyl diphosphate ⇌ (S)-limonene+diphosphate

In particular the limonene synthase can be an enzyme classified under EC 4.2.3.16. Limonene synthase can for example be limonene synthase 1 from *Citrus limon* or a functional homologue thereof. In particular the limonene synthase can be a polypeptide comprising or consisting of SEQ ID NO: 13 or a functional homologue thereof sharing at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity with SEQ ID NO:13.

In another embodiment of the invention an additional heterologous nucleic acid can encode a sesquiterpene synthase. In particular, in embodiments of the invention wherein the host cell is to be employed in methods for production of a sesquiterpene, then it is preferred that the host cell comprise a heterologous nucleic encoding a sesquiterpene synthase. Said sesquiterpene can for example be any of the sesquiterpenes described herein below in the section "Terpenoids and terpenes". Said sesquiterpene synthase can be any sesquiterpene synthase, for example any of the sesquiterpene synthases described in Table 2 of Degenhardt et al., 2009, Id. Said table also outlines for synthesis of which particular sequiterpene each sesquiterpene synthase is useful.

In certain embodiments of the invention, the additional heterologous nucleic acid can encode an amorphadiene synthase, for example an amorpha-4,11-diene synthase. Said amorphadiene synthase can be any enzyme capable of catalysing the following reaction:

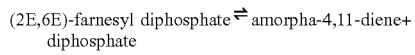
(2E,6E)-farnesyl diphosphate ⇌ amorpha-4,11-diene+ diphosphate

In particular the amorphadiene synthase to be used with the present invention can be any enzyme classified under E.C. 4.2.3.24.

In a particular embodiment, the amorphadiene synthase is amorphadiene synthase of SEQ ID NO: 8 or a functional homologue thereof, wherein said functional homologue shares at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity SEQ ID NO:8. The sequence identity is preferably determined as described herein. In addition to the aforementioned sequence identity, a functional homologue of amorphadiene synthase should also be capable of catalysing above-mentioned reaction.

In yet another embodiment of the invention, the additional heterologous nucleic acid can encode a GPP synthase. In particular, in embodiments of the invention wherein the recombinant cell is to be employed in methods for production of a GPP, then it is preferred that the cell comprise a heterologous nucleic encoding a GPP synthase. In addition, in embodiments of the invention wherein the cell is to be employed in methods for preparing monoterpenes, for example pinenes, myrcene and/or geraniol, said cell advantageously comprises a heterologous nucleic encoding a GPP synthase. Said GPP synthase can be any GPP synthase. Preferably, the GPP synthase is an enzyme capable of catalysing the following reaction:

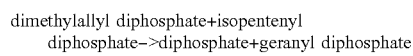
dimethylallyl diphosphate+isopentenyl diphosphate->diphosphate+geranyl diphosphate Preferably, the GPP synthase is an enzyme classified under EC 2.5.1.1. An example of a useful GPP synthase is *Humulus lupulus* GPP synthase, such as the *H. lupulus* GPP synthase described in Wang and Dixon, 2009, *Proc. Natl. Acad. Sci. USA* 106: 9914-9919. Other examples of useful GPP synthases are described in Orlova et al., 2009, Plant Cell, Vol. 21, 4002-4017 and in Chang et al., 2010, Plant Cell, Vol. 22, 454-467. The GPP synthase can also be a functional homologue of the *H. lupulus* synthase described in Wang and Dixon 2009, wherein said functional homologue shares at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity with *H. lupulus* GPP synthase.

Another example of a useful GPP synthase, which can be used with the present invention is GPP synthase 2 from *Abies grandis*. Thus, the GPP synthase can be GPP synthase 2 of *Abies grandis* or a fragment thereof or a functional homologue thereof retaining GPP synthase activity. Yet another example of a useful GPP synthase, which can be used with the present invention is GDPS of *Picea abies*. In particular the GPP synthase can be a polypeptide comprising or consisting of SEQ ID NO: 12 or a functional homologue thereof sharing at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity with SEQ ID NO:12.

In yet another embodiment of the invention, the additional heterologous nucleic acid can encode a FPP synthase, which is not endogenous to the host cell. In particular, in embodiments of the invention wherein the recombinant cell is to be employed in methods for production of a FPP, then it is preferred that the cell comprise a heterologous nucleic encoding a FPP synthase, which is not endogenous to the host cell. In addition, in embodiments of the invention wherein the recombinant cell is to be employed in methods for preparing sesquiterpenes, for example patchoulol, santalol, longiferolene or thujopsene, then it is preferred that the cell comprises a heterologous nucleic encoding a FPP synthase not endogenous to said host cell. Said FPP synthase can be any FPP synthase not endogenous to the host cell. In particular the FPP synthase can be an enzyme capable of catalysing production of FPP from DMAPP and IPP.

Examples of useful FPP synthases include *A. tridentate* FPPS-1 or *A. tridentate* FPPS-2. The FPP synthase can also be a functional homologue of *A. tridentate* FPPS-1 or *A. tridentate* FPPS-2, wherein said functional homologue shares at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity with *A. tridentate* FPPS-1 or *A. tridentate* FPPS-2.

The FDPS can be any FDPS, but it is preferred with the present invention that the FDPS is an enzyme, which is capable of catalyzing at least one of the following reactions:
 1) Synthesis of FPP from one DMAPP and 2 IPP
 2) Synthesis of FPP from one GPP and one IPP Other examples of FPP synthases, which can be used with the present invention include, but are not limited to FDPS (WH5701) and FDPS(CB101) from *Synechococcus*. Thus, the FPP synthase can be the polypeptide of SEQ ID NO: 14. The FPP synthase can also be the polypeptide of SEQ ID NO: 15. The FPP synthase can also be a functional homologue of SEQ ID NO: 14 or SEQ ID NO: 15, wherein said functional homologue shares at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity with SEQ ID NO:14 or SEQ ID NO:15.

Recombinant cells of the present invention can in certain embodiments contain an additional heterologous nucleic acid sequence encoding Geranylgeranyl Pyrophosphate Synthase (GGPPS). In particular, in embodiments of the invention wherein the cell is to be employed in methods for production of GGPP, then it is preferred that the recombinant cell comprise a heterologous nucleic encoding a GGPP synthase. In addition, in embodiments of the invention wherein the recombinant cell is to be employed in methods for preparing diterpenes or tetraterpenoids, for example carotenoids, then it is preferred that the cell comprise a heterologous nucleic encoding a GGPP synthase. GGPPS can be any GGPPS, but advantageously the GGPPS is an enzyme, which is capable of catalyzing at least one of the following reactions:
 3) Synthesis of GGPP from one DMAPP and 3 IPP
 4) Synthesis of GGPP from one GPP and 2 IPP
 5) Synthesis of GGPP from one FPP and 1 IPP In particular the GGPPS can be capable of catalysing synthesis of GGPP from one DMAPP and 3 IPP. In particular embodiments, the GGPP synthase is an enzyme classified under EC 2.5.1.1 or EC 2.5.1.10 or, even more preferably under EC 2.5.1.29.

The GGPPS can be GGPPS from a variety of sources, such as from bacteria, fungi or mammals. In particular, the GGPPS can be an enzyme from *S. alcidocaldarius* GGPP synthase and *H. lupulus* GGPP synthase or a functional homologue thereof sharing at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity with *S. acidocaldarius* GGPP synthase or with *H. lupulus* GGPP synthase.

In particular the GGPPS can be the GGPPS of SEQ ID NO:7 or a functional homologue thereof sharing at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity therewith.

The additional heterologous nucleic acid can also encode a GGPP synthase, which is includes but is not limited to GGPP synthases from *S. cerevisiae*. Thus, the GGPP synthase can be the GGPP synthase of SEQ ID NO: 23 or a functional homologue sharing at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity with SEQ ID NO: 23.

The additional heterologous nucleic acid can also encode an enzyme involved in the biosynthesis of a diterpene. For example the additional heterologous nucleic acid can also encode a diterpene synthase. Examples of diterpene synthases include but are not limited to ent-kaurene synthase. An example of ent-kaurene synthase is the polypeptide of SEQ ID NO: 17 or a functional homologue thereof sharing at least 70%, preferably at least 80%, yet more preferably at least 85%, yet more preferably at least 90%, yet more preferably at least 95% sequence identity therewith. The heterologous nucleic acid can also encode an ent-copalyl-diphosphate synthase, such as the polypeptide of SEQ ID NO: 18 or a functional homologue thereof sharing at least 70%, preferably at least 80%, yet more preferably at least 85%, yet more preferably at least 90%, yet more preferably at least 95% sequence identity therewith.

The additional heterologous nucleic acid can also encode an isoprene synthase. Said isoprene synthase can be any enzyme capable of catalyzing the following reaction:

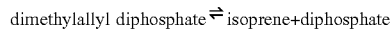

In particular, the isoprene synthase can be any isoprene synthase classified under EC 4.2.3.27.

The additional heterologous nucleic acid sequence can also encode any enzyme used in the process of preparing the target product terpenoid or terpene. Said enzyme can for example be any enzyme "located downstream" of the isopentenyl-pyrophosphate or dimethylallyl-pyrophosphate, which is intended to indicate that the enzyme or enzymes catalyse production in the recombinant cell of metabolites produced from IPP or DMAPP. Said enzyme can thus for example can be dimethylallyltransferase (EC 2.5.1.1), and geranyltranstransferase (EC 2.5.1.10).

Recombinant cells of the invention can furthermore comprise one or more additional heterologous nucleic acids encoding one or more enzymes, for example, phosphomevalonate kinase (EC 2.7.4.2), diphosphomevalonate decarboxylase (EC 4.1.1.33), 4-hydroxy-3-methylbut-2-en-1-yl diphosphate synthase (EC 1.17.7.1), 4-hydroxy-3-methylbut-2-enyl diphosphate reductase (EC 1.17.1.2), isopentenyl-diphosphate Delta-isomerase 1 (EC 5.3.3.2), short-chain Z-isoprenyl diphosphate synthase (EC 2.5.1.68), dimethylallyltransferase (EC 2.5.1.1), geranyltranstransferase (EC 2.5.1.10) or geranylgeranyl pyrophosphate synthetase (EC 2.5.1.29).

Additionally and in some embodiments alternatively, recombinant cells of the invention can also comprise one or more additional heterologous nucleic acids encoding one or more enzymes, for example, acetoacetyl CoA thiolose, HMG-CoA reductase or the catalytic domain thereof, HMG-CoA synthase, mevalonate kinase, phosphomevalonate kinase, phosphomevalonate decarboxylase, isopentenyl pyrophosphate isomerase, farnesyl pyrophosphate synthase, D-1-deoxyxylulose 5-phosphate synthase, and 1-deoxy-D-xylulose 5-phosphate reductoisomerase and farnesyl pyrophosphate synthase, wherein in said alternative embodiments the cells express a phenotype of increased mevalonate production or accumulation or both.

The invention described here relates to recombinant cells genetically engineered to have increased mevalonate production and/or have higher metabolic flux through the mevalonate biochemical pathway, and can also comprise additional recombinant expression constructs encoding enzymes useful for increasing products of the mevalonate pathway, particularly isoprenoids. In some embodiments the genetically engineered recombinant cells express a phenotype of increased mevalonate production or accumulation or both Said additional heterologous nucleic acid sequences encoding a terpene synthase can be generally provided operably linked to a nucleic acid sequence directing expression of said terpene synthase in the recombinant cell. The nucleic acid sequence directing expression of terpene synthase in the recombinant cell can be and generally is a promoter sequence, and preferably said promoter sequence is selected according the particular host cell. The promoter can for example be any of the promoters described herein above in the section "Promoter sequence".

In another embodiment the recombinant cell can comprise an additional heterologous nucleic acid encoding a dimethylallyltyrosine synthase. Such cells are for example useful for production of DMAT. Said dimethylallyltyrosine synthase is preferably an enzyme classified under EC 2.5.1.34. For example the dimethylallyltyrosine synthase can be the protein of SEQ ID NO: 5 or a functional homologue thereof sharing at least 70%, preferably at least 80%, such as at least 85%, for example at last 90%, such as at least 95% sequence identity therewith.

The host cell can comprise an additional heterologous nucleic acid encoding a prenyl transferase. Said prenyl transferase may be any enzyme capable of catalysing transfer of an allylic prenyl group to an acceptor molecule. For example, the prenyltransferase may be a prenyl diphosphate synthase. Examples of useful prenyltransferases can be found in Bonitz et al., 2011 *PLoS One* 6(11):E27336.

Figure 2B:
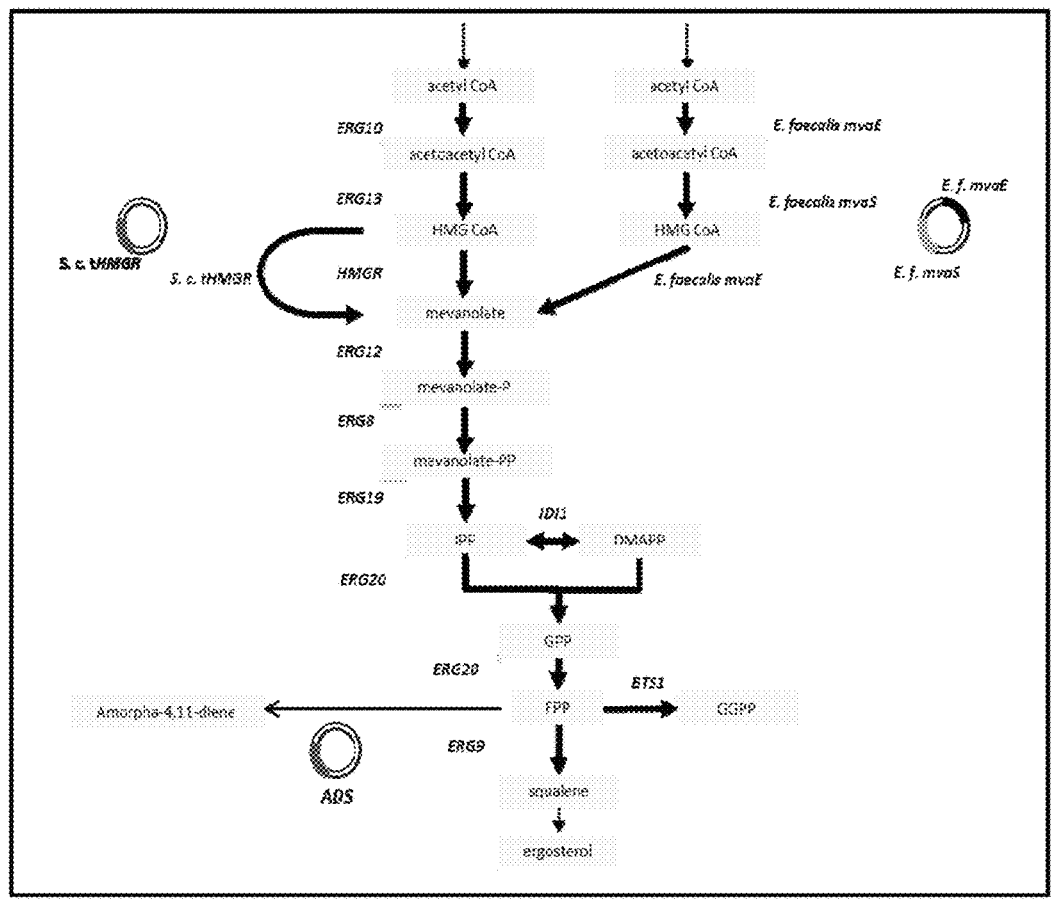
FIG. 2B shows an overview of the mevalonate pathway together by a modified pathway. The middle column starting with ERG10 shows the endogenous pathway of *S. cerevisiae*. The right column shows an example of a modified pathway according to the invention. The plasmids used in the methods described in Example 4 are also outlined.

An important goal of engineering of eukaryotic cells, such as yeast for production of isoprenoid molecules is to find ways to circumvent the extensive regulation of the mevalonate pathway (see FIG. 2A) to boost production. In particular, the HMGR step, which is a rate-limiting step, is subject to feedback inhibition by different intermediates and derivatives from the mevalonate pathway. In particular, *S. cerevisiae* encodes two HMGR paralogs, HMGR1 and HMGR2 that both are controlled by feedback inhibition, although in different ways. Eukaryotic HMGRs are typically endoplasmic reticulum (ER)-resident integral membrane proteins consisting of two distinct domains: a hydrophobic $NH_2$-terminal membrane anchor consisting of 2-8 transmembrane segments, and a COOH-terminal catalytic domain that extends into the cytoplasm. The COOH-terminal catalytic domain of Class I HMGRs forms a dimer that comprises the active enzyme and each monomer contributes catalytic residues to form the active site. The budding yeast *S. cerevisiae* encodes two HMGR genes, designated HMG1 and HMG2. HMGR1 is the primary source of HMGR activity during aerobic growth (Burg et al., 2011 *Prog Lipid Res.* 50(4):403-410). It has been found that overexpression of a truncated version of the *S. cerevisiae* HMGR1 consisting of the catalytically active C-terminus (region from amino acids 619-1025) can stimulate mevalonate levels and increase production of heterologous isoprenoid derived molecules (Rico et al, 2010 *Appl Environ Microbiol*. October; 76(19):6449-54). Accordingly, in certain additional or alternative embodiments of the invention the recombinant cell comprises an additional heterologous nucleic acid sequence encoding a truncated version of HMGR. Said truncated version of HMGR most advantageously comprises a catalytically active C-terminus, for example it can comprise the catalytically active C-terminus of HMGR1 of *S. cerevisiae* where, for example, amino acids 2-530 have been deleted from the N-terminus. For example said truncated version of HMGR can be truncated HMGR1 described in Rico et al., 2010. In particular, the truncated HMGR is truncated HMGR derived from SEQ ID NO: 8 or a functional homologue thereof sharing at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity therewith over the entire length. Said functional homologue preferably comprises at the most 550 amino acids, such as at the most 527 amino acids and is capable of catalysing reduction of HMG CoA to form mevanolate.

Recombinant cells of the invention can also have been modulated to reduce activity of squalene synthase. Squalene synthase according to the invention is preferably an enzyme classified under EC 2.5.1.21. In particular, if the host cell is a yeast cell, then said yeast cell can have been modulated to reduced expression of the ERG-9 gene. This can for example be accomplished by placing the ORF encoding squalene synthase under the control of a weak promoter, such as any of the weak promoters described herein in the section "Promoter sequence". This can be accomplished, for example, by replacing the entire wild type gene encoding squalene synthase or by replacing the wild type promoter. Optionally, the cell is a recombinant cell that comprises a heterologous sequence that reduces expression of mRNA encoding squalene synthase. In particular embodiments, the heterologous nucleic acid insert sequence can be positioned between the promoter sequence and the ORF encoding squalene synthase. Said heterologous insert sequence can be any of the heterologous insert sequences described herein below in the section "Heterologous insert sequence".

The invention also provides methods and recombinant cells wherein squalene synthase activity is reduced with using a motif that de-stabilizes mRNA transcripts. Thus, recombinant cells of the present invention can comprise a nucleic acid comprising a promoter sequence operably linked to an open reading frame (ORF) encoding squalene synthase, and a nucleotide sequence comprising a motif that de-stabilizes mRNA transcripts. Said motif, can be any of the motif that de-stabilize mRNA transcripts described herein below in the section "Motif that de-stabilize mRNA transcripts".

Dual Function Enzyme

Recombinant cells according to the invention can also comprise a heterologous nucleic acid sequence encoding a dual function enzyme, wherein said dual function enzyme is an acetoacetyl-CoA thiolase and a HMG-CoA reductase. Similarly, recombinant eukaryotic cells of the invention can comprise a heterologous nucleic acid sequence encoding a dual function enzyme, wherein said dual function enzyme is an acetoacetyl-CoA thiolase and a HMG-CoA reductase.

Thus, a dual function enzyme according to the invention is preferably an enzyme, which is capable of catalysing both of the following reactions:

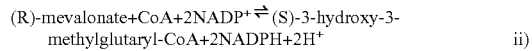

Enzymes capable of catalysing reaction i) are classified under E.C: 2.3.19, whereas enzymes capable of catalysing reaction ii) are classified under E.C. 1.1.1.34. Thus preferred dual function enzymes to be used with the present invention can be classified either under E.C. 2.3.19 or under E.C. 1.1.1.34.

Said dual function enzyme can be derived from any useful source. In particular, the dual function enzyme can be of prokaryotic origin.

In a particular embodiment, the dual function enzyme is the enzyme encoded by *E. faecalis* gene mvaE or a functional homologue thereof. Thus the dual function enzyme can be the polypeptide of SEQ ID NO: 9 or a functional homologue thereof, wherein said functional homologue shares at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity SEQ ID NO: 9. The sequence identity is preferably determined as described herein.

In addition to the aforementioned sequence identity, a functional homologue of the enzyme encoding by *E. faecalis* gene mvaE should also be capable of catalysing reactions i) and ii) outlined herein above in this section.

HMGS

Recombinant cells useful according to this invention can also comprise a heterologous nucleic acid sequence encoding a 3-hydroxy-3-methyl-glutaryl coenzyme A synthase (HMGS). Thus, the recombinant eukaryotic cells of the present invention can in preferred embodiment comprise a heterologous nucleic acid sequence encoding a 3-hydroxy-3-methyl-glutaryl coenzyme A synthase (HMGS).

The HMGS to be used with the present invention is preferably enzyme, which is capable of catalysing the following reaction:

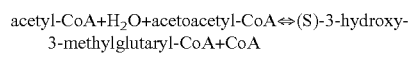

In particular the HMGS to be used with the present invention can be any enzyme classified under E.C. 2.3.3.10.

Said HMGS can be derived from any useful source. In particular, the HMGS can be of prokaryotic origin.

In one preferred embodiment the HMGS is the enzyme encoded by *E. faecalis* gene mvaS or a functional homologue thereof. Thus the HMGS can be the polypeptide of SEQ ID NO: 10 or a functional homologue thereof, wherein said functional homologue shares at least 70%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity SEQ ID NO: 10. The sequence identity is preferably determined as described herein.

In addition to the aforementioned sequence identity, then a functional homologue of the enzyme encoding by *E. faecalis* gene mvaS should also be capable of catalysing above-mentioned reaction.

Methods for Producing Terpenes or Terpenoids

As mentioned herein above, recombinant cells of this invention are useful in enhancing yield of isoprenoid pyrophosphates and/or terpenes and/or terpenoids.

Specific particular embodiments of the recombinant cells of the invention can therefore be genetically engineered in order to increase accumulation of isoprenoid pyrophosphate precursors and thus to increase yield of terpenoid or terpene products resulting from enzymatic conversion of said isoprenoids pyrophosphates.

Accordingly, in one aspect the present invention relates to a method of producing a terpene or a terpenoid, said method comprising the steps of cultivating a recombinant cell as described herein under conditions in which a terpene or terpenoid product is produced by the cell, and isolating said terpene or terpenoid.

In a particular example using a recombinant yeast cell embodiment, said cell having reduced activity of the ERG20 gene results in enhanced accumulation of IPP and DMAPP. DMAPP and IPP accumulation can be exploited for increased production of GPP, FPP and GGPP when combined with a heterologous GGP synthase, or heterologous FPP synthase or heterologous GGPP synthase.

Thus, in another aspect, the invention provides methods for producing isoprenoid pyrophosphate that include but are not limited to farnesyl-pyrophosphate (FPP), isopentenyl-pyrophosphate (IPP), dimethylallyl-pyrophosphate (DMAPP), geranyl-pyrophosphate (GPP) and/or geranylgeranyl-pyrophosphate (GGPP), by culturing a recombinant cell according to the invention under conditions where said isoprenoid pyrophosphates are produced and then isolating said isoprenoic pyrophosphate.

In certain additional or alternative embodiments, mevalonate accumulation is enhanced in a recombinant cell, e.g. a eukaryotic cell that comprises a heterologous nucleic acid sequence encoding a dual function enzyme, wherein said dual function enzyme is an acetoacetyl-CoA thiolase and a HMG-CoA reductase and optionally further comprising a heterologous nucleic acid sequence encoding a 3-hydroxy-3-methyl-glutaryl coenzyme A synthase (HMGS), accumulation of mevalonate. In further additional or alternative embodiments, compounds having mevalonate as a metabolic precursor also accumulate in said recombinant cells when mevalonate production, accumulation or both is enhanced as described herein. Such cells are advantageously employed for producing IPP and DMAPP, and for enhanced production of GPP, FPP and GGPP, when said recombinant cell comprises a heterologous GGP synthase, or heterologous FPP synthase or heterologous GGPP synthase.

Thus, it is also an aspect of the invention to provide methods for producing an isoprenoid pyrophosphate that is farnesyl-pyrophosphate (FPP), isopentenyl-pyrophosphate (IPP), dimethylallyl-pyrophosphate (DMAPP), geranyl-pyrophosphate (GPP) and/or geranylgeranyl-pyrophosphate (GGPP), by culturing said recombinant cell comprising a heterologous nucleic acid sequence encoding a dual function enzyme, wherein said dual function enzyme is an acetoacetyl-CoA thiolase and a HMG-CoA reductase and optionally further comprising a heterologous nucleic acid sequence encoding a 3-hydroxy-3-methyl-glutaryl coenzyme A synthase (HMGS), and optionally further comprising one or more of the additional heterologous nucleic acid sequences described herein above in the section "Additional heterologous nucleic acids", under conditions wherein said FPP, IPP, DMAPP, GPP or GGPP is produced, and then isolating said FPP, IPP, DMAPP, GPP or GGPP.

The invention provides methods and recombinant cells for producing terpenes or terpenoids, particularly having increased yields thereof. In certain embodiments the terpenoid or the terpene to be produced by the methods of the invention is a hemiterpenoid, monoterpene, sesquiterpenoid, diterpenoid, sesterpene, triterpenoid, tetraterpenoid or polyterpenoid.

More specifically, the terpenoid or terpene is farnesyl phosphate, farnesol, geranylgeranyl, geranylgeraniol, isoprene, prenol, isovaleric acid, geranyl pyrophosphate, eucalyptol, limonene, pinene, farnesyl pyrophosphate, artemisinin, bisabolol, geranylgeranyl pyrophosphate, retinol, retinal, phytol, taxol, forskolin, aphidicolin, lanosterol, lycopene or carotene.

Recombinant cells according to the invention useful for producing said terpenes and terpenoids have been genetically engineered to exhibit reduced farnesyl diphosphate production according to the methods set forth herein. In said embodiments, the phenotype of the recombinant cell includes decreasing turnover of IPP to FPP and/or of DMAPP to FPP. Recombinant cells according to the invention also exhibit a phenotype wherein FPP, IPP, DMAPP, GPP and GGPP accumulation is enhanced, by genetically engineering said cells as set forth herein. In certain additional embodiments, the invention provides recombinant cells useful in the disclosed inventive methods for producing and recovering FPP, IPP, DMAPP, GPP or GGPP from said cell, wherein said recombinant cells are cultured under conditions wherein FPP, IPP, DMAPP, GPP and GGPP are produced by the cell, advantageously in enhanced yield.

In further embodiments, the recombinant cells further comprise, endogenously or as the result of introducing additional heterologous recombinant expression constructs, enzyme or enzymes comprising a metabolic pathway for producing terpenes or terpenoids according to the invention. In said embodiments, terpene or terpenoid production is enhanced as the result of reduced expression of FPP, GPP or an enzyme having both FPP and GPP synthease activities, or in addition or alternatively increased accumulation of mevalonate precursors using recombinant cells and methods as set forth herein.

Alternatively, said IPP, FPP, GPP, DMAPP, or GGPP precursors can be recovered from said recombinant cells and used in further processes for producing the desired terpenoid product compound. The further process can take place in the same cell culture as the process performed and defined herein above, such as the accumulation of the terpenoid precursors by the cell of the present invention. Alternatively, the recovered precursors can be added to another cell culture, or a cell free system, to produce the desired products.

As the isoprenoids pyrophosphates can serve as intermediates, endogenous production of terpenoids or terpenes can occur based on the isoprenoid pyrophosphates. Also, the recombinant cells of the invention can have additional genetic modifications such that they are capable of performing both the accumulation of the isoprenoids pyrophosphates and whole or substantially the whole subsequent biosynthesis process to a desired terpenoid or terpene product.

Thus, in certain embodiments the method of the invention further comprises recovering a compound being biosynthesised from said IPP, FPP, DMAPP, GPP or GGPP precursors in the recombinant cells provided by this invention.

In alternative embodiments, the invention provides methods and genetically engineered recombinant cells wherein production or accumulation of IPP, DMAPP or both is enhanced, comprising culturing recombinant cells of the invention wherein metabolic activity farnesyl diphosphate synthase activity, geranyl diphosphate synthase activity and/or the activity of an enzyme having both farnesyl diphosphate synthase and geranyl diphosphate synthase activity, is downregulated as set forth herein.

In additional or alternative embodiments, said recombinant cell comprises a heterologous nucleic acid sequence encoding a dual function enzyme as set forth herein, wherein said cell produced or accumulates or both enhanced metabolites in the mevalonate pathway, particular mevalonate, including inter alia expression of heterologous HMGS. In further additional or alternative embodiments, said recombinant cell is a yeast cell that is genetically engineered for reduced ERG9 expression or activity.

In additional specific embodiments, the invention provides methods and recombinant cells for producing GPP, particular wherein production, accumulation or both of GPP is enhanced, wherein GPP is obtained in advantageously greater yields by culturing a recombinant cell that has been genetically engineered for reduced expression of farnesyl diphosphate synthase activity, geranyl diphosphate synthase activity and/or the activity of an enzyme having both farnesyl diphosphate synthase and geranyl diphosphate synthase activity, and wherein said recombinant cell further comprises a recombinant expression construct encoding a heterologous GPP synthase. In additional or alternative embodiments, the recombinant cell comprises a heterologous nucleic acid sequence encoding a dual function enzyme as set forth herein, wherein said cell produced or accumulates or both enhanced metabolites in the mevalonate pathway, particular mevalonate, including inter alia expression of heterologous HMGS. In further additional or alternative embodiments, said recombinant cell is a yeast cell that is genetically engineered for reduced ERG9 expression or activity.

In additional specific embodiments, the invention provides methods and recombinant cells for producing FPP, particular wherein production, accumulation or both of FPP is enhanced, wherein FPP is obtained in advantageously greater yields by culturing a recombinant cell that has been genetically engineered for reduced expression of farnesyl diphosphate synthase activity, geranyl diphosphate synthase activity and/or the activity of an enzyme having both farnesyl diphosphate synthase and geranyl diphosphate synthase activity, and wherein said recombinant cell further comprises a recombinant expression construct encoding a heterologous FPP synthase. In additional or alternative embodiments, the recombinant cell comprises a heterologous nucleic acid sequence encoding a dual function enzyme as set forth herein, wherein said cell produced or accumulates or both enhanced metabolites in the mevalonate pathway, particular mevalonate, including inter alia expression of heterologous HMGS. In further additional or alternative embodiments, said recombinant cell is a yeast cell that is genetically engineered for reduced ERG9 expression or activity.

In additional specific embodiments, the invention provides methods and recombinant cells for producing GGPP, particular wherein production, accumulation or both of GGPP is enhanced, wherein GGPP is obtained in advantageously greater yields by culturing a recombinant cell that has been genetically engineered for reduced expression of farnesyl diphosphate synthase activity, geranyl diphosphate synthase activity and/or the activity of an enzyme having both farnesyl diphosphate synthase and geranyl diphosphate synthase activity, and wherein said recombinant cell further comprises a recombinant expression construct encoding a heterologous GGPP synthase. In additional or alternative embodiments, the recombinant cell comprises a heterologous nucleic acid sequence encoding a dual function enzyme as set forth herein, wherein said cell produced or accumulates or both enhanced metabolites in the mevalonate pathway, particular mevalonate, including inter alia expression of heterologous HMGS. In further additional or alternative embodiments, said recombinant cell is a yeast cell that is genetically engineered for reduced ERG9 expression or activity.

In additional specific embodiments, the invention provides methods and recombinant cells for producing isoprene, particular wherein production, accumulation or both of isoprene is enhanced, wherein isoprene is obtained in advantageously greater yields by culturing a recombinant cell that has been genetically engineered for reduced expression of farnesyl diphosphate synthase activity, geranyl diphosphate synthase activity and/or the activity of an enzyme having both farnesyl diphosphate synthase and geranyl diphosphate synthase activity, and wherein said recombinant cell further comprises a recombinant expression construct encoding a heterologous isoprene synthase. In additional or alternative embodiments, the recombinant cell comprises a heterologous nucleic acid sequence encoding a dual function enzyme as set forth herein, wherein said cell produced or accumulates or both enhanced metabolites in the mevalonate pathway, particular mevalonate, including inter alia expression of heterologous HMGS. In further additional or alternative embodiments, said recombinant cell is a yeast cell that is genetically engineered for reduced ERG9 expression or activity. In certain specific embodiments, said isoprene is isolated and further polymerized to produce isoprene rubber.

The invention specifically provides methods and recombinant cells for producing terpenes and terpenoids In particular embodiments, the recombinant cells provide herein are used to produce a monoterpenoid, including but not limited to the monoterpenoids described herein in the section "Terpenoids and terpenes". As provided herein, said monoterpenoids are produced by culturing a recombinant cell that has been genetically engineered for reduced expression of farnesyl diphosphate synthase activity, geranyl diphosphate synthase activity and/or the activity of an enzyme having both farnesyl diphosphate synthase and geranyl diphosphate synthase activity, and wherein said recombinant cell further comprises a recombinant expression construct encoding a heterologous GPP synthase and one or more additional heterologous nucleic acids each encoding an enzyme of the biosynthetic pathway to produce said monoterpenoid from GPP, for example said heterologous nucleic acids can encode any of the monoterpenoid synthases described herein in the section "Additional heterologous nucleic acids. In additional or alternative embodiments, the recombinant cell comprises a heterologous nucleic acid sequence encoding a dual function enzyme as set forth herein, wherein said cell produced or accumulates or both enhanced metabolites in the mevalonate pathway, particular mevalonate, including inter alia expression of heterologous HMGS. In further additional or alternative embodiments, said recombinant cell is a yeast cell that is genetically engineered for reduced ERG9 expression or activity. Exemplary monoterpenoids include but are not limited to limonene, in which case said monoterpenoid synthase can be any of the limonene synthases described herein above in the section "Additional heterologous nucleic acid".

In additional particular embodiments, the recombinant cells provide herein are used to produce sesquiterpenoids or triterpenoids, including but not limited to the sesquiterpenoids or triterpenoids described herein in the section "Terpenoids and terpenes". As provided herein, said sesquiterpenoids or triterpenoids are produced by culturing a recombinant cell that has been genetically engineered for reduced expression of farnesyl diphosphate synthase activity, geranyl diphosphate synthase activity and/or the activity of an enzyme having both farnesyl diphosphate synthase and geranyl diphosphate synthase activity, and wherein said recombinant cell further comprises a recombinant expression construct encoding a heterologous FPP synthase and one or more additional heterologous nucleic acids each encoding an enzyme of the biosynthetic pathway to produce said sesquiterpenoid or triterpenoid from FPP, for example said heterologous nucleic acids can encode any of the sesquiterpenoid or triterpenoid synthases described herein in the section "Additional heterologous nucleic acids. In additional or alternative embodiments, the recombinant cell comprises a heterologous nucleic acid sequence encoding a dual function enzyme as set forth herein, wherein said cell produced or accumulates or both enhanced metabolites in the mevalonate pathway, particular mevalonate, including inter alia expression of heterologous HMGS. In further additional or alternative embodiments, said recombinant cell is a yeast cell that is genetically engineered for reduced ERG9 expression or activity. Exemplary sesquiterpenoids include but are not limited to amorphadiene or artemisinin, in which case one sesquiterpenoid synthase can be amorphadiene synthase, such as any of the amorphadiene synthases described herein above in the section "Additional heterologous nucleic acids". Exemplary triterpenoids include but are not limited to cycloartenol, curcubitacin E, azadirachtin A, lupeol, beta-amyrin and saponins, in which case said triterpenoids synthase can be any of the EC 2.5.1.21 (squalene synthase) synthases described herein above in the section "Additional heterologous nucleic acid".

In additional particular embodiments, the recombinant cells provide herein are used to produce diterpenoids or tetraterpenoids, including but not limited to the diterpenoids or tetraterpenoids described herein in the section "Terpenoids and terpenes". As provided herein, said diterpenoids or tetraterpenoids are produced by culturing a recombinant cell that has been genetically engineered for reduced expression of farnesyl diphosphate synthase activity, geranyl diphosphate synthase activity and/or the activity of an enzyme having both farnesyl diphosphate synthase and geranyl diphosphate synthase activity, and wherein said recombinant cell further comprises a recombinant expression construct encoding a heterologous GPP synthase, a heterologous FPP synthase and one or more additional heterologous nucleic acids each encoding an enzyme of the biosynthetic pathway to produce said diterpenoid or tetraterpenoid from GPP, FPP and/or GPP synthase, for example said heterologous nucleic acids can encode any of the diterpenoid or tetraterpenoid synthases described herein in the section "Additional heterologous nucleic acids. In additional or alternative embodiments, the recombinant cell comprises a heterologous nucleic acid sequence encoding a dual function enzyme as set forth herein, wherein said cell produced or accumulates or both enhanced metabolites in the mevalonate pathway, particular mevalonate, including inter alia expression of heterologous HMGS. In further additional or alternative embodiments, said recombinant cell is a yeast cell that is genetically engineered for reduced ERG9 expression or activity. Exemplary diterpenoids include but are not limited to casbene, taxadiene, abietadiene, paclitaxel, and incensole, in which case said diterpenoid synthase can be any GGPP synthase, described herein above in the section "Additional heterologous nucleic acids". Exemplary tetraterpenoids include but are not limited to lutein, beta-caroten, zeaxanthin, astaxanthin, and apo-carotenoids like retinol, beta-ionone, abscissic acid and bixin, in which case said tetraterpenoid synthase can be any of the EC 2.5.1.32 synthases described herein above in the section "Additional heterologous nucleic acids".

Terpenoids and Terpenes

The invention provides methods and recombinant cells for producing terpenoids, terpenes or isoprenoids (terpenoids are also commonly referred to as isoprenoids) using the recombinant cells of the invention characterised by reduced farnesyl diphosphate synthase activity, geranyl diphosphate synthase activity and/or the activity of an enzyme having both farnesyl diphosphate synthase and geranyl diphosphate synthase activity, wherein in particular embodiments the recombinant cell is a yeast cell expressing reduced ERG20 activity.

Terpenoids are classified according to the number of isoprene units (depicted below) used.

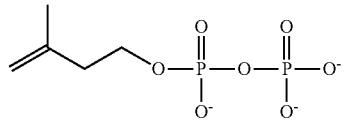

The classification thus comprises the following classes:
Hemiterpenoids, 1 isoprene unit (5 carbons)
Monoterpenoids, 2 isoprene units (10C)
Sesquiterpenoids, 3 isoprene units (15C)
Diterpenoids, 4 isoprene units (20C) (e.g. ginkgolides)
Sesterterpenoids, 5 isoprene units (25C)
Triterpenoids, 6 isoprene units (30C)
Tetraterpenoids, 8 isoprene units (40C) (e.g. carotenoids)
Polyterpenoid with a larger number of isoprene units.

Hemiterpenoids include isoprene, prenol and isovaleric acid.

Monoterpenoids include Geranyl pyrophosphate, Eucalyptol, Limonene and Pinene.

Sesquiterpenoids include Farnesyl pyrophosphate, amorphadiene, Artemisinin and Bisabolol.

Diterpenoids include Geranylgeranyl pyrophosphate, Retinol, Retinal, Phytol, Taxol, Forskolin and Aphidicolin. Another non-limiting example of a diterpene is ent-kaurene.

Triterpenoids include Squalene and Lanosterol.

Tetraterpenoids include Lycopene and Carotene and carotenoids.

Terpenes are hydrocarbons resulting from the combination of several isoprene units. Terpenoids can be thought of as terpene derivatives. The term terpene is sometimes used broadly to include the terpenoids. Just like terpenes, the terpenoids can be classified according to the number of isoprene units used. The present invention is focussed on terpenoids and in particular terpenoids derived from the isoprenoid pyrophosphates farnesyl-pyrophosphate (FPP), isopentenyl-pyrophosphate (IPP), dimethylallyl-pyrophosphate (DMAPP), geranyl-pyrophosphate (GPP) and/or geranylgeranyl-pyrophosphate (GGPP).

By terpenoids is understood terpenoids of the Hemiterpenoid class such as but not limited to isoprene, prenol and isovaleric acid; terpenoids of the Monoterpenoid class such as but not limited to geranyl pyrophosphate, eucalyptol, limonene and pinene; terpenoids of the Sesquiterpenoids class such as but not limited to farnesyl pyrophosphate, artemisinin and bisabolol; terpenoids of the diterpenoid class such as but not limited to geranylgeranyl pyrophosphate, retinol, retinal, phytol, taxol, forskolin and aphidicolin; terpenoids of the Triterpenoid class such as but not limited to lanosterol; terpenoids of the Tetraterpenoid class such as but not limited to lycopene and carotene.

The invention also relates to methods for production of other prenylated compounds. Thus the invention relates to methods for production of any compound, which has been prenylated to contain isoprenoid side-chains.

TABLE 1

Nucleic acid and amino acid sequences.

| | |
|---|---|
| SEQ ID NO: 1 | KEX2 promoter sequence |
| SEQ ID NO: 2 | Example of heterologous insert sequence |
| SEQ ID NO: 3 | CYC1 promoter sequence |
| SEQ ID NO: 4 | Protein sequence of farnesyl diphosphate synthase (ERG20 gene) from S. cerevisiae |
| SEQ ID NO: 5 | Protein sequence of DmaW from Claviceps purpurea (CpDmaW) |
| SEQ ID NO: 6 | Protein sequence of FgaMT of Aspergillus fumigatus |
| SEQ ID NO: 7 | Protein sequence of GGPPS of S. acidocaldarius |
| SEQ ID NO: 8 | Protein sequence of HMGR1 (tHMGR1) from S. cerevisiae (YML075C). |
| SEQ ID NO: 9 | Protein sequence of E. faecalis mvaE |
| SEQ ID NO: 10 | Protein sequence of E. faecalis mvaS |
| SEQ ID NO: 11 | Artemisia annua amorpha-4,11-diene synthase (ADS) |
| SEQ ID NO: 12 | Protein sequence of GPPS2 from Abies grandis (AAN01134) |
| SEQ ID NO: 13 | Protein sequence of LIMS1 from Citrus limon (Q8L5K3) |
| SEQ ID NO: 14 | Protein sequence of FDPS (WH5701) from Synechococcus |
| SEQ ID NO: 17 | Protein sequence of Ent-Kaurene synthase from A. thaliana |
| SEQ ID NO: 18 | ent-Copalyl-diphospate Synthase (CDPS) from A. thaliana (NP_192187) |
| SEQ ID NO: 19 | ERG20 S. cerevisiae (NP_012368) |
| SEQ ID NO: 20 | FPPS1 from A. tridentata (Q7XYS9) |
| SEQ ID NO: 21 | FPPS2 from A. tridentata (Q7XYT0) |
| SEQ ID NO: 22 | FPPS2 from A. thaliana (NP_974565) |
| SEQ ID NO: 23 | GGPPS (BTS1) S. cerevisiae (NP_015256) |
| SEQ ID NO: 25 | GGPPS S. acidocaldarius (YP_254812) |
| SEQ ID NO: 26 | GPPS(IDS2)from Picea abies (ACA21458) |
| SEQ ID NO: 27 | S. cerevisiae ERG9 gene for squalene synthetase (X59959.1) |

EXAMPLES

Example 1

Substitution of the Native ERG20 Promoter with a Weak KEX2 Promoter

The wildtype ERG20 promoter region was replaced by a KEX2 promoter sequence by homologous recombination. A DNA fragment encompassing an ERG20 promoter upstream sequence (for homologous recombination), an expression cassette for the gene (NatR) that confers resistance to nourseothricin, a KEX2 promoter, and an ERG20 ORF sequence (for homologous recombination) were generated by PCR. An overview of the PCR fragment and the homologous recombination is provided in FIG. 1A. The sequence of the KEX2 promoter is provided as SEQ ID NO: 1. The PCR DNA fragment was transformed in an S. cerevisiae host strain that subsequently was selected on nourseothricin-containing growth plates. Clones with successful exchange of the native ERG20 promoter by the KEX2 promoter were identified. Such yeast strains are also referred to as KEX2-ERG20 strains herein.

Figure 1B:
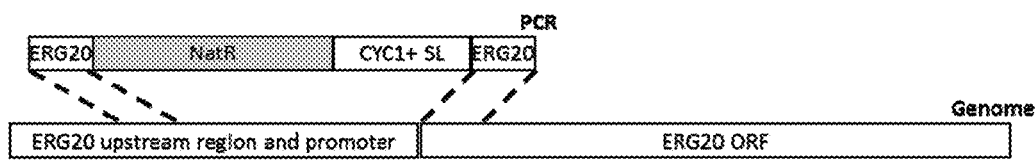
FIG. 1C shows CYC1+SL refers to the CYC1 promoter linked to the heterologous insert sequence of SEQ ID NO:2.
Figure 1C:
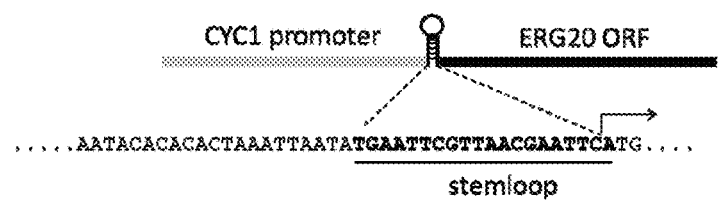

Substitution of the Native ERG20 Promoter with a CYC1 Promoter and a Short Sequence that Creates a Stem-Loop Structure in 5'UTR of the ERG20 Gene The wildtype ERG20 promoter region was replaced by the CYC1 promoter sequence and a heterologous 5'UTR sequence by homologous recombination. The 5'UTR region contains a sequence that folds up as a stem-loop structure, which partially blocks the 5'->3' directed ribosomal scanning for the AUG and thus reduces the translation of the transcript. The sequence of the 5'UTR region is provided as SEQ ID NO: 2. A DNA fragment encompassing an ERG20 promoter upstream sequence (for homologous recombination), an expression cassette for the gene (NatR) that confers resistance to nourseothricin, a CYC1 promoter with a 5'UTR sequence containing a stem-loop structure sequence, and an ERG20 ORF sequence (for homologous recombination) were generated by PCR. An overview of the PCR fragment and the homologous recombination is provided in FIG. 1B and a detailed figure showing the 5'UTR region is provided in FIG. 1C. The sequence of the CYC1 promoter is provided as SEQ ID NO:3. The DNA fragment was transformed in an S. cerevisiae host strain that subsequently was selected on nourseothricin-containing growth plates. Clones with successful exchange of the native ERG20 promoter by the CYC1 promoter with the stem-loop containing 5'UTR sequence were identified. Such yeast strains are also referred to as CYC1(5%)-ERG20 herein.

Example 2. Assessment of DMAPP Accumulation

The first part of the Mevalonate pathway produces the isoprenoid pyrophosphates isopentenyl pyrophosphate/isopentenyl diphosphate (IPP) and dimethylallyl pyrophosphate/dimethylallyl diphosphate (DMAPP). An overview of the pathway is provided in FIG. 2. The isopentenyl-diphosphate delta isomerase 1 (IDI1) catalyzes the interconversion between IPP and DMAPP molecules and this ratio is normally 5:1 in S. cerevisiae. The present invention describes that accumulation of IPP and DMAPP creates a potential for making more geranyl pyrophosphate (GPP) (joining one DMAPP and one IPP), farnesyl pyrophosphate (FPP) (joining one DMAPP and two IPPs), and geranylgeranyl pyrophosphate (GGPP) (joining one DMAPP and three IPPs) when combined with expression of either a heterologous GPP synthase (GPPS), or a heterologous FPP synthase (FPPS) or a heterologous GGPP synthase (GGPPS).

Figure 3:
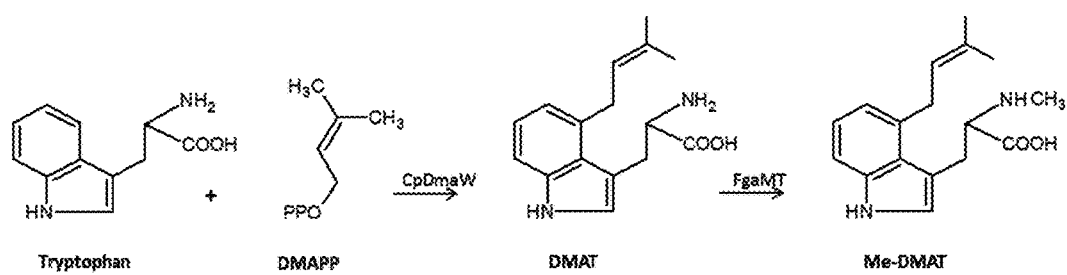
FIG. 3 shows the reactions catalysed by CpDmaW and FgaMT.

The two first steps of the biosynthetic pathway for the ergot alkaloid chanoclavine can be catalyzed by the two enzymes, Claviceps purpurea CpDmaW (SEQ ID NO: 5) and Aspergillus fumigatus FgaMT (SEQ ID NO: 6) that both are active in S. cerevisiae. The first enzyme, CpDmaW catalyses the joining of a Tryptophan and a DMAPP molecule to produce DMAT, and the second enzyme, FgaMT catalyses the subsequent methylation step that leads to Me-DMAT (see FIG. 3).

Measurements of DMAT and/or Me-DMAT were used to indirectly assess the accumulation of DMAPP in yeast strains that had a wild type ERG20 gene, or the KEX2 promoter in front of the ERG20 ORF or has the CYC1 promoter with stem-loop structure in the heterologous 5'UTR in front of the ERG20 ORF. The CpDmaW and FgaMT genes were cloned on a multicopy double expression plasmid (2µ) with CpDmaW under the control of the TEF1 promoter and the FgaMT under the control of the PGK1 promoter. This plasmid was transformed in wild type and the ERG20 engineered S. cerevisiae strains.

Yeast cultures were grown at 30° C. overnight and then used to inoculate 250 ml culture flasks containing 25 ml synthetic complete (SC) 2% medium at an OD600 of 0.1. The main cultures were grown for 72 hours at 30° C. The yeast culture supernatant was extracted with ethyl acetate and the extract used for quantification of DMAT and Met-DMAT by LC-MS.

Figure 4:
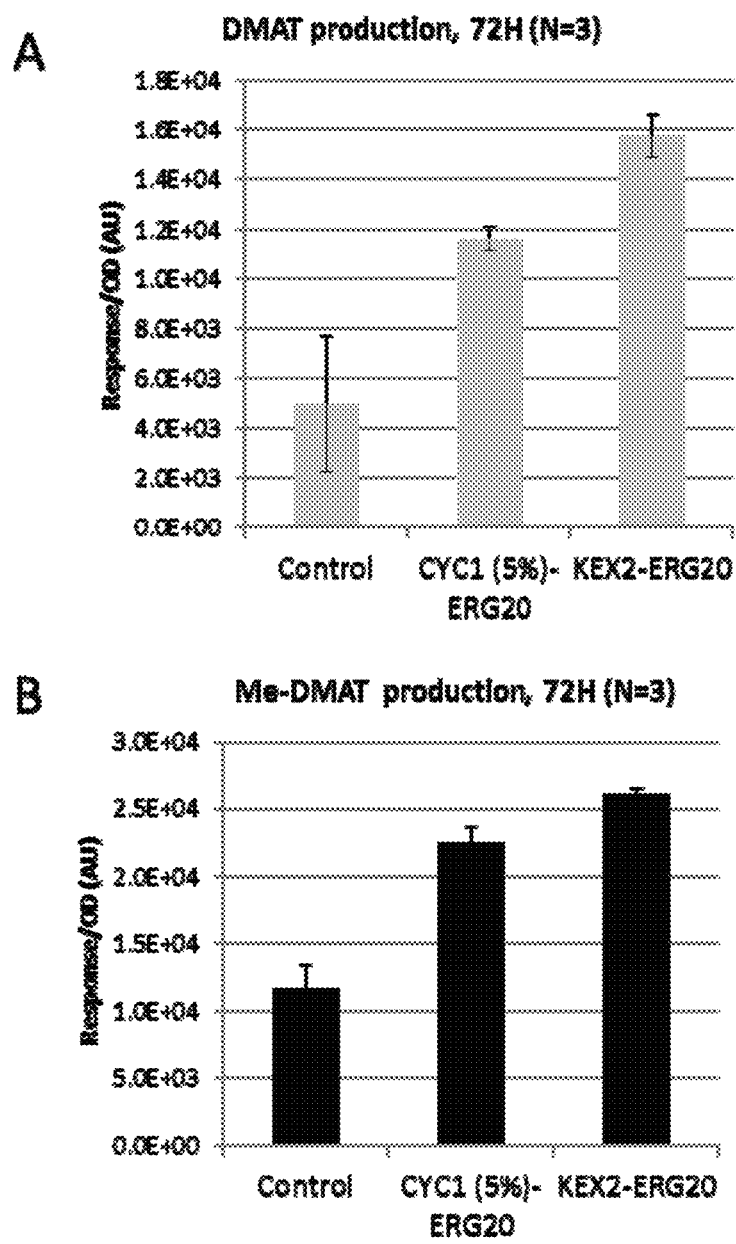
FIG. 4 DMAT and Me-DMAT production in yeast cells containing CYC1(5%)-ERG20 or KEX2-ERG20 compared to the wildtype strain.

The CYC1(5%)-ERG20 and the KEX2-ERG20 strain showed approximately 2-fold and 3-fold increase of DMAT accumulation after 72 hours compared to the unmodified control (see FIG. 4A). This represents an approximately 2-fold and 3-fold boosting of DMAPP levels. In all likelihood, this also reflects a similar accumulation of IPP since the isopentenyl-diphosphate delta isomerase 1 (IDI1) catalyses both the forward and reverse reaction between IPP and DMAPP.

The CYC1(5%)-ERG20 and the KEX2-ERG20 strain showed approximately 2-fold and 2.5-fold increase of Me-DMAT accumulation after 72 hours compared to the unmodified control strain (see FIG. 4B). This represents an approximately 2-fold and 2.5-fold boosting of DMAPP, and probably also a similar accumulation of IPP. The amount of DMAT and Me-DMAT was calculated per $OD_{600}$, thus providing an indication of the production per cell.

These measurements demonstrate that the DMAPP level can be increased several fold by exchanging the native ERG20 promoter for either a weak KEX2 promoter or a CYC1 promoter that introduces a stem-loop structure in the 5'UTR of the ERG20 transcript. The DMAPP and IPP accumulation can be exploited for increased production of GPP, FPP and GGPP when combined with a heterologous GPP synthase, or heterologous FPP synthase or heterologous GGPP synthase.

Example 3. Production of GPP

GPP production was indirectly determined by determining the level of Limonene in yeast strains expressing Limonene synthase 1. Limonene synthase 1 catalyses generation of Limonene from GPP and thus the level of limonene can in such yeast strains be used as an indirect measure of the level of GPP.

The yeast strains used in this example was the following:

A nucleic acid encoding truncated GPP synthase 2 from *Abies grandis* (derived from GPPS2 *Abies grandis*; SEQ ID NO: 12) under the control of the TEF1 promoter and a nucleic acid encoding truncated Limonene synthase 1 from *Citrus limon* (derived from LIMS1 *Citrus limon*; SEQ ID NO: 13) under the control of the PGK1p promoter were cloned on a single copy vector (ARS-CEN). The truncated GPPS2 sequence is derived from GPPS2 of *Abies grandis* (coded by GenBank accession number AF513112) from which amino acids 2-86 have been deleted to make the truncated tGPPS2. The truncated LIMS1 sequence is derived from LIMS from *Citrus limon* (coded by GenBank accession number Q8L5K3), from which amino acids 2-52 have been deleted to make the truncated tLIMS1

This plasmid was transformed into wild type *S. cerevisiae* (referred to as "WT+tGPPS+tLIMS") as well as into the KEX2-ERG20 *S. cerevisiae* strain prepared as described in Example 1 (referred to as "KEX2-ERG20+tGPPS+tLIMS") and into the CYC1(5%)-ERG20 *S. cerevisiae* strain prepared as described in Example 1 (referred to as "CYC1(5%)-ERG20+tGPPS+tLIMS").

Figure 8:
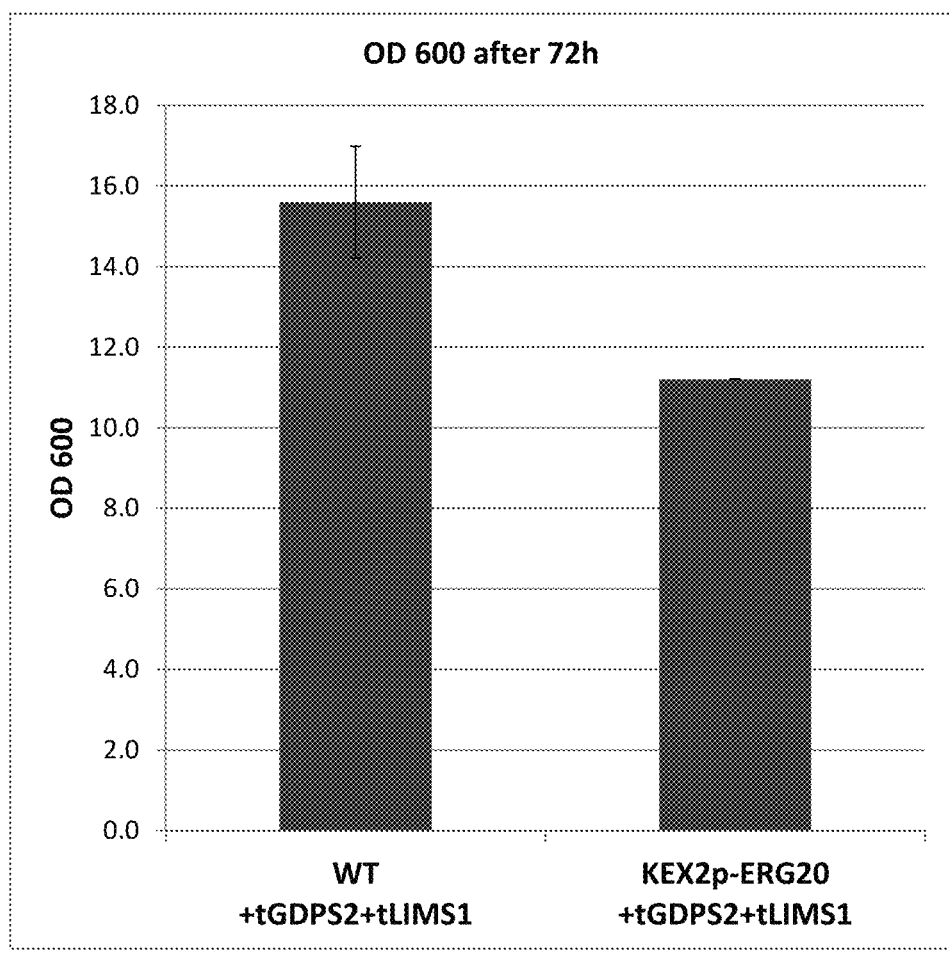
FIG. 8 shows the final $OD_{600}$ of the wild-type strain and the KEX2-ERG20+tGPPS+tLIMS strain. It shows that the modified strain grows well and to an $OD_{600}$ greater than 10.

Yeasts cultures were grown at 30° C. overnight and then used to inoculate 250 ml culture flasks containing 25 ml SC 2% medium at an OD600 of 0.1 supplemented with 10% Isopropyl myristate. The main cultures were grown for 72 hours at 30° C. The modified strain grows well and to an $OD_{600}$ greater than 10 (see FIG. 8). The limonene accumulated in the isopropyl myristate was quantified by GC-MS. The amount of limonene was calculated per $OD_{600}$, thus providing an indication of the production of limonene per cell.

Figure 5:
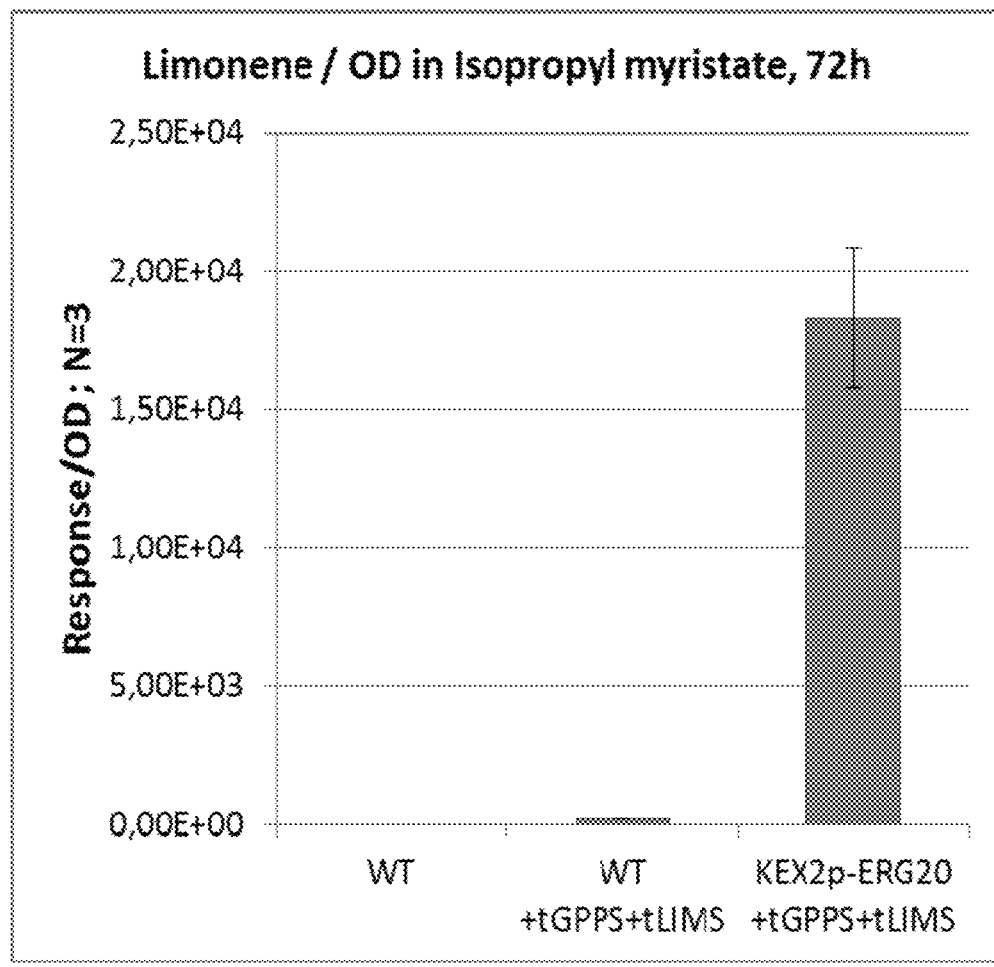
FIG. 5 shows levels of limonene expression determined in isopropyl myristate in the KEX2-ERG20 compared to the wildtype strain.

The KEX2-ERG20+tGPPS+tLIMS strain showed a surprising 80-100 fold increase of the limonene levels compared to the WT+tGPPS+tLIMS strain as shown in FIG. 5, which indicates a similar level of boosting the GPP level.

Boosting of the GPP levels was also obtained in CYC1 (5%)-ERG20+tGPPS+tLIMS, however to a lower level than in KEX2-ERG20+tGPPS+tLIMS.

Example 4

Native *E. faecalis* mvaE and mvaS sequences were synthesized and cloned as two independent expression cassettes under the control of the constitutive PGK1 and TEF1 promoters, respectively, on a single copy vector (ARS-CEN) to produce the mvaE/mvaS plasmid. The native *E. faecalis* mvaE encodes a polypeptide of SEQ ID NO: 9 and the native *E. faecalis* mvaS encodes a polypeptide of SEQ ID NO: 10. A nucleic acid encoding a truncated version of *S. cerevisiae* HMGR1 (tHMGR; derived from SEQ ID NO: 8) was PCR amplified from *S. cerevisiae* genomic DNA and cloned as an expression cassette under the control of the constitutive GPD1 promoter on a single copy vector (ARS-CEN) to produce the tHMGR plasmid. A yeast codon optimized *Artemisia annua* amorpha-4,11-diene synthase gene encoding the polypeptide of SEQ ID NO: 11 was synthesized and cloned as an expression cassette under the control of the constitutive PGK1 promoter on a multi copy vector (2μ) to produce the ADS plasmid. The ADS plasmid was transformed in yeast *S. cerevisiae* with either mvaE/mvaS, HMGR, or an empty control plasmid. The yeast strain that was used for the experiment has an ERG9 gene that is translationally downregulated by a stem-loop structure in the 5'UTR.

Figure 6:
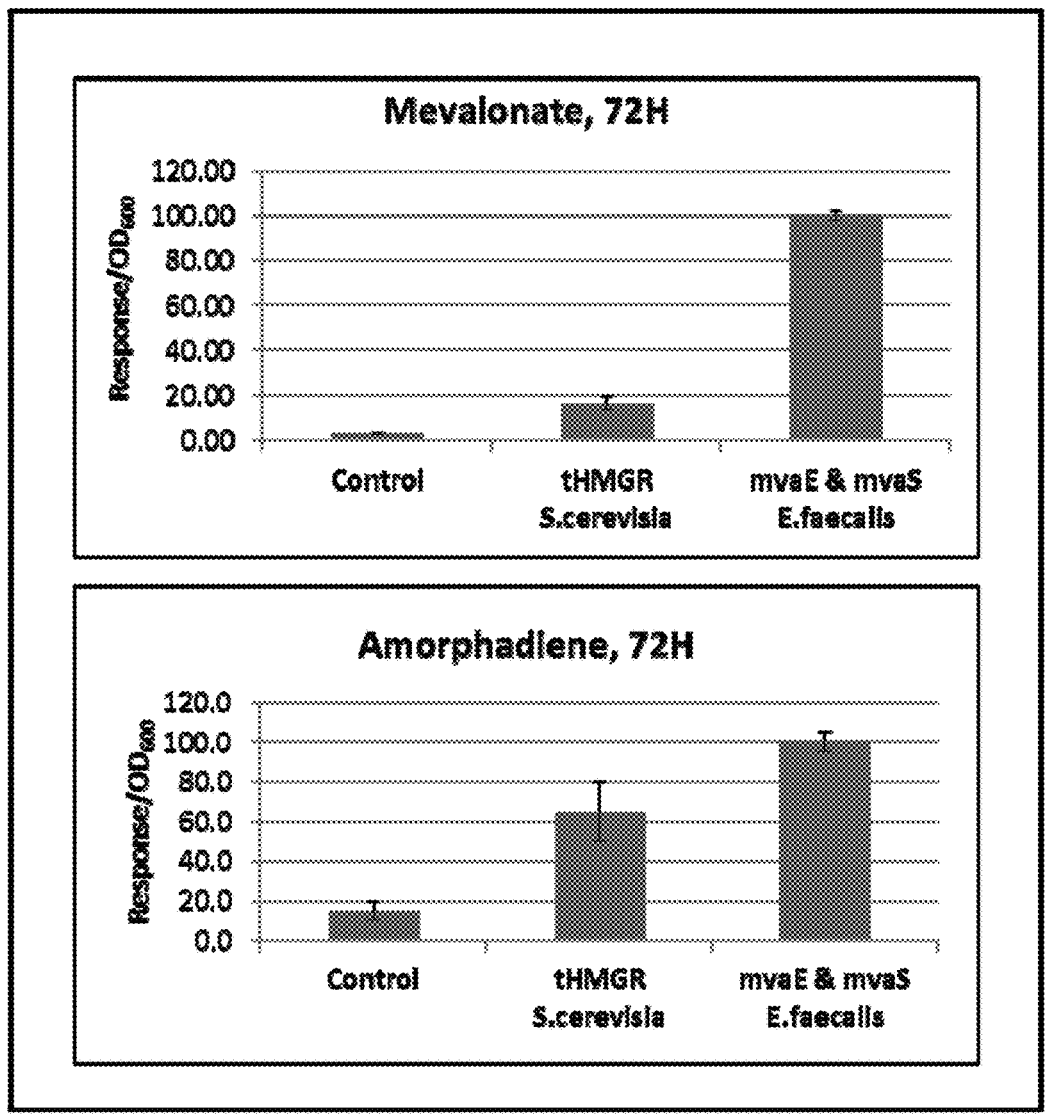
FIG. 6 shows levels of mevalonate (upper panel) and amorphadiene (lower panel) produced in yeast cells containing the ADS plasmid as well as a control plasmid, a truncated version of *S. cerevisiae* HMGR1 or mvaE and mvaS of *E. faecalis*.

Two ml yeast starter-cultures were grown at 30° C. overnight and used to inoculate 25 ml SC 2% glucose medium containing 10% dodecane in a 250 ml shake flask. Dodecane acts as a trapping agent for amorpha-4,11-diene. The cultures were grown for 72 hours at 30° C. The dodecane was separated from the yeast cells and culture supernatant by centrifugation and used directly for analysis in a gas chromatography-mass spectrometry system (GC-MS) to assess amorpha-4,11-diene production. To measure mevalonate levels, a small fraction of the yeast culture was treated with 2M HCl to convert mevalonate to mevanololactone. Next, the sample was extracted with ethylacetate followed by GC-MS analysis. The results are shown in FIG. 6.

mvaS can Rescue a Defective Mevalonate Pathway in *S. cerevisiae*

Figure 7:
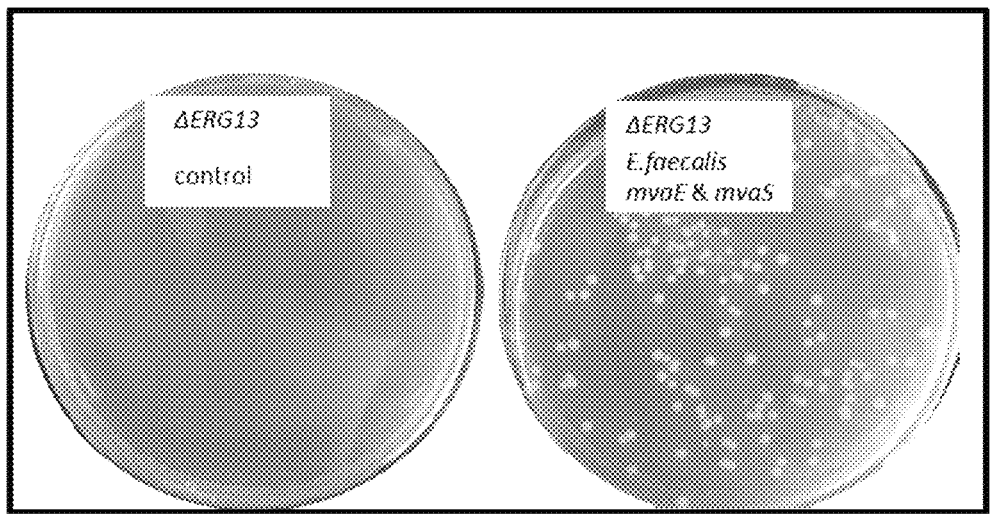
FIG. 7 shows growth of yeast cells having a deletion of ERG13 (left) and yeast cells having a deletion of ERG13, but also containing mvaE and mvaS of *E. faecalis* (right).

Deletion of ERG13 in *S. cerevisiae* leads to a defective mevalonate pathway. A ΔERG13 strain was produced by replacing the ERG13 gene with an expression cassette for the NatR gene that confers resistance to nourseothricin by homologous recombination. The deletion strain can only grow if the growth media is supplemented with mevalonate (10 mg/ml mevalonate). After transformation of the deletion strain with the mvaE/mvaS plasmid, the strain can grow without mevalonate supplement in the growth media, which demonstrates that the mvaS can functionally rescue the ERG13 deletion in *S. cerevisiae*. The results are shown in FIG. 7.

Example 5. Production of GGPP

GGPP production was indirectly determined by determining the level of ent-kaurene in yeast strains expressing FPPS, GGPPS, ent-Copalyl-diphospate synthase (CDPS) and ent-Kaurene synthase (KS). ent-Copalyl-diphospate synthase from *A. thaliana* was used (CDPS) the sequence of which is provided as (SEQ ID NO: 18). The ent-kaurene synthase of *A. thaliana* was used the sequence of which is provided as (SEQ ID NO: 17). ent-Copalyl-diphosphate synthase catalyses formation of ent-copalyl-PP from GGPP and ent-Kaurene synthase catalyses formation of ent-kaurene from ent-copalyl-pp. Thus, the level of ent-Kaurene can in such yeast strains be used as an indirect measure of the level of GGPP.

The yeast strains used in this example were the following:

A nucleic acid encoding truncated GPP synthase 2 from *S. cerevisiae* (BTS1; SEQ ID NO:23) under the control of the TEF1 promoter and a nucleic acid encoding FPP synthase from *Synechococcus* (SEQ ID NO:14) and a nucleic acid encoding CDPS from *A. thaliana* of SEQ ID NO: 18 under the control of the PGK1 promoter and KS of SEQ ID NO: 17 under the control of the TEF1 promoter were transformed into wild type *S. cerevisiae* (referred to as "WT+FPPS+BTS1+CDPS+KS") as well as into the KEX2-ERG20 *S. cerevisiae* strain prepared as described in Example 1 (referred to as "KEX2-ERG20+FPPS+BTS1+CDPS+KS").

Figure 9:
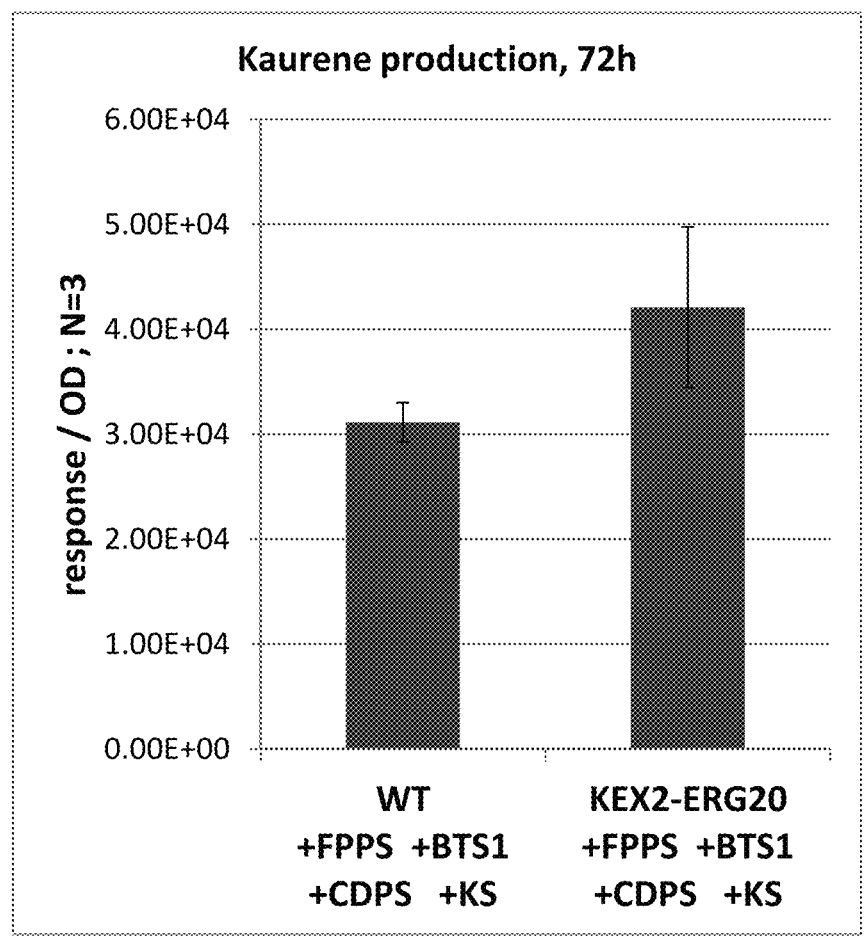
FIG. 9 shows levels of kaurene production determined in the wild-type strain and the KEX2-ERG20+FPPS+GPPS+CDPS+KS strain.

The presence of ent-kaurene was analysed in a gas chromatography-mass spectrometry system (GC-MS). The results are shown in FIG. 9.

REFERENCES

Hedl et al., J Bacteriol. 2002 April; 184(8):2116-22.
Suterlin et al., J Bacteriol. 2002 August; 184(15):4065-70.
Burg et al., Prog Lipid Res. 2011 October; 50(4):403-10. Epub 2011 Jul. 23.
Shalgi et al., Genome Biology. 2005 September; 6(10): Article R86.
Degenhardt et al., Phytochemistry 2009 70:1621-1637.
Wang & Dixon, Proc. Natl. Acad. Sci. USA 2009 106(24): 9914-19.
Bonitz et al., PLOS One 2011 6(11):E27336 pages 1-8.
Rico et al, *Appl Environ Microbiol.* 2010 October; 76(19): 6449-54.

The invention claimed is:

1. A method for producing a terpene or a terpenoid in a recombinant host cell, comprising culturing the recombinant host cell under conditions wherein the terpene or terpenoid is produced in the recombinant host cell, wherein the recombinant host cell is genetically engineered to produce reduced expression of an endogenous farnesyl diphosphate (FPP) synthase, an endogenous geranyl diphosphate (GPP) synthase or an endogenous enzyme having both FPP synthase and GPP synthase activity compared to a non-engineered host cell;

wherein reduced expression is produced in the recombinant host cell by:

(a) introducing into the recombinant host cell a heterologous genetic construct encoding the endogenous FPP synthase, the endogenous GPP synthase, or the endogenous enzyme having both FPP synthase and GPP synthase activity operably linked to an exogenous weak promoter, wherein the weak promoter is KEX2, PGK-1, GPD1, ADH1, ADH2, PYK1, TPi1, PDC1, TEF1, TEF2, FBA1, GAL1-10, CUP1, MET2, MET14, MET25, CYC1, GAL1-S, GAL1-L, TEF1, CAG, CMV, human UbiC, RSV, EF-1alpha, SV40, Mt1, Tet-On, Tet-Off, Mo-MLV-LTR, Mx1, progesterone, RU486 or Rapamycin-inducible promoter;

(b) introducing into the recombinant host cell a heterologous genetic construct encoding the endogenous FPP synthase, the endogenous GPP synthase, or the endogenous enzyme having both FPP synthase and GPP synthase activity operably linked to a messenger RNA destabilizing motif, comprising a M1 motif of SEQ ID NO:28 and/or a M24 motif of SEQ ID NO:29; or (c) introducing into the recombinant host cell a recombinant genetic construct, the construct comprising a gene encoding the endogenous FPP synthase, the endogenous GPP synthase, or the endogenous enzyme having both FPP synthase and GPP synthase activity operably linked to an endogenous promoter, wherein between the endogenous promoter and the gene encoding the endogenous FPP synthase, the endogenous GPP synthase, or the endogenous enzyme having both FPP synthase and GPP synthase activity is a heterologous insert sequence having the formula:

$-X_1-X_2-X_3-X_4-X_5-$;

wherein $X_2$ comprises at least 4 consecutive nucleotides being complementary to, and forming a hairpin secondary structure element with at least 4 consecutive nucleotides of $X_4$;

wherein $X_3$ either comprises zero nucleotides or one or more unpaired nucleotides forming a hairpin loop between $X_2$ and $X_4$;

wherein $X_4$ comprises at least 4 consecutive nucleotides being complementary to, and forming a hairpin secondary structure element with at least 4 consecutive nucleotides of $X_2$; and wherein $X_1$ and $X_5$ comprise zero, one or more nucleotides wherein the recombinant host cell further comprises one or more recombinant expression constructs encoding heterologous enzymes for producing said terpene or terpenoid; and wherein the recombinant host cell further comprises a recombinant expression construct encoding a truncated version of 3-hydroxy-3-methyl-glutaryl coenzyme A reductase (HMGR), comprising the catalytically active carboxyl terminal portion thereof, comprising a region from amino acid 619 to amino acid 1025 of SEQ ID NO:8 and having at least 90% sequence identity to the amino acid sequence set forth in SEQ ID NO:8.

2. The method of claim 1, wherein reduced expression is produced in the recombinant host cell by introducing into the recombinant host cell a heterologous genetic construct encoding the endogenous FPP synthase, the endogenous GPP synthase, or the endogenous enzyme having both FPP synthase and GPP synthase activity operably linked to an exogenous weak promoter, wherein the weak promoter is KEX2, PGK-1, GPD1, ADH1, ADH2, PYK1, TPi1, PDC1, TEF1, TEF2, FBA1, GAL1-10, CUP1, MET2, MET14, MET25, CYC1, GAL1-S, GAL1-L, TEF1, CAG, CMV, human UbiC, RSV, EF-1alpha, SV40, Mt1, Tet-On, Tet-Off, Mo-MLV-LTR, Mx1, progesterone, RU486 or Rapamycin-inducible promoter.

3. The method of claim 1, wherein reduced expression is produced in the recombinant host cell by introducing into the recombinant host cell a heterologous genetic construct encoding the endogenous FPP synthase, the endogenous GPP synthase, or the endogenous enzyme having both FPP synthase and GPP synthase activity operably linked to a messenger RNA destabilizing motif, comprising a M1 motif of SEQ ID NO:28 and/or a M24 motif of SEQ ID NO:29.

4. The method of claim 1, wherein reduced expression is produced in the recombinant host cell by introducing into the recombinant host cell a recombinant genetic construct, the construct comprising a gene encoding the endogenous FPP synthase, the endogenous GPP synthase, or the endogenous enzyme having both FPP synthase and GPP synthase activity operably linked to an endogenous promoter, wherein between the endogenous promoter and the gene encoding the endogenous FPP synthase, the endogenous GPP synthase, or the endogenous enzyme having both FPP synthase and GPP synthase activity is a heterologous insert sequence having the formula:

$-X_1-X_2-X_3-X_4-X_5-$;

wherein $X_2$ comprises at least 4 consecutive nucleotides being complementary to, and forming a hairpin secondary structure element with at least 4 consecutive nucleotides of $X_4$;

wherein $X_3$ either comprises zero nucleotides or one or more unpaired nucleotides forming a hairpin loop between $X_2$ and $X_4$;

wherein $X_4$ comprises at least 4 consecutive nucleotides being complementary to, and forming a hairpin secondary structure element with at least 4 consecutive nucleotides of $X_2$; and wherein $X_1$ and $X_5$ comprise zero, one or more nucleotides.

5. The method of claim 1, wherein the recombinant host cell further comprises a heterologous nucleic acid sequence encoding a dual function enzyme having at least 90% sequence identity to the amino acid sequence set forth in SEQ ID NO:9, wherein the dual function enzyme is an acetoacetyl-CoA thiolase and a HMGR.

6. The method of claim 1, wherein the recombinant host cell is a eukaryotic cell or a prokaryotic cell.

7. The method of claim 6, wherein the eukaryotic cell is a mammalian cell, a plant cell, a fungal cell or a yeast cell.

8. The method of claim 7, wherein the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii Arxula adeninivorans, Xanthophyllomyces dendrorhous*, or *Candida albicans* species.

9. The method of claim 8, wherein the yeast cell is a Saccharomycete.

10. The method of claim 8, wherein the yeast cell is a cell from the *Saccharomyces cerevisiae* species.

11. The method of claim 1, wherein the FPP synthase is yeast ERG20.

12. The method of claim 5, wherein the HMGR is a truncated HMGR, comprising the catalytically active carboxyl terminal portion thereof and having at least 90% sequence identity to the amino acid sequence set forth in SEQ ID NO:8.

13. The method of claim 1, wherein the terpene or the terpenoid is a monoterpene, a diterpene, a sesquiterpene, a triterpenoid or a tetraterpenoid.

14. The method of claim 13, wherein the monoterpene is a pinene, a myrcene or geraniol.

15. The method of claim 13, wherein the diterpene is geranylgeranyl pyrophosphate, retinol, retinal, phytol, taxol, forskolin or aphidicolin.

16. The method of claim 13, wherein the sesquiterpene is amorphadiene, patchoulol, santalol, longifolene or thujopsene.

17. The method of claim 13, wherein the triterpenoid is squalene.

18. The method of claim 13, wherein the tetraterpenoid is carotenoid.

* * * * *

SEQUENCE LISTING

```
<160> NUMBER OF SEQ ID NOS: 33

<210> SEQ ID NO 1
<211> LENGTH: 491
<212> TYPE: DNA
<213> ORGANISM: Artificial Sequence
<220> FEATURE:
<223> OTHER INFORMATION: KEX2 promoter

<400> SEQUENCE: 1
tcagcagctc tgatgtagat acacgtatct cgacatgttt tatttttact atacatacat    60
aaaagaaata aaaaatgata acgtgtatat tattattcat ataatcaatg agggtcattt   120
tctgaaacgc aaaaaacggt aaatggaaaa aaaataaaga tagaaaaaga aaacaaacaa   180
aggaaaggtt agcatattaa ataactgagc tgatacttca acagcatcgc tgaagagaac   240
agtattgaaa ccgaaacatt ttctaaaggc aaacaaggta ctccatattt gctggacgtg   300
ttctttctct cgtttcatat gcataattct gtcataagcc tgttcttttt cctggcttaa   360
acatcccgtt ttgtaaaaga gaaatctatt ccacatattt cattcattcg gctaccatac   420
taaggataaa ctaatcccgt tgttttttgg cctcgtcaca taattataaa ctactaaccc   480
attatcagaa g                                                        491

<210> SEQ ID NO 2
<211> LENGTH: 20
<212> TYPE: DNA
<213> ORGANISM: Artificial Sequence
<220> FEATURE:
<223> OTHER INFORMATION: Hairpin sequence

<400> SEQUENCE: 2
tgaattcgtt aacgaattca                                                20

<210> SEQ ID NO 3
<211> LENGTH: 306
<212> TYPE: DNA
<213> ORGANISM: Artificial Sequence
<220> FEATURE:
<223> OTHER INFORMATION: CYC1 promoter with stemloop sequence

<400> SEQUENCE: 3
cgttggttgg tggatcaagc ccacgcgtag gcaatcctcg agcagatccg ccaggcgtgt    60
atatatagcg tggatggcca ggcaacttta gtgctgacac atacaggcat atatatgt    120 gtgcgacgac acatgatcat atggcatgca tgtgctctgt atgtatataa aactcttgtt   180
```

```
ttcttctttt ctctaaatat tctttcctta tacattagga cctttgcagc ataaattact    240
atacttctat agacacacaa acacaaatac acacactaaa ttaatatgaa ttcgttaacg    300
aattca                                                               306
```

<210> SEQ ID NO 4
<211> LENGTH: 352
<212> TYPE: PRT
<213> ORGANISM: Saccharomyces cerevisiae

<400> SEQUENCE: 4

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

```
<210> SEQ ID NO 5
<211> LENGTH: 448
<212> TYPE: PRT
<213> ORGANISM: Claviceps purpurea

<400> SEQUENCE: 5
```

| | | | | | | | | | | | | | | |
|---|---|---|---|---|---|---|---|---|---|---|---|---|---|---|
| Met | Ser | Thr | Ala | Lys | Asp | Pro | Gly | Asn | Gly | Val | Tyr | Glu | Ile | Leu | Ser |
| 1 | | | | 5 | | | | | 10 | | | | | 15 | |

| Leu | Ile | Phe | Asp | Phe | Pro | Ser | Asn | Glu | Gln | Arg | Leu | Trp | Trp | His | Ser |
|---|---|---|---|---|---|---|---|---|---|---|---|---|---|---|---|
| | | | 20 | | | | | 25 | | | | | 30 | | |

| Thr | Ala | Pro | Met | Phe | Ala | Ala | Met | Leu | Asp | Asn | Ala | Gly | Tyr | Asn | Ile |
|---|---|---|---|---|---|---|---|---|---|---|---|---|---|---|---|
| | | 35 | | | | | 40 | | | | | 45 | | | |

| His | Asp | Gln | Tyr | Arg | His | Leu | Gly | Ile | Phe | Lys | Lys | His | Ile | Ile | Pro |
|---|---|---|---|---|---|---|---|---|---|---|---|---|---|---|---|
| | 50 | | | | | 55 | | | | | 60 | | | | |

| Phe | Leu | Gly | Val | Tyr | Pro | Thr | Lys | Asp | Lys | Glu | Arg | Trp | Leu | Ser | Ile |
|---|---|---|---|---|---|---|---|---|---|---|---|---|---|---|---|
| 65 | | | | | 70 | | | | | 75 | | | | | 80 |

| Leu | Thr | Arg | Cys | Gly | Leu | Pro | Leu | Glu | Leu | Ser | Leu | Asn | Cys | Thr | Asp |
|---|---|---|---|---|---|---|---|---|---|---|---|---|---|---|---|
| | | | | 85 | | | | | 90 | | | | | 95 | |

| Ser | Val | Val | Arg | Tyr | Thr | Tyr | Glu | Pro | Ile | Asn | Glu | Val | Thr | Gly | Thr |
|---|---|---|---|---|---|---|---|---|---|---|---|---|---|---|---|
| | | | 100 | | | | | 105 | | | | | 110 | | |

| Glu | Lys | Asp | Thr | Phe | Asn | Thr | Leu | Ala | Ile | Met | Thr | Ser | Val | Gln | Lys |
|---|---|---|---|---|---|---|---|---|---|---|---|---|---|---|---|
| | | 115 | | | | | 120 | | | | | 125 | | | |

| Leu | Ala | Gln | Ile | Gln | Ala | Gly | Ile | Asp | Leu | Glu | Trp | Phe | Ser | Tyr | Phe |
|---|---|---|---|---|---|---|---|---|---|---|---|---|---|---|---|
| | 130 | | | | | 135 | | | | | 140 | | | | |

| Lys | Asp | Glu | Leu | Thr | Leu | Asp | Glu | Ser | Glu | Ser | Ala | Thr | Leu | Gln | Ser |
|---|---|---|---|---|---|---|---|---|---|---|---|---|---|---|---|
| 145 | | | | | 150 | | | | | 155 | | | | | 160 |

| Asn | Glu | Leu | Val | Lys | Glu | Gln | Ile | Lys | Thr | Gln | Asn | Lys | Leu | Ala | Leu |
|---|---|---|---|---|---|---|---|---|---|---|---|---|---|---|---|
| | | | | 165 | | | | | 170 | | | | | 175 | |

| Asp | Leu | Lys | Glu | Ser | Gln | Phe | Ala | Leu | Lys | Val | Tyr | Phe | Tyr | Pro | His |
|---|---|---|---|---|---|---|---|---|---|---|---|---|---|---|---|
| | | | 180 | | | | | 185 | | | | | 190 | | |

| Leu | Lys | Ser | Ile | Ala | Thr | Gly | Lys | Ser | Thr | His | Asp | Leu | Ile | Phe | Asp |
|---|---|---|---|---|---|---|---|---|---|---|---|---|---|---|---|
| | | 195 | | | | | 200 | | | | | 205 | | | |

| Ser | Val | Leu | Lys | Leu | Ser | Gln | Lys | His | Asp | Ser | Ile | Gln | Pro | Ala | Phe |
|---|---|---|---|---|---|---|---|---|---|---|---|---|---|---|---|
| | 210 | | | | | 215 | | | | | 220 | | | | |

| Gln | Val | Leu | Cys | Asp | Tyr | Val | Ser | Arg | Arg | Asn | His | Ser | Ala | Glu | Val |
|---|---|---|---|---|---|---|---|---|---|---|---|---|---|---|---|
| 225 | | | | | 230 | | | | | 235 | | | | | 240 |

| Asp | Gln | His | Gly | Ala | Leu | His | Ala | Arg | Leu | Leu | Ser | Cys | Asp | Leu | Ile |
|---|---|---|---|---|---|---|---|---|---|---|---|---|---|---|---|
| | | | | 245 | | | | | 250 | | | | | 255 | |

| Asp | Pro | Ala | Lys | Ser | Arg | Val | Lys | Ile | Tyr | Leu | Leu | Glu | Lys | Thr | Val |
|---|---|---|---|---|---|---|---|---|---|---|---|---|---|---|---|
| | | | 260 | | | | | 265 | | | | | 270 | | |

| Ser | Leu | Ser | Val | Met | Glu | Asp | Leu | Trp | Thr | Leu | Gly | Gly | Gln | Arg | Val |
|---|---|---|---|---|---|---|---|---|---|---|---|---|---|---|---|
| | | 275 | | | | | 280 | | | | | 285 | | | |

| Asp | Ala | Ser | Thr | Met | Asp | Gly | Leu | Asp | Met | Leu | Arg | Glu | Leu | Trp | Ser |
|---|---|---|---|---|---|---|---|---|---|---|---|---|---|---|---|
| | 290 | | | | | 295 | | | | | 300 | | | | |

| Leu | Leu | Lys | Val | Pro | Thr | Gly | His | Leu | Glu | Tyr | Pro | Lys | Gly | Tyr | Leu |
|---|---|---|---|---|---|---|---|---|---|---|---|---|---|---|---|
| 305 | | | | | 310 | | | | | 315 | | | | | 320 |

| Glu | Leu | Gly | Glu | Ile | Pro | Asn | Glu | Gln | Leu | Pro | Ser | Met | Ala | Asn | Tyr |
|---|---|---|---|---|---|---|---|---|---|---|---|---|---|---|---|
| | | | | 325 | | | | | 330 | | | | | 335 | |

| Thr | Leu | His | His | Asn | Asp | Pro | Met | Pro | Glu | Pro | Gln | Val | Tyr | Phe | Thr |
|---|---|---|---|---|---|---|---|---|---|---|---|---|---|---|---|
| | | | 340 | | | | | 345 | | | | | 350 | | |

| Val | Phe | Gly | Met | Asn | Asp | Ala | Glu | Ile | Ser | Asn | Ala | Leu | Thr | Ile | Phe |
|---|---|---|---|---|---|---|---|---|---|---|---|---|---|---|---|
| | | 355 | | | | | 360 | | | | | 365 | | | |

| Phe | Gln | Arg | His | Gly | Phe | Asp | Asp | Met | Ala | Lys | Asn | Tyr | Arg | Val | Phe |
|---|---|---|---|---|---|---|---|---|---|---|---|---|---|---|---|
| | 370 | | | | | 375 | | | | | 380 | | | | |

-continued

Leu Gln Asp Ser Tyr Pro Tyr His Asp Phe Glu Ser Leu Asn Tyr Leu
385                 390                 395                 400

His Ala Tyr Ile Ser Phe Ser Tyr Arg Arg Asn Lys Pro Tyr Leu Ser
            405                 410                 415

Val Tyr Leu His Thr Phe Glu Thr Gly Arg Trp Pro Val Phe Ala Asp
        420                 425                 430

Ser Pro Ile Ser Phe Asp Ala Tyr Arg Arg Cys Glu Leu Ser Thr Lys
            435                 440                 445

<210> SEQ ID NO 6
<211> LENGTH: 339
<212> TYPE: PRT
<213> ORGANISM: Aspergillus fumigatus

<400> SEQUENCE: 6

Met Thr Ile Ser Ala Pro Pro Ile Ile Asp Ile Arg Gln Ala Gly Leu
1               5                   10                  15

Glu Ser Ser Ile Pro Asp Gln Val Val Glu Gly Leu Thr Lys Glu Val
            20                  25                  30

Lys Thr Leu Pro Ala Leu Leu Phe Tyr Ser Thr Lys Gly Ile Gln His
        35                  40                  45

Trp Asn Arg His Ser His Ala Ala Asp Phe Tyr Pro Arg His Glu Glu
    50                  55                  60

Leu Cys Ile Leu Lys Ala Glu Ala Ser Lys Met Ala Ala Ser Ile Ala
65                  70                  75                  80

Gln Asp Ser Leu Val Ile Asp Met Gly Ser Ala Ser Met Asp Lys Val
                85                  90                  95

Ile Leu Leu Leu Glu Ala Leu Glu Glu Gln Lys Lys Ser Ile Thr Tyr
            100                 105                 110

Tyr Ala Leu Asp Leu Ser Tyr Ser Glu Leu Ala Ser Asn Phe Gln Ala
        115                 120                 125

Ile Pro Val Asp Arg Phe His Tyr Val Arg Phe Ala Ala Leu His Gly
    130                 135                 140

Thr Phe Asp Asp Gly Leu His Trp Leu Gln Asn Ala Pro Asp Ile Arg
145                 150                 155                 160

Asn Arg Pro Arg Cys Ile Leu Leu Phe Gly Leu Thr Ile Gly Asn Phe
                165                 170                 175

Ser Arg Asp Asn Ala Ala Ser Phe Leu Arg Asn Ile Ala Gln Ser Ala
            180                 185                 190

Leu Ser Thr Ser Pro Thr Gln Ser Ser Ile Ile Val Ser Leu Asp Ser
        195                 200                 205

Cys Lys Leu Pro Thr Lys Ile Leu Arg Ala Tyr Thr Ala Asp Gly Val
    210                 215                 220

Val Pro Phe Ala Leu Ala Ser Leu Ser Tyr Ala Asn Ser Leu Phe His
225                 230                 235                 240

Pro Lys Gly Asp Arg Lys Ile Phe Asn Glu Glu Asp Trp Tyr Phe His
                245                 250                 255

Ser Glu Trp Asn His Ala Leu Gly Arg His Glu Ala Ser Leu Ile Thr
            260                 265                 270

Gln Ser Lys Asp Ile Gln Leu Gly Ala Pro Leu Glu Thr Val Ile Val
        275                 280                 285

Arg Arg Asp Glu Lys Ile Arg Phe Gly Cys Ser Tyr Lys Tyr Asp Lys
    290                 295                 300

Ala Glu Arg Asp Gln Leu Phe His Ser Ala Gly Leu Glu Asp Ala Ala
305                 310                 315                 320

```
Val Trp Thr Ala Pro Asp Cys Asp Val Ala Phe Tyr Gln Leu Arg Leu
            325                 330                 335

Arg Leu Asn

<210> SEQ ID NO 7
<211> LENGTH: 330
<212> TYPE: PRT
<213> ORGANISM: Sulfobacillus acidophilus

<400> SEQUENCE: 7

Met Ser Tyr Phe Asp Asn Tyr Phe Asn Glu Ile Val Asn Ser Val Asn
1               5                   10                  15

Asp Ile Ile Lys Ser Tyr Ile Ser Gly Asp Val Pro Lys Leu Tyr Glu
            20                  25                  30

Ala Ser Tyr His Leu Phe Thr Ser Gly Gly Lys Arg Leu Arg Pro Leu
        35                  40                  45

Ile Leu Thr Ile Ser Ser Asp Leu Phe Gly Gly Gln Arg Glu Arg Ala
    50                  55                  60

Tyr Tyr Ala Gly Ala Ala Ile Glu Val Leu His Thr Phe Thr Leu Val
65                  70                  75                  80

His Asp Asp Ile Met Asp Gln Asp Asn Ile Arg Arg Gly Leu Pro Thr
                85                  90                  95

Val His Val Lys Tyr Gly Leu Pro Leu Ala Ile Leu Ala Gly Asp Leu
            100                 105                 110

Leu His Ala Lys Ala Phe Gln Leu Leu Thr Gln Ala Leu Arg Gly Leu
        115                 120                 125

Pro Ser Glu Thr Ile Ile Lys Ala Phe Asp Ile Phe Thr Arg Ser Ile
    130                 135                 140

Ile Ile Ser Glu Gly Gln Ala Val Asp Met Glu Phe Glu Asp Arg
145                 150                 155                 160

Ile Asp Ile Lys Glu Gln Glu Tyr Leu Asp Met Ile Ser Arg Lys Thr
                165                 170                 175

Ala Ala Leu Phe Ser Ala Ser Ser Ile Gly Ala Leu Ile Ala Gly
            180                 185                 190

Ala Asn Asp Asn Asp Val Arg Leu Met Ser Asp Phe Gly Thr Asn Leu
        195                 200                 205

Gly Ile Ala Phe Gln Ile Val Asp Asp Ile Leu Gly Leu Thr Ala Asp
    210                 215                 220

Glu Lys Glu Leu Gly Lys Pro Val Phe Ser Asp Ile Arg Glu Gly Lys
225                 230                 235                 240

Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
        275                 280                 285

Ala Tyr Asn Leu Ala Glu Lys Tyr Tyr Lys Asn Ala Ile Asp Ser Leu
    290                 295                 300

Asn Gln Val Ser Ser Lys Ser Asp Ile Pro Gly Lys Ala Leu Lys Tyr
305                 310                 315                 320

Leu Ala Glu Phe Thr Ile Arg Arg Lys
                325                 330
<210> SEQ ID NO 8
<211> LENGTH: 1054
<212> TYPE: PRT
<213> ORGANISM: Saccharomyces cerevisiae
```

```
<400> SEQUENCE: 8

Met Pro Pro Leu Phe Lys Gly Leu Lys Gln Met Ala Lys Pro Ile Ala
1               5                   10                  15

Tyr Val Ser Arg Phe Ser Ala Lys Arg Pro Ile His Ile Ile Leu Phe
            20                  25                  30

Ser Leu Ile Ile Ser Ala Phe Ala Tyr Leu Ser Val Ile Gln Tyr Tyr
        35                  40                  45

Phe Asn Gly Trp Gln Leu Asp Ser Asn Ser Val Phe Glu Thr Ala Pro
    50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125

Glu Lys Asp Asn Thr Lys Tyr Ile Leu Gln Glu Asp Leu Ser Val Ser
    130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
        195                 200                 205

Asn Asp Met Arg Lys Thr Gly Ser Asn Phe Trp Leu Ser Ala Ser Thr
    210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Glu Gly Leu
                245                 250                 255

Pro Phe Ile Val Val Val Gly Phe Lys His Lys Ile Lys Ile Ala
            260                 265                 270

Gln Tyr Ala Leu Glu Lys Phe Glu Arg Val Gly Leu Ser Lys Arg Ile
        275                 280                 285

Thr Thr Asp Glu Ile Val Phe Glu Ser Val Ser Glu Glu Gly Gly Arg
    290                 295                 300

Leu Ile Gln Asp His Leu Leu Cys Ile Phe Ala Phe Ile Gly Cys Ser
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
        355                 360                 365

Ile Ile Lys Gln Thr Leu Glu Glu Asp Gly Val Val Pro Ser Thr Ala
    370                 375                 380

Arg Ile Ile Ser Lys Ala Glu Lys Ser Val Ser Ser Phe Leu Asn
385                 390                 395                 400

Leu Ser Val Val Val Ile Ile Met Lys Leu Ser Val Ile Leu Leu Phe
                405                 410                 415
```

-continued

```
Val Phe Ile Asn Phe Tyr Asn Phe Gly Ala Asn Trp Val Asn Asp Ala
                420                 425                 430
Phe Asn Ser Leu Tyr Phe Asp Lys Glu Arg Val Ser Leu Pro Asp Phe
            435                 440                 445
Ile Thr Ser Asn Ala Ser Glu Asn Phe Lys Glu Gln Ala Ile Val Ser
        450                 455                 460
Val Thr Pro Leu Leu Tyr Tyr Lys Pro Ile Lys Ser Tyr Gln Arg Ile
465                 470                 475                 480
Glu Asp Met Val Leu Leu Leu Arg Asn Val Ser Val Ala Ile Arg
                485                 490                 495
Asp Arg Phe Val Ser Lys Leu Val Leu Ser Ala Leu Val Cys Ser Ala
            500                 505                 510
Val Ile Asn Val Tyr Leu Leu Asn Ala Ala Arg Ile His Thr Ser Tyr
        515                 520                 525
Thr Ala Asp Gln Leu Val Lys Thr Glu Val Thr Lys Lys Ser Phe Thr
    530                 535                 540
Ala Pro Val Gln Lys Ala Ser Thr Pro Val Leu Thr Asn Lys Thr Val
545                 550                 555                 560
Ile Ser Gly Ser Lys Val Lys Ser Leu Ser Ser Ala Gln Ser Ser Ser
                565                 570                 575
Ser Gly Pro Ser Ser Ser Ser Glu Glu Asp Asp Ser Arg Asp Ile Glu
            580                 585                 590
Ser Leu Asp Lys Lys Ile Arg Pro Leu Glu Glu Leu Glu Ala Leu Leu
        595                 600                 605
Ser Ser Gly Asn Thr Lys Gln Leu Lys Asn Lys Glu Val Ala Ala Leu
    610                 615                 620
Val Ile His Gly Lys Leu Pro Leu Tyr Ala Leu Glu Lys Lys Leu Gly
625                 630                 635                 640
Asp Thr Thr Arg Ala Val Ala Val Arg Lys Ala Leu Ser Ile Leu
                645                 650                 655
Ala Glu Ala Pro Val Leu Ala Ser Asp Arg Leu Pro Tyr Lys Asn Tyr
            660                 665                 670
Asp Tyr Asp Arg Val Phe Gly Ala Cys Cys Glu Asn Val Ile Gly Tyr
        675                 680                 685
Met Pro Leu Pro Val Gly Val Ile Gly Pro Leu Val Ile Asp Gly Thr
    690                 695                 700
Ser Tyr His Ile Pro Met Ala Thr Thr Glu Gly Cys Leu Val Ala Ser
705                 710                 715                 720
Ala Met Arg Gly Cys Lys Ala Ile Asn Ala Gly Gly Gly Ala Thr Thr
                725                 730                 735
Val Leu Thr Lys Asp Gly Met Thr Arg Gly Pro Val Val Arg Phe Pro
            740                 745                 750
Thr Leu Lys Arg Ser Gly Ala Cys Lys Ile Trp Leu Asp Ser Glu Glu
        755                 760                 765
Gly Gln Asn Ala Ile Lys Lys Ala Phe Asn Ser Thr Ser Arg Phe Ala
    770                 775                 780
Arg Leu Gln His Ile Gln Thr Cys Leu Ala Gly Asp Leu Leu Phe Met
785                 790                 795                 800
Arg Phe Arg Thr Thr Thr Gly Asp Ala Met Gly Met Asn Met Ile Ser
                805                 810                 815
Lys Gly Val Glu Tyr Ser Leu Lys Gln Met Val Glu Glu Tyr Gly Trp
            820                 825                 830
```

-continued

Glu Asp Met Glu Val Val Ser Val Ser Gly Asn Tyr Cys Thr Asp Lys
        835                 840                 845

Lys Pro Ala Ala Ile Asn Trp Ile Glu Gly Arg Gly Lys Ser Val Val
850                 855                 860

Ala Glu Ala Thr Ile Pro Gly Asp Val Arg Lys Val Leu Lys Ser
865                 870                 875                 880

Asp Val Ser Ala Leu Val Glu Leu Asn Ile Ala Lys Asn Leu Val Gly
            885                 890                 895

Ser Ala Met Ala Gly Ser Val Gly Gly Phe Asn Ala His Ala Ala Asn
                900                 905                 910

Leu Val Thr Ala Val Phe Leu Ala Leu Gly Gln Asp Pro Ala Gln Asn
            915                 920                 925

Val Glu Ser Ser Asn Cys Ile Thr Leu Met Lys Glu Val Asp Gly Asp
        930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
            980                 985                 990

Ala Arg Ile Val Ala Cys Ala Val  Leu Ala Gly Glu Leu  Ser Leu Cys
        995                 1000                1005

Ala Ala  Leu Ala Ala Gly His  Leu Val Gln Ser His  Met Thr His
        1010                1015                1020

Asn Arg Lys Pro Ala Glu Pro  Thr Lys Pro Asn Asn  Leu Asp Ala
        1025                1030                1035

Thr Asp  Ile Asn Arg Leu Lys  Asp Gly Ser Val Thr  Cys Ile Lys
        1040                1045                1050

Ser

<210> SEQ ID NO 9
<211> LENGTH: 803
<212> TYPE: PRT
<213> ORGANISM: Enterococcus faecalis

<400> SEQUENCE: 9

Met Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
            100                 105                 110

Gly Gly Ile Glu Asn Met Ser Gln Ala Pro Lys Leu Gln Arg Phe Asn
        115                 120                 125

Tyr Glu Thr Glu Ser Tyr Asp Ala Pro Phe Ser Ser Met Met Tyr Asp
    130                 135                 140

-continued

```
Gly Leu Thr Asp Ala Phe Ser Gly Gln Ala Met Gly Leu Thr Ala Glu
145                 150                 155                 160
Asn Val Ala Glu Lys Tyr His Val Thr Arg Glu Glu Asp Gln Phe
            165                 170                 175
Ser Val His Ser Gln Leu Lys Ala Ala Gln Ala Gln Ala Glu Gly Ile
            180                 185                 190
Phe Ala Asp Glu Ile Ala Pro Leu Glu Val Ser Gly Thr Leu Val Glu
            195                 200                 205
Lys Asp Glu Gly Ile Arg Pro Asn Ser Ser Val Glu Lys Leu Gly Thr
    210                 215                 220
Leu Lys Thr Val Phe Lys Glu Asp Gly Thr Val Thr Ala Gly Asn Ala
225                 230                 235                 240
Ser Thr Ile Asn Asp Gly Ala Ser Ala Leu Ile Ile Ala Ser Gln Glu
                245                 250                 255
Tyr Ala Glu Ala His Gly Leu Pro Tyr Leu Ala Ile Ile Arg Asp Ser
            260                 265                 270
Val Glu Val Gly Ile Asp Pro Ala Tyr Met Gly Ile Ser Pro Ile Lys
            275                 280                 285
Ala Ile Gln Lys Leu Leu Ala Arg Asn Gln Leu Thr Thr Glu Glu Ile
    290                 295                 300
Asp Leu Tyr Glu Ile Asn Glu Ala Phe Ala Ala Thr Ser Ile Val Val
305                 310                 315                 320
Gln Arg Glu Leu Ala Leu Pro Glu Glu Lys Val Asn Ile Tyr Gly Gly
                325                 330                 335
Gly Ile Ser Leu Gly His Ala Ile Gly Ala Thr Gly Ala Arg Leu Leu
            340                 345                 350
Thr Ser Leu Ser Tyr Gln Leu Asn Gln Lys Glu Lys Lys Tyr Gly Val
            355                 360                 365
Ala Ser Leu Cys Ile Gly Gly Gly Leu Gly Leu Ala Met Leu Leu Glu
    370                 375                 380
Arg Pro Gln Gln Lys Lys Asn Ser Arg Phe Tyr Gln Met Ser Pro Glu
385                 390                 395                 400
Glu Arg Leu Ala Ser Leu Leu Asn Glu Gly Gln Ile Ser Ala Asp Thr
                405                 410                 415
Lys Lys Glu Phe Glu Asn Thr Ala Leu Ser Ser Gln Ile Ala Asn His
            420                 425                 430
Met Ile Glu Asn Gln Ile Ser Glu Thr Glu Val Pro Met Gly Val Gly
            435                 440                 445
Leu His Leu Thr Val Asp Glu Thr Asp Tyr Leu Val Pro Met Ala Thr
    450                 455                 460
Glu Glu Pro Ser Val Ile Ala Ala Leu Ser Asn Gly Ala Lys Ile Ala
465                 470                 475                 480
Gln Gly Phe Lys Thr Val Asn Gln Gln Arg Leu Met Arg Gly Gln Ile
                485                 490                 495
Val Phe Tyr Asp Val Ala Asp Ala Glu Ser Leu Ile Asp Glu Leu Gln
            500                 505                 510
Val Arg Glu Thr Glu Ile Phe Gln Gln Ala Glu Leu Ser Tyr Pro Ser
            515                 520                 525
Ile Val Lys Arg Gly Gly Gly Leu Arg Asp Leu Gln Tyr Arg Ala Phe
    530                 535                 540
Asp Glu Ser Phe Val Ser Val Asp Phe Leu Val Asp Val Lys Asp Ala
545                 550                 555                 560
```

Met Gly Ala Asn Ile Val Asn Ala Met Leu Glu Gly Val Ala Glu Leu
            565                 570                 575

Phe Arg Glu Trp Phe Ala Glu Gln Lys Ile Leu Phe Ser Ile Leu Ser
        580                 585                 590

Asn Tyr Ala Thr Glu Ser Val Val Thr Met Lys Thr Ala Ile Pro Val
    595                 600                 605

Ser Arg Leu Ser Lys Gly Ser Asn Gly Arg Glu Ile Ala Glu Lys Ile
610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
            645                 650                 655

Gly Asn Asp Thr Arg Ala Val Ser Ala Ser Cys His Ala Phe Ala Val
        660                 665                 670

Lys Glu Gly Arg Tyr Gln Gly Leu Thr Ser Trp Thr Leu Asp Gly Glu
    675                 680                 685

Gln Leu Ile Gly Glu Ile Ser Val Pro Leu Ala Leu Ala Thr Val Gly
690                 695                 700

Gly Ala Thr Lys Val Leu Pro Lys Ser Gln Ala Ala Ala Asp Leu Leu
705                 710                 715                 720

Ala Val Thr Asp Ala Lys Glu Leu Ser Arg Val Val Ala Ala Val Gly
            725                 730                 735

Leu Ala Gln Asn Leu Ala Ala Leu Arg Ala Leu Val Ser Glu Gly Ile
        740                 745                 750

Gln Lys Gly His Met Ala Leu Gln Ala Arg Ser Leu Ala Met Thr Val
    755                 760                 765

Gly Ala Thr Gly Lys Glu Val Glu Ala Val Ala Gln Gln Leu Lys Arg
770                 775                 780

Gln Lys Thr Met Asn Gln Asp Arg Ala Leu Ala Ile Leu Asn Asp Leu
785                 790                 795                 800

Arg Lys Gln

<210> SEQ ID NO 10
<211> LENGTH: 383
<212> TYPE: PRT
<213> ORGANISM: Enterococcus faecalis

<400> SEQUENCE: 10

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
            85                  90                  95

Gly Ile Gln Pro Phe Ala Arg Ser Phe Glu Ile Lys Glu Ala Cys Tyr
        100                 105                 110

Gly Ala Thr Ala Gly Leu Gln Leu Ala Lys Asn His Val Ala Leu His
    115                 120                 125

```
Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
            340                 345                 350

Glu Thr Leu Asp Thr Asp Ile Asp Gln Thr Leu Glu Asp Glu Leu Lys
        355                 360                 365

Tyr Ser Ile Ser Ala Ile Asn Asn Thr Val Arg Ser Tyr Arg Asn
    370                 375                 380

<210> SEQ ID NO 11
<211> LENGTH: 546
<212> TYPE: PRT
<213> ORGANISM: Artemisia annua

<400> SEQUENCE: 11

Met Ser Leu Thr Glu Glu Lys Pro Ile Arg Pro Ile Ala Asn Phe Pro
1               5                   10                  15

Pro Ser Ile Trp Gly Asp Gln Phe Leu Ile Tyr Glu Lys Gln Val Glu
            20                  25                  30

Gln Gly Val Glu Gln Ile Val Asn Asp Leu Lys Lys Glu Val Arg Gln
        35                  40                  45

Leu Leu Lys Glu Ala Leu Asp Ile Pro Met Lys His Ala Asn Leu Leu
    50                  55                  60

Lys Leu Ile Asp Glu Ile Gln Arg Leu Gly Ile Pro Tyr His Phe Glu
65                  70                  75                  80

Arg Glu Ile Asp His Ala Leu Gln Cys Ile Tyr Glu Thr Tyr Gly Asp
                85                  90                  95

Asn Trp Asn Gly Asp Arg Ser Ser Leu Trp Phe Arg Leu Met Arg Lys
            100                 105                 110

Gln Gly Tyr Tyr Val Thr Cys Asp Val Phe Asn Asn Tyr Lys Asp Lys
        115                 120                 125
```

-continued

```
Asn Gly Ala Phe Lys Gln Ser Leu Ala Asn Asp Val Gly Leu Leu
            130                 135                 140
Glu Leu Tyr Glu Ala Thr Ser Met Arg Val Pro Gly Glu Ile Ile Leu
145                 150                 155                 160
Glu Asp Ala Leu Gly Phe Thr Arg Ser Arg Leu Ser Ile Met Thr Lys
                    165                 170                 175
Asp Ala Phe Ser Thr Asn Pro Ala Leu Phe Thr Glu Ile Gln Arg Ala
                180                 185                 190
Leu Lys Gln Pro Leu Trp Lys Arg Leu Pro Arg Ile Glu Ala Ala Gln
            195                 200                 205
Tyr Ile Pro Phe Tyr Gln Gln Asp Ser His Asn Lys Thr Leu Leu
210                 215                 220
Lys Leu Ala Lys Leu Glu Phe Asn Leu Gln Ser Leu His Lys Glu
225                 230                 235                 240
Glu Leu Ser His Val Cys Lys Trp Trp Lys Ala Phe Asp Ile Lys Lys
                    245                 250                 255
Asn Ala Pro Cys Leu Arg Asp Arg Ile Val Glu Cys Tyr Phe Trp Gly
                260                 265                 270
Leu Gly Ser Gly Tyr Glu Pro Gln Tyr Ser Arg Ala Arg Val Phe Phe
            275                 280                 285
Thr Lys Ala Val Ala Val Ile Thr Leu Ile Asp Asp Thr Tyr Asp Ala
            290                 295                 300
Tyr Gly Thr Tyr Glu Glu Leu Lys Ile Phe Thr Glu Ala Val Glu Arg
305                 310                 315                 320
Trp Ser Ile Thr Cys Leu Asp Thr Leu Pro Glu Tyr Met Lys Pro Ile
                    325                 330                 335
Tyr Lys Leu Phe Met Asp Thr Tyr Thr Glu Met Glu Glu Phe Leu Ala
                340                 345                 350
Lys Glu Gly Arg Thr Asp Leu Phe Asn Cys Gly Lys Glu Phe Val Lys
            355                 360                 365
Glu Phe Val Arg Asn Leu Met Val Glu Ala Lys Trp Ala Asn Glu Gly
            370                 375                 380
His Ile Pro Thr Thr Glu Glu His Asp Pro Val Val Ile Ile Thr Gly
385                 390                 395                 400
Gly Ala Asn Leu Leu Thr Thr Thr Cys Tyr Leu Gly Met Ser Asp Ile
                    405                 410                 415
Phe Thr Lys Glu Ser Val Glu Trp Ala Val Ser Ala Pro Pro Leu Phe
                420                 425                 430
Arg Tyr Ser Gly Ile Leu Gly Arg Leu Asn Asp Leu Met Thr His
            435                 440                 445
Lys Ala Glu Gln Glu Arg Lys His Ser Ser Ser Leu Glu Ser Tyr
450                 455                 460
Met Lys Glu Tyr Asn Val Asn Glu Glu Tyr Ala Gln Thr Leu Ile Tyr
465                 470                 475                 480
Lys Glu Val Glu Asp Val Trp Lys Asp Ile Asn Arg Glu Tyr Leu Thr
                    485                 490                 495
Thr Lys Asn Ile Pro Arg Pro Leu Leu Met Ala Val Ile Tyr Leu Cys
                500                 505                 510
Gln Phe Leu Glu Val Gln Tyr Ala Gly Lys Asp Asn Phe Thr Arg Met
            515                 520                 525
```

```
Gly Asp Glu Tyr Lys His Leu Ile Lys Ser Leu Leu Val Tyr Pro Met
            530                 535                 540

Ser Ile
545

<210> SEQ ID NO 12
<211> LENGTH: 381
<212> TYPE: PRT
<213> ORGANISM: Abies grandis

<400> SEQUENCE: 12

Met Ala Tyr Ser Ala Met Ala Thr Met Gly Tyr Asn Gly Met Ala Ala
1               5                   10                  15

Ser Cys His Thr Leu His Pro Thr Ser Pro Leu Lys Pro Phe His Gly
                20                  25                  30

Ala Ser Thr Ser Leu Glu Ala Phe Asn Gly Glu His Met Gly Leu Leu
            35                  40                  45

Arg Gly Tyr Ser Lys Arg Lys Leu Ser Ser Tyr Lys Asn Pro Ala Ser
    50                  55                  60

Arg Ser Ser Asn Ala Thr Val Ala Gln Leu Leu Asn Pro Pro Gln Lys
65                  70                  75                  80

Gly Lys Lys Ala Val Glu Phe Asp Phe Asn Lys Tyr Met Asp Ser Lys
                85                  90                  95

Ala Met Thr Val Asn Glu Ala Leu Asn Lys Ala Ile Pro Leu Arg Tyr
            100                 105                 110

Pro Gln Lys Ile Tyr Glu Ser Met Arg Tyr Ser Leu Leu Ala Gly Gly
        115                 120                 125

Lys Arg Val Arg Pro Val Leu Cys Ile Ala Ala Cys Glu Leu Val Gly
130                 135                 140

Gly Thr Glu Glu Leu Ala Ile Pro Thr Ala Cys Ala Ile Glu Met Ile
145                 150                 155                 160

His Thr Met Ser Leu Met His Asp Asp Leu Pro Cys Ile Asp Asn Asp
                165                 170                 175

Asp Leu Arg Arg Gly Lys Pro Thr Asn His Lys Ile Phe Gly Glu Asp
            180                 185                 190

Thr Ala Val Thr Ala Gly Asn Ala Leu His Ser Tyr Ala Phe Glu His
        195                 200                 205

Ile Ala Val Ser Thr Ser Lys Thr Val Gly Ala Asp Arg Ile Leu Arg
    210                 215                 220

Met Val Ser Glu Leu Gly Arg Ala Thr Gly Ser Glu Gly Val Met Gly
225                 230                 235                 240

Gly Gln Met Val Asp Ile Ala Ser Glu Gly Asp Pro Ser Ile Asp Leu
                245                 250                 255

Gln Thr Leu Glu Trp Ile His Ile His Lys Thr Ala Met Leu Leu Glu
            260                 265                 270

Cys Ser Val Val Cys Gly Ala Ile Ile Gly Gly Ala Ser Glu Ile Val
        275                 280                 285

Ile Glu Arg Ala Arg Arg Tyr Ala Arg Cys Val Gly Leu Leu Phe Gln
    290                 295                 300

Val Val Asp Asp Ile Leu Asp Val Thr Lys Ser Ser Asp Glu Leu Gly
305                 310                 315                 320

Lys Thr Ala Gly Lys Asp Leu Ile Ser Asp Lys Ala Thr Tyr Pro Lys
                325                 330                 335

Leu Met Gly Leu Glu Lys Ala Lys Glu Phe Ser Asp Glu Leu Leu Asn
            340                 345                 350
```

```
Arg Ala Lys Gly Glu Leu Ser Cys Phe Asp Pro Val Lys Ala Ala Pro
            355                 360                 365

Leu Leu Gly Leu Ala Asp Tyr Val Ala Phe Arg Gln Asn
    370                 375                 380

<210> SEQ ID NO 13
<211> LENGTH: 606
<212> TYPE: PRT
<213> ORGANISM: Citrus limon

<400> SEQUENCE: 13

Met Ser Ser Cys Ile Asn Pro Ser Thr Leu Val Thr Ser Val Asn Ala
1               5                   10                  15

Phe Lys Cys Leu Pro Leu Ala Thr Asn Lys Ala Ala Ile Arg Ile Met
            20                  25                  30

Ala Lys Tyr Lys Pro Val Gln Cys Leu Ile Ser Ala Lys Tyr Asp Asn
        35                  40                  45

Leu Thr Val Asp Arg Arg Ser Ala Asn Tyr Gln Pro Ser Ile Trp Asp
    50                  55                  60

His Asp Phe Leu Gln Ser Leu Asn Ser Asn Tyr Thr Asp Glu Ala Tyr
65                  70                  75                  80

Lys Arg Arg Ala Glu Glu Leu Arg Gly Lys Val Lys Ile Ala Ile Lys
                85                  90                  95

Asp Val Ile Glu Pro Leu Asp Gln Leu Glu Leu Ile Asp Asn Leu Gln
            100                 105                 110

Arg Leu Gly Leu Ala His Arg Phe Glu Thr Glu Ile Arg Asn Ile Leu
        115                 120                 125

Asn Asn Ile Tyr Asn Asn Asn Lys Asp Tyr Asn Trp Arg Lys Glu Asn
    130                 135                 140

Leu Tyr Ala Thr Ser Leu Glu Phe Arg Leu Leu Arg Gln His Gly Tyr
145                 150                 155                 160

Pro Val Ser Gln Glu Val Phe Asn Gly Phe Lys Asp Asp Gln Gly Gly
                165                 170                 175

Phe Ile Cys Asp Asp Phe Lys Gly Ile Leu Ser Leu His Glu Ala Ser
            180                 185                 190

Tyr Tyr Ser Leu Glu Gly Glu Ser Ile Met Glu Glu Ala Trp Gln Phe
        195                 200                 205

Thr Ser Lys His Leu Lys Glu Val Met Ile Ser Lys Asn Met Glu Glu
    210                 215                 220

Asp Val Phe Val Ala Glu Gln Ala Lys Arg Ala Leu Glu Leu Pro Leu
225                 230                 235                 240

His Trp Lys Val Pro Met Leu Glu Ala Arg Trp Phe Ile His Ile Tyr
                245                 250                 255

Glu Arg Arg Glu Asp Lys Asn His Leu Leu Glu Leu Ala Lys Met
            260                 265                 270

Glu Phe Asn Thr Leu Gln Ala Ile Tyr Gln Glu Glu Leu Lys Glu Ile
        275                 280                 285

Ser Gly Trp Trp Lys Asp Thr Gly Leu Gly Glu Lys Leu Ser Phe Ala
    290                 295                 300

Arg Asn Arg Leu Val Ala Ser Phe Leu Trp Ser Met Gly Ile Ala Phe
305                 310                 315                 320

Glu Pro Gln Phe Ala Tyr Cys Arg Arg Val Leu Thr Ile Ser Ile Ala
                325                 330                 335

Leu Ile Thr Val Ile Asp Asp Ile Tyr Asp Val Tyr Gly Thr Leu Asp
            340                 345                 350
```

```
Glu Leu Glu Ile Phe Thr Asp Ala Val Glu Arg Trp Asp Ile Asn Tyr
            355                 360                 365

Ala Leu Lys His Leu Pro Gly Tyr Met Lys Met Cys Phe Leu Ala Leu
370                 375                 380

Tyr Asn Phe Val Asn Glu Phe Ala Tyr Val Leu Lys Gln Gln Asp
385                 390                 395                 400

Phe Asp Leu Leu Leu Ser Ile Lys Asn Ala Trp Leu Gly Leu Ile Gln
                405                 410                 415

Ala Tyr Leu Val Glu Ala Lys Trp Tyr His Ser Lys Tyr Thr Pro Lys
                420                 425                 430

Leu Glu Glu Tyr Leu Glu Asn Gly Leu Val Ser Ile Thr Gly Pro Leu
            435                 440                 445

Ile Ile Thr Ile Ser Tyr Leu Ser Gly Thr Asn Pro Ile Ile Lys Lys
            450                 455                 460

Glu Leu Glu Phe Leu Glu Ser Asn Pro Asp Ile Val His Trp Ser Ser
465                 470                 475                 480

Lys Ile Phe Arg Leu Gln Asp Asp Leu Gly Thr Ser Ser Asp Glu Ile
                485                 490                 495

Gln Arg Gly Asp Val Pro Lys Ser Ile Gln Cys Tyr Met His Glu Thr
                500                 505                 510

Gly Ala Ser Glu Glu Val Ala Arg Gln His Ile Lys Asp Met Met Arg
            515                 520                 525

Gln Met Trp Lys Lys Val Asn Ala Tyr Thr Ala Asp Lys Asp Ser Pro
            530                 535                 540

Leu Thr Gly Thr Thr Thr Glu Phe Leu Leu Asn Leu Val Arg Met Ser
545                 550                 555                 560

His Phe Met Tyr Leu His Gly Asp Gly His Gly Val Gln Asn Gln Glu
                565                 570                 575

Thr Ile Asp Val Gly Phe Thr Leu Leu Phe Gln Pro Ile Pro Leu Glu
            580                 585                 590

Asp Lys His Met Ala Phe Thr Ala Ser Pro Gly Thr Lys Gly
            595                 600                 605

<210> SEQ ID NO 14
<211> LENGTH: 300
<212> TYPE: PRT
<213> ORGANISM: Synechococcus spp.

<400> SEQUENCE: 14

Met Ala Val Ala Val Ser Thr Glu Phe Asp Phe Ala Ala Tyr Leu Glu
1               5                   10                  15

Ser Ala Arg Gly Gln Val Glu Leu Ala Leu Glu Ala Ala Leu Gly Pro
                20                  25                  30

Glu Arg Pro Glu Ser Leu Arg Glu Ala Met Arg Tyr Ser Leu Leu Ala
            35                  40                  45

Gly Gly Lys Arg Leu Arg Pro Ile Leu Cys Leu Ala Ala Cys Glu Leu
        50                  55                  60

Ala Gly Gly Glu Val Ala Leu Ala Leu Pro Thr Ala Val Ala Leu Glu
65                  70                  75                  80

Met Ile His Thr Met Ser Leu Ile His Asp Asp Leu Pro Ala Met Asp
                85                  90                  95

Asn Asp Asp Leu Arg Arg Gly Arg Pro Thr Asn His Lys Val Tyr Gly
                100                 105                 110

Asp Ala Gln Ala Ile Leu Ala Gly Asp Ala Leu Leu Thr Arg Ala Phe
            115                 120                 125
```

```
Glu Met Val Ala Leu Arg Ser Pro Gly Val Pro Ala Glu Arg Leu Leu
        130                 135                 140
Gln Val Val Gly Glu Leu Ser Leu Ala Ala Gly Ala Pro Gly Leu Val
145                 150                 155                 160
Gly Gly Gln Val Val Asp Leu Glu Ser Glu Gly Lys Asp Val Asp Leu
                    165                 170                 175
Ala Thr Leu Glu Tyr Ile His Leu His Lys Thr Gly Ala Leu Leu Gln
                180                 185                 190
Ala Cys Val Leu Thr Gly Ala Met Ile Ala Gly Ala Pro Glu Pro Leu
                195                 200                 205
Leu Gln Gly Leu Arg Thr Tyr Ser Arg Gly Ile Gly Leu Ala Phe Gln
        210                 215                 220
Ile Ile Asp Asp Ile Leu Asp Val Thr Ala Ser Ser Glu Val Leu Gly
225                 230                 235                 240
Lys Thr Ala Gly Lys Asp Leu Thr Ala Asp Lys Thr Thr Tyr Pro Lys
                245                 250                 255
Leu Leu Gly Leu Glu Glu Ser Arg Gln Arg Ala Asp Ala Leu Val Ala
                260                 265                 270
Glu Ala Lys Ala Ala Leu Gln Pro Trp Gln Ala Ser Ala Gln Pro Leu
        275                 280                 285
Leu Ala Leu Ala Asp Tyr Ile Thr Ser Arg Asp Arg
        290                 295                 300

<210> SEQ ID NO 15

<400> SEQUENCE: 15

000

<210> SEQ ID NO 16

<400> SEQUENCE: 16

000

<210> SEQ ID NO 17
<211> LENGTH: 785
<212> TYPE: PRT
<213> ORGANISM: Arabidopsis thaliana

<400> SEQUENCE: 17

Met Ser Ile Asn Leu Arg Ser Ser Gly Cys Ser Ser Pro Ile Ser Ala
1               5                   10                  15

Thr Leu Glu Arg Gly Leu Asp Ser Glu Val Gln Thr Arg Ala Asn Asn
                20                  25                  30

Val Ser Phe Glu Gln Thr Lys Glu Lys Ile Arg Lys Met Leu Glu Lys
                35                  40                  45

Val Glu Leu Ser Val Ser Ala Tyr Asp Thr Ser Trp Val Ala Met Val
            50                  55                  60

Pro Ser Pro Ser Ser Gln Asn Ala Pro Leu Phe Pro Gln Cys Val Lys
65                  70                  75                  80

Trp Leu Leu Asp Asn Gln His Glu Asp Gly Ser Trp Gly Leu Asp Asn
                85                  90                  95

His Asp His Gln Ser Leu Lys Lys Asp Val Leu Ser Ser Thr Leu Ala
                100                 105                 110

Ser Ile Leu Ala Leu Lys Lys Trp Gly Ile Gly Glu Arg Gln Ile Asn
        115                 120                 125
```

-continued

```
Lys Gly Leu Gln Phe Ile Glu Leu Asn Ser Ala Leu Val Thr Asp Glu
130                 135                 140

Thr Ile Gln Lys Pro Thr Gly Phe Asp Ile Ile Phe Pro Gly Met Ile
145                 150                 155                 160

Lys Tyr Ala Arg Asp Leu Asn Leu Thr Ile Pro Leu Gly Ser Glu Val
                165                 170                 175

Val Asp Asp Met Ile Arg Lys Arg Asp Leu Asp Leu Lys Cys Asp Ser
            180                 185                 190

Glu Lys Phe Ser Lys Gly Arg Glu Ala Tyr Leu Ala Tyr Val Leu Glu
        195                 200                 205

Gly Thr Arg Asn Leu Lys Asp Trp Asp Leu Ile Val Lys Tyr Gln Arg
210                 215                 220

Lys Asn Gly Ser Leu Phe Asp Ser Pro Ala Thr Ala Ala Ala Phe
225                 230                 235                 240

Thr Gln Phe Gly Asn Asp Gly Cys Leu Arg Tyr Leu Cys Ser Leu Leu
                245                 250                 255

Gln Lys Phe Glu Ala Ala Val Pro Ser Val Tyr Pro Phe Asp Gln Tyr
            260                 265                 270

Ala Arg Leu Ser Ile Ile Val Thr Leu Glu Ser Leu Gly Ile Asp Arg
        275                 280                 285

Asp Phe Lys Thr Glu Ile Lys Ser Ile Leu Asp Glu Thr Tyr Arg Tyr
290                 295                 300

Trp Leu Arg Gly Asp Glu Glu Ile Cys Leu Asp Leu Ala Thr Cys Ala
305                 310                 315                 320

Leu Ala Phe Arg Leu Leu Ala His Gly Tyr Asp Val Ser Tyr Asp
                325                 330                 335

Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
        355                 360                 365

Gln Ser Tyr Pro His Glu Ser Ala Leu Lys Lys Gln Cys Cys Trp Thr
370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Arg Lys Ile Leu Asn
            420                 425                 430

Gly Ser Ala Val Glu Asn Thr Arg Val Thr Lys Thr Ser Tyr Arg Leu
        435                 440                 445

His Asn Ile Cys Thr Ser Asp Ile Leu Lys Leu Ala Val Asp Asp Phe
450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
        515                 520                 525

Val Val Asp Asp Phe Phe Asp Val Gly Gly Ser Lys Glu Glu Leu Glu
530                 535                 540
```

```
Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
            565                 570                 575

Ile Leu Glu Thr Gly Asp Lys Ala Phe Thr Tyr Gln Gly Arg Asn Val
        580                 585                 590

Thr His His Ile Val Lys Ile Trp Leu Asp Leu Leu Lys Ser Met Leu
    595                 600                 605

Arg Glu Ala Glu Trp Ser Ser Asp Lys Ser Thr Pro Ser Leu Glu Asp
610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
            645                 650                 655

Ser His Gln Tyr Asn Gln Leu Tyr Lys Leu Val Ser Thr Met Gly Arg
        660                 665                 670

Leu Leu Asn Asp Ile Gln Gly Phe Lys Arg Glu Ser Ala Glu Gly Lys
    675                 680                 685

Leu Asn Ala Val Ser Leu His Met Lys His Glu Arg Asp Asn Arg Ser
690                 695                 700

Lys Glu Val Ile Ile Glu Ser Met Lys Gly Leu Ala Glu Arg Lys Arg
705                 710                 715                 720

Glu Glu Leu His Lys Leu Val Leu Glu Lys Gly Ser Val Val Pro
            725                 730                 735

Arg Glu Cys Lys Glu Ala Phe Leu Lys Met Ser Lys Val Leu Asn Leu
            740                 745                 750

Phe Tyr Arg Lys Asp Asp Gly Phe Thr Ser Asn Asp Leu Met Ser Leu
        755                 760                 765

Val Lys Ser Val Ile Tyr Glu Pro Val Ser Leu Gln Lys Glu Ser Leu
    770                 775                 780

Thr
785

<210> SEQ ID NO 18
<211> LENGTH: 802
<212> TYPE: PRT
<213> ORGANISM: Arabidopsis thaliana

<400> SEQUENCE: 18

Met Ser Leu Gln Tyr His Val Leu Asn Ser Ile Pro Ser Thr Thr Phe
1               5                   10                  15

Leu Ser Ser Thr Lys Thr Thr Ile Ser Ser Ser Phe Leu Thr Ile Ser
            20                  25                  30

Gly Ser Pro Leu Asn Val Ala Arg Asp Lys Ser Arg Ser Gly Ser Ile
        35                  40                  45

His Cys Ser Lys Leu Arg Thr Gln Glu Tyr Ile Asn Ser Gln Glu Val
    50                  55                  60

Gln His Asp Leu Pro Leu Ile His Glu Trp Gln Gln Leu Gln Gly Glu
65                  70                  75                  80

Asp Ala Pro Gln Ile Ser Val Gly Ser Asn Ser Asn Ala Phe Lys Glu
            85                  90                  95

Ala Val Lys Ser Val Lys Thr Ile Leu Arg Asn Leu Thr Asp Gly Glu
            100                 105                 110

Ile Thr Ile Ser Ala Tyr Asp Thr Ala Trp Val Ala Leu Ile Asp Ala
        115                 120                 125
```

```
Gly Asp Lys Thr Pro Ala Phe Pro Ser Ala Val Lys Trp Ile Ala Glu
            130                 135                 140

Asn Gln Leu Ser Asp Gly Ser Trp Gly Asp Ala Tyr Leu Phe Ser Tyr
145                 150                 155                 160

His Asp Arg Leu Ile Asn Thr Leu Ala Cys Val Val Ala Leu Arg Ser
                165                 170                 175

Trp Asn Leu Phe Pro His Gln Cys Asn Lys Gly Ile Thr Phe Phe Arg
            180                 185                 190

Glu Asn Ile Gly Lys Leu Glu Asp Glu Asn Asp Glu His Met Pro Ile
        195                 200                 205

Gly Phe Glu Val Ala Phe Pro Ser Leu Leu Glu Ile Ala Arg Gly Ile
210                 215                 220

Asn Ile Asp Val Pro Tyr Asp Ser Pro Val Leu Lys Asp Ile Tyr Ala
225                 230                 235                 240

Lys Lys Glu Leu Lys Leu Thr Arg Ile Pro Lys Glu Ile Met His Lys
                245                 250                 255

Ile Pro Thr Thr Leu Leu His Ser Leu Glu Gly Met Arg Asp Leu Asp
            260                 265                 270

Trp Glu Lys Leu Leu Lys Leu Gln Ser Gln Asp Gly Ser Phe Leu Phe
        275                 280                 285

Ser Pro Ser Ser Thr Ala Phe Ala Phe Met Gln Thr Arg Asp Ser Asn
290                 295                 300

Cys Leu Glu Tyr Leu Arg Asn Ala Val Lys Arg Phe Asn Gly Gly Val
305                 310                 315                 320

Pro Asn Val Phe Pro Val Asp Leu Phe Glu His Ile Trp Ile Val Asp
                325                 330                 335

Arg Leu Gln Arg Leu Gly Ile Ser Arg Tyr Phe Glu Glu Glu Ile Lys
            340                 345                 350

Glu Cys Leu Asp Tyr Val His Arg Tyr Trp Thr Asp Asn Gly Ile Cys
        355                 360                 365

Trp Ala Arg Cys Ser His Val Gln Asp Ile Asp Asp Thr Ala Met Ala
370                 375                 380

Phe Arg Leu Leu Arg Gln His Gly Tyr Gln Val Ser Ala Asp Val Phe
385                 390                 395                 400

Lys Asn Phe Glu Lys Glu Gly Glu Phe Phe Cys Phe Val Gly Gln Ser
                405                 410                 415

Asn Gln Ala Val Thr Gly Met Phe Asn Leu Tyr Arg Ala Ser Gln Leu
            420                 425                 430

Ala Phe Pro Arg Glu Glu Ile Leu Lys Asn Ala Lys Glu Phe Ser Tyr
        435                 440                 445

Asn Tyr Leu Leu Glu Lys Arg Glu Arg Glu Glu Leu Ile Asp Lys Trp
450                 455                 460

Ile Ile Met Lys Asp Leu Pro Gly Glu Ile Gly Phe Ala Leu Glu Ile
465                 470                 475                 480

Pro Trp Tyr Ala Ser Leu Pro Arg Val Glu Thr Arg Phe Tyr Ile Asp
                485                 490                 495

Gln Tyr Gly Gly Glu Asn Asp Val Trp Ile Gly Lys Thr Leu Tyr Arg
            500                 505                 510

Met Pro Tyr Val Asn Asn Gly Tyr Leu Glu Leu Ala Lys Gln Asp
        515                 520                 525

Tyr Asn Asn Cys Gln Ala Gln His Gln Leu Glu Trp Asp Ile Phe Gln
530                 535                 540
```

```
Lys Trp Tyr Glu Glu Asn Arg Leu Ser Glu Trp Gly Val Arg Arg Ser
545                 550                 555                 560

Glu Leu Leu Glu Cys Tyr Tyr Leu Ala Ala Thr Ile Phe Glu Ser
            565                 570                 575

Glu Arg Ser His Glu Arg Met Val Trp Ala Lys Ser Ser Val Leu Val
                580                 585                 590

Lys Ala Ile Ser Ser Ser Phe Gly Glu Ser Ser Asp Ser Arg Arg Ser
                595                 600                 605

Phe Ser Asp Gln Phe His Glu Tyr Ile Ala Asn Ala Arg Arg Ser Asp
            610                 615                 620

His His Phe Asn Asp Arg Asn Met Arg Leu Asp Arg Pro Gly Ser Val
625                 630                 635                 640

Gln Ala Ser Arg Leu Ala Gly Val Leu Ile Gly Thr Leu Asn Gln Met
                645                 650                 655

Ser Phe Asp Leu Phe Met Ser His Gly Arg Asp Val Asn Asn Leu Leu
            660                 665                 670

Tyr Leu Ser Trp Gly Asp Trp Met Glu Lys Trp Lys Leu Tyr Gly Asp
            675                 680                 685

Glu Gly Glu Gly Glu Leu Met Val Lys Met Ile Ile Leu Met Lys Asn
690                 695                 700

Asn Asp Leu Thr Asn Phe Phe Thr His Thr His Phe Val Arg Leu Ala
705                 710                 715                 720

Glu Ile Ile Asn Arg Ile Cys Leu Pro Arg Gln Tyr Leu Lys Ala Arg
                725                 730                 735

Arg Asn Asp Glu Lys Glu Lys Thr Ile Lys Ser Met Glu Lys Glu Met
                740                 745                 750

Gly Lys Met Val Glu Leu Ala Leu Ser Glu Ser Asp Thr Phe Arg Asp
            755                 760                 765

Val Ser Ile Thr Phe Leu Asp Val Ala Lys Ala Phe Tyr Tyr Phe Ala
            770                 775                 780

Leu Cys Gly Asp His Leu Gln Thr His Ile Ser Lys Val Leu Phe Gln
785                 790                 795                 800

Lys Val

<210> SEQ ID NO 19
<211> LENGTH: 352
<212> TYPE: PRT
<213> ORGANISM: Saccharomyces cerevisiae

<400> SEQUENCE: 19

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
                20                  25                  30

Pro Lys Glu Ala Cys Asp Trp Tyr Ala His Ser Leu Asn Tyr Asn Thr
            35                  40                  45

Pro Gly Gly Lys Leu Asn Arg Gly Leu Ser Val Val Asp Thr Tyr Ala
        50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
                100                 105                 110
```

Pro Cys Trp Tyr Lys Val Pro Glu Val Gly Glu Ile Ala Ile Asn Asp
            115                 120                 125

Ala Phe Met Leu Glu Ala Ala Ile Tyr Lys Leu Leu Lys Ser His Phe
        130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350

<210> SEQ ID NO 20
<211> LENGTH: 346
<212> TYPE: PRT
<213> ORGANISM: Artemisia tridentata

<400> SEQUENCE: 20

Met Ser Ser Ser Lys Ser Ile Asp Leu Lys Ser Lys Phe Leu Lys Val
1               5                   10                  15

Tyr Asp Thr Leu Lys Ser Asp Leu Ile Asn Asp Pro Ala Phe Glu Phe
            20                  25                  30

Asp Asp Asp Ser Arg Gln Trp Ile Gln Lys Met Leu Asp Tyr Asn Val
        35                  40                  45

Pro Gly Gly Lys Leu Asn Arg Gly Leu Ser Val Val Asp Ser Tyr Gln
    50                  55                  60

Leu Leu Lys Gly Gly Glu Leu Ser Asp Glu Ile Phe Leu Ser Ser
65                  70                  75                  80

Ala Leu Gly Trp Cys Ile Glu Trp Leu Gln Ala Tyr Phe Leu Val Leu
                85                  90                  95

Asp Asp Ile Met Asp Glu Ser His Thr Arg Arg Gly Gln Pro Cys Trp
            100                 105                 110

Phe Arg Leu Pro Lys Val Gly Met Ile Ala Ala Asn Asp Gly Ile Leu
        115                 120                 125

Leu Arg Asn His Val Pro Arg Ile Leu Lys Lys His Phe Arg Gly Lys
    130                 135                 140

-continued

Pro Tyr Tyr Val Asp Leu Val Asp Leu Phe Asn Glu Val Glu Phe Gln
145                 150                 155                 160

Thr Ala Ser Gly Gln Met Ile Asp Leu Ile Thr Thr Leu Val Gly Glu
            165                 170                 175

Lys Asp Leu Ser Lys Tyr Ser Leu Ser Ile His Arg Arg Ile Val Gln
            180                 185                 190

Tyr Lys Thr Ala Tyr Tyr Ser Phe Tyr Leu Pro Val Ala Cys Ala Leu
        195                 200                 205

Leu Met Phe Gly Glu Asp Leu Asp Lys His Val Glu Val Lys Asn Val
    210                 215                 220

Leu Val Glu Met Gly Thr Tyr Phe Gln Val Gln Asp Asp Tyr Leu Asp
225                 230                 235                 240

Cys Phe Gly Ala Pro Glu Val Ile Gly Lys Ile Gly Thr Asp Ile Glu
                245                 250                 255

Asp Phe Lys Cys Ser Trp Leu Val Val Lys Ala Leu Glu Leu Ala Asn
            260                 265                 270

Glu Glu Gln Lys Lys Thr Leu His Glu Asn Tyr Gly Lys Lys Asp Pro
        275                 280                 285

Ala Ser Val Ala Lys Val Lys Glu Val Tyr His Thr Leu Asn Leu Gln
    290                 295                 300

Ala Val Phe Glu Asp Tyr Glu Ala Thr Ser Tyr Lys Lys Leu Ile Thr
305                 310                 315                 320

Ser Ile Glu Asn His Pro Ser Lys Ala Val Gln Ala Val Leu Lys Ser
                325                 330                 335

Phe Leu Gly Lys Ile Tyr Lys Arg Gln Lys
            340                 345

<210> SEQ ID NO 21
<211> LENGTH: 342
<212> TYPE: PRT
<213> ORGANISM: Artemisia tridentata

<400> SEQUENCE: 21

Met Ser Ile Asp Leu Lys Ser Arg Phe Leu Gln Val Tyr Asp Ser Leu
1               5                   10                  15

Lys Ser Asp Leu Ile His Asp Pro Ala Phe Glu Phe Asp Asp Asp Ser
            20                  25                  30

Arg Asn Trp Val Glu Arg Met Leu Asp Tyr Asn Val Pro Gly Gly Lys
        35                  40                  45

Leu Asn Arg Gly Leu Ser Val Val Asp Ser Tyr Lys Leu Leu Lys Gln
50                  55                  60

Glu Glu Leu Thr Glu Asp Glu Val Phe Leu Ala Cys Ala Leu Gly Trp
65                  70                  75                  80

Cys Ile Glu Trp Leu Gln Ala Tyr Phe Leu Val Leu Asp Asp Ile Met
                85                  90                  95

Asp Glu Ser His Thr Arg Arg Gly Gln Pro Cys Trp Phe Arg Leu Pro
            100                 105                 110

Lys Val Gly Met Ile Ala Val Asn Asp Gly Val Val Leu Arg Asn His
        115                 120                 125

Ile Pro Arg Ile Leu Lys Lys His Phe Arg Gly Lys Ala Tyr Tyr Ala
    130                 135                 140

Asp Leu Leu Asp Leu Phe Asn Glu Val Glu Phe Gln Thr Ala Ser Gly
145                 150                 155                 160

Gln Met Ile Asp Leu Ile Thr Thr Leu Phe Gly Gln Lys Glu Leu Ser
                165                 170                 175

```
Lys Tyr Ser Leu Ser Thr His Gln Arg Ile Val Lys Phe Lys Thr Ala
                180                 185                 190

Tyr Tyr Ser Phe Tyr Leu Pro Val Ala Cys Ala Leu Leu Met Phe Gly
            195                 200                 205

Glu Asn Leu Asp Asp His Val Gln Val Lys Asp Val Leu Val Glu Met
        210                 215                 220

Gly Thr Tyr Phe Gln Val Gln Asp Asp Tyr Leu Asp Cys Phe Gly Ser
225                 230                 235                 240

Pro Glu Val Ile Gly Lys Ile Gly Thr Asp Ile Glu Asp Phe Lys Cys
                245                 250                 255

Ser Trp Leu Val Val Lys Ala Leu Glu Leu Ala Asp Glu Gln Gln Lys
            260                 265                 270

Lys Leu Leu Asn Glu Asn Tyr Gly Arg Lys Asp Pro Ala Ser Val Ala
        275                 280                 285

Lys Val Lys Glu Leu Tyr His Thr Leu Asn Leu Gln Gly Val Phe Glu
290                 295                 300

Asp Tyr Glu Asn Lys Ser His Glu Lys Ile Ile Lys Ser Ile Glu Thr
305                 310                 315                 320

His Pro Ser Lys Ala Val Gln Glu Val Leu Lys Ser Phe Leu Gly Lys
                325                 330                 335

Ile Phe Lys Arg Gln Lys
            340

<210> SEQ ID NO 22
<211> LENGTH: 247
<212> TYPE: PRT
<213> ORGANISM: Arabidopsis thaliana

<400> SEQUENCE: 22

Met Asp Asn Ser Val Thr Arg Arg Gly Gln Pro Cys Trp Phe Arg Lys
1               5                   10                  15

Pro Lys Val Gly Met Ile Ala Ile Asn Asp Gly Ile Leu Leu Arg Asn
            20                  25                  30

His Ile His Arg Ile Leu Lys Lys His Phe Arg Glu Met Pro Tyr Tyr
        35                  40                  45

Val Asp Leu Val Asp Leu Phe Asn Glu Val Glu Phe Gln Thr Ala Cys
    50                  55                  60

Gly Gln Met Ile Asp Leu Ile Thr Thr Phe Asp Gly Glu Lys Asp Leu
65                  70                  75                  80

Ser Lys Tyr Ser Leu Gln Ile His Arg Arg Ile Val Glu Tyr Lys Thr
                85                  90                  95

Ala Tyr Tyr Ser Phe Tyr Leu Pro Val Ala Cys Ala Leu Leu Met Ala
            100                 105                 110

Gly Glu Asn Leu Glu Asn His Thr Asp Val Lys Thr Val Leu Val Asp
        115                 120                 125

Met Gly Ile Tyr Phe Gln Val Gln Asp Asp Tyr Leu Asp Cys Phe Ala
    130                 135                 140

Asp Pro Glu Thr Leu Gly Lys Ile Gly Thr Asp Ile Glu Asp Phe Lys
145                 150                 155                 160

Cys Ser Trp Leu Val Val Lys Ala Leu Glu Arg Cys Ser Glu Glu Gln
                165                 170                 175

Thr Lys Ile Leu Tyr Glu Asn Tyr Gly Lys Ala Glu Pro Ser Asn Val
            180                 185                 190

Ala Lys Val Lys Ala Leu Tyr Lys Glu Leu Asp Leu Glu Gly Ala Phe
        195                 200                 205
```

```
Met Glu Tyr Glu Lys Glu Ser Tyr Glu Lys Leu Thr Lys Leu Ile Glu
    210                 215                 220

Ala His Gln Ser Lys Ala Ile Gln Ala Val Leu Lys Ser Phe Leu Ala
225                 230                 235                 240

Lys Ile Tyr Lys Arg Gln Lys
                245

<210> SEQ ID NO 23
<211> LENGTH: 335
<212> TYPE: PRT
<213> ORGANISM: Saccharomyces cerevisiae

<400> SEQUENCE: 23

Met Glu Ala Lys Ile Asp Glu Leu Ile Asn Asn Asp Pro Val Trp Ser
1               5                   10                  15

Ser Gln Asn Glu Ser Leu Ile Ser Lys Pro Tyr Asn His Ile Leu Leu
            20                  25                  30

Lys Pro Gly Lys Asn Phe Arg Leu Asn Leu Ile Val Gln Ile Asn Arg
        35                  40                  45

Val Met Asn Leu Pro Lys Asp Gln Leu Ala Ile Val Ser Gln Ile Val
    50                  55                  60

Glu Leu Leu His Asn Ser Ser Leu Leu Ile Asp Asp Ile Glu Asp Asn
65                  70                  75                  80

Ala Pro Leu Arg Arg Gly Gln Thr Thr Ser His Leu Ile Phe Gly Val
                85                  90                  95

Pro Ser Thr Ile Asn Thr Ala Asn Tyr Met Tyr Phe Arg Ala Met Gln
            100                 105                 110

Leu Val Ser Gln Leu Thr Thr Lys Glu Pro Leu Tyr His Asn Leu Ile
        115                 120                 125

Thr Ile Phe Asn Glu Glu Leu Ile Asn Leu His Arg Gly Gln Gly Leu
130                 135                 140

Asp Ile Tyr Trp Arg Asp Phe Leu Pro Glu Ile Ile Pro Thr Gln Glu
145                 150                 155                 160

Met Tyr Leu Asn Met Val Met Asn Lys Thr Gly Gly Leu Phe Arg Leu
                165                 170                 175

Thr Leu Arg Leu Met Glu Ala Leu Ser Pro Ser Ser His His Gly His
            180                 185                 190

Ser Leu Val Pro Phe Ile Asn Leu Leu Gly Ile Ile Tyr Gln Ile Arg
        195                 200                 205

Asp Asp Tyr Leu Asn Leu Lys Asp Phe Gln Met Ser Ser Glu Lys Gly
210                 215                 220

Phe Ala Glu Asp Ile Thr Glu Gly Lys Leu Ser Phe Pro Ile Val His
225                 230                 235                 240

Ala Leu Asn Phe Thr Lys Thr Lys Gly Gln Thr Glu Gln His Asn Glu
                245                 250                 255

Ile Leu Arg Ile Leu Leu Leu Arg Thr Ser Asp Lys Asp Ile Lys Leu
            260                 265                 270

Lys Leu Ile Gln Ile Leu Glu Phe Asp Thr Asn Ser Leu Ala Tyr Thr
        275                 280                 285

Lys Asn Phe Ile Asn Gln Leu Val Asn Met Ile Lys Asn Asp Asn Glu
290                 295                 300

Asn Lys Tyr Leu Pro Asp Leu Ala Ser His Ser Asp Thr Ala Thr Asn
305                 310                 315                 320

Leu His Asp Glu Leu Leu Tyr Ile Ile Asp His Leu Ser Glu Leu
                325                 330                 335
```

<210> SEQ ID NO 24

<400> SEQUENCE: 24

000

<210> SEQ ID NO 25
<211> LENGTH: 330
<212> TYPE: PRT
<213> ORGANISM: Sulfobacillus acidophilus

<400> SEQUENCE: 25

```
Met Ser Tyr Phe Asp Asn Tyr Phe Asn Glu Ile Val Asn Ser Val Asn
1               5                   10                  15

Asp Ile Ile Lys Ser Tyr Ile Ser Gly Asp Val Pro Lys Leu Tyr Glu
            20                  25                  30

Ala Ser Tyr His Leu Phe Thr Ser Gly Gly Lys Arg Leu Arg Pro Leu
        35                  40                  45

Ile Leu Thr Ile Ser Ser Asp Leu Phe Gly Gly Gln Arg Glu Arg Ala
    50                  55                  60

Tyr Tyr Ala Gly Ala Ala Ile Glu Val Leu His Thr Phe Thr Leu Val
65                  70                  75                  80

His Asp Asp Ile Met Asp Gln Asp Asn Ile Arg Arg Gly Leu Pro Thr
                85                  90                  95

Val His Val Lys Tyr Gly Leu Pro Leu Ala Ile Leu Ala Gly Asp Leu
            100                 105                 110

Leu His Ala Lys Ala Phe Gln Leu Leu Thr Gln Ala Leu Arg Gly Leu
        115                 120                 125

Pro Ser Glu Thr Ile Ile Lys Ala Phe Asp Ile Phe Thr Arg Ser Ile
    130                 135                 140

Ile Ile Ile Ser Glu Gly Gln Ala Val Asp Met Glu Phe Glu Asp Arg
145                 150                 155                 160

Ile Asp Ile Lys Glu Gln Glu Tyr Leu Asp Met Ile Ser Arg Lys Thr
                165                 170                 175

Ala Ala Leu Phe Ser Ala Ser Ser Ile Gly Ala Leu Ile Ala Gly
            180                 185                 190

Ala Asn Asp Asn Asp Val Arg Leu Met Ser Asp Phe Gly Thr Asn Leu
        195                 200                 205

Gly Ile Ala Phe Gln Ile Val Asp Asp Ile Leu Gly Leu Thr Ala Asp
    210                 215                 220

Glu Lys Glu Leu Gly Lys Pro Val Phe Ser Asp Ile Arg Glu Gly Lys
225                 230                 235                 240

Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
        275                 280                 285

Ala Tyr Asn Leu Ala Glu Lys Tyr Tyr Lys Asn Ala Ile Asp Ser Leu
    290                 295                 300

Asn Gln Val Ser Ser Lys Ser Asp Ile Pro Gly Lys Ala Leu Lys Tyr
305                 310                 315                 320

Leu Ala Glu Phe Thr Ile Arg Arg Arg Lys
                325                 330
```

<210> SEQ ID NO 26
<211> LENGTH: 386
<212> TYPE: PRT
<213> ORGANISM: Picea abies

<400> SEQUENCE: 26

Met Gly Tyr Asn Gly Met Val Val Ser Ser Asn Leu Gly Leu Tyr Tyr
1               5                   10                  15

Leu Asn Ile Ala Ser Arg Glu Cys Asn Leu Lys Arg Ile Ser Ile Pro
            20                  25                  30

Ser Pro Phe His Gly Val Ser Thr Ser Leu Gly Ser Ser Thr Ser Lys
        35                  40                  45

His Leu Gly Leu Arg Gly His Leu Lys Lys Glu Leu Leu Ser His Arg
    50                  55                  60

Leu Leu Leu Ser Ser Thr Arg Ser Ser Lys Ala Leu Val Gln Leu Ala
65                  70                  75                  80

Asp Leu Ser Glu Gln Val Lys Asn Val Val Glu Phe Asp Phe Asp Lys
                85                  90                  95

Tyr Met His Ser Lys Ala Ile Ala Val Asn Glu Ala Leu Asp Lys Val
            100                 105                 110

Ile Pro Pro Arg Tyr Pro Gln Lys Ile Tyr Glu Ser Met Arg Tyr Ser
        115                 120                 125

Leu Leu Ala Gly Gly Lys Arg Val Arg Pro Ile Leu Cys Ile Ala Ala
    130                 135                 140

Cys Glu Leu Met Gly Gly Thr Glu Gly Leu Ala Met Pro Thr Ala Cys
145                 150                 155                 160

Ala Ile Glu Met Ile His Thr Met Ser Leu Ile His Asp Asp Leu Pro
                165                 170                 175

Tyr Ile Asp Asn Asp Asp Leu Arg Arg Gly Lys Pro Thr Asn His Lys
            180                 185                 190

Val Phe Gly Glu Asp Thr Ala Ile Ile Ala Gly Asp Ala Leu Leu Ser
        195                 200                 205

Leu Ala Phe Glu His Val Ala Val Ser Thr Ser Arg Thr Leu Gly Thr
    210                 215                 220

Asp Ile Ile Leu Arg Leu Leu Ser Glu Ile Gly Arg Ala Thr Gly Ser
225                 230                 235                 240

Glu Gly Val Met Gly Gly Gln Val Val Asp Ile Glu Ser Glu Gly Asp
                245                 250                 255

Pro Ser Ile Asp Leu Glu Thr Leu Glu Trp Val His Ile His Lys Thr
            260                 265                 270

Ala Val Leu Leu Glu Cys Ser Val Val Cys Gly Ala Ile Met Gly Gly
        275                 280                 285

Ala Ser Glu Asp Asp Ile Glu Arg Ala Arg Arg Tyr Ala Arg Cys Val
    290                 295                 300

Gly Leu Leu Phe Gln Val Val Asp Asp Ile Leu Asp Val Ser Gln Ser
305                 310                 315                 320

Ser Glu Glu Leu Gly Lys Thr Ala Gly Lys Asp Leu Ile Ser Asp Lys
                325                 330                 335

Ala Thr Tyr Pro Lys Leu Met Gly Leu Glu Lys Ala Lys Glu Phe Ala
            340                 345                 350

Asp Glu Leu Leu Asn Arg Gly Lys Gln Glu Leu Ser Cys Phe Asp Pro
        355                 360                 365

```
Thr Lys Ala Ala Pro Leu Phe Ala Leu Ala Asp Tyr Ile Ala Ser Arg
        370                 375                 380

Gln Asn
385
```

<210> SEQ ID NO 27
<211> LENGTH: 444
<212> TYPE: PRT
<213> ORGANISM: Saccharomyces cerevisiae

<400> SEQUENCE: 27

```
Met Gly Lys Leu Leu Gln Leu Ala Leu His Pro Val Glu Met Lys Ala
1               5                   10                  15

Ala Leu Lys Leu Lys Phe Cys Arg Thr Pro Leu Phe Ser Ile Tyr Asp
            20                  25                  30

Gln Ser Thr Ser Pro Tyr Leu Leu His Cys Phe Glu Leu Leu Asn Phe
        35                  40                  45

Thr Ser Arg Ser Phe Ala Ala Val Ile Arg Glu Leu His Pro Glu Leu
    50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
            100                 105                 110

Asn Ala Pro Asp Val Lys Asp Arg Ala Val Leu Thr Asp Phe Glu Ser
        115                 120                 125

Ile Leu Ile Glu Phe His Lys Leu Lys Pro Glu Tyr Gln Glu Val Ile
    130                 135                 140

Lys Glu Ile Thr Glu Lys Met Gly Asn Gly Met Ala Asp Tyr Ile Leu
145                 150                 155                 160

Asp Glu Asn Tyr Asn Leu Asn Gly Leu Gln Thr Val His Asp Tyr Asp
                165                 170                 175

Val Tyr Cys His Tyr Val Ala Gly Leu Val Gly Asp Gly Leu Thr Arg
            180                 185                 190

Leu Ile Val Ile Ala Lys Phe Ala Asn Glu Ser Leu Tyr Ser Asn Glu
        195                 200                 205

Gln Leu Tyr Glu Ser Met Gly Leu Phe Leu Gln Lys Thr Asn Ile Ile
    210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
                245                 250                 255

Glu Asn Glu Gln Leu Gly Leu Asp Cys Ile Asn His Leu Val Leu Asn
            260                 265                 270

Ala Leu Ser His Val Ile Asp Val Leu Thr Tyr Leu Ala Gly Ile His
        275                 280                 285

Glu Gln Ser Thr Phe Gln Phe Cys Ala Ile Pro Gln Val Met Ala Ile
    290                 295                 300

Ala Thr Leu Ala Leu Val Phe Asn Asn Arg Glu Val Leu His Gly Asp
305                 310                 315                 320

Val Lys Ile Arg Lys Gly Thr Thr Cys Cys Leu Ile Leu Lys Ser Arg
                325                 330                 335

Thr Leu Arg Gly Cys Val Glu Ile Phe Asp Tyr Tyr Leu Arg Asp Ile
            340                 345                 350
```

Lys Ser Lys Leu Ala Val Gln Asp Pro Asn Phe Leu Lys Leu Asn Ile
        355                 360                 365

Gln Ile Ser Lys Ile Glu Gln Phe Met Glu Met Tyr Gln Asp Lys
        370                 375                 380

Leu Pro Pro Asn Val Lys Pro Asn Glu Thr Pro Ile Phe Leu Lys Val
385                 390                 395                 400

Lys Glu Arg Ser Arg Tyr Asp Asp Glu Leu Val Pro Thr Gln Gln Glu
                405                 410                 415

Glu Glu Tyr Lys Phe Asn Met Val Leu Ser Ile Ile Ser Ser Val Leu
            420                 425                 430

Leu Gly Phe Tyr Tyr Ile Tyr Thr Leu His Arg Ala
            435                 440

<210> SEQ ID NO 28
<211> LENGTH: 13
<212> TYPE: DNA
<213> ORGANISM: Artificial Sequence
<220> FEATURE:
<223> OTHER INFORMATION: mRNA destabilizing consensus sequence

<400> SEQUENCE: 28
tatatatata tat                                                      13

<210> SEQ ID NO 29
<211> LENGTH: 9
<212> TYPE: DNA
<213> ORGANISM: Artificial Sequence
<220> FEATURE:
<223> OTHER INFORMATION: mRNA destabilizing consensus sequence

<400> SEQUENCE: 29 tgtataata                                                            9

<210> SEQ ID NO 30
<211> LENGTH: 6
<212> TYPE: DNA
<213> ORGANISM: Artificial Sequence
<220> FEATURE:
<223> OTHER INFORMATION: the -10 element

<400> SEQUENCE: 30 tataat                                                               6

<210> SEQ ID NO 31
<211> LENGTH: 7
<212> TYPE: DNA
<213> ORGANISM: Artificial Sequence
<220> FEATURE:
<223> OTHER INFORMATION: the -35 element

<400> SEQUENCE: 31 ttgacat                                                              7

<210> SEQ ID NO 32
<211> LENGTH: 20
<212> TYPE: DNA
<213> ORGANISM: Artificial Sequence
<220> FEATURE:
<223> OTHER INFORMATION: UP element consensus sequence
<220> FEATURE:
<221> NAME/KEY: misc_feature
<222> LOCATION: (4)..(20)
<223> OTHER INFORMATION: W = A or T; N = any base

```
<400> SEQUENCE: 32
aaawwtwttt tnnnaaannn                                               20

<210> SEQ ID NO 33
<211> LENGTH: 6
<212> TYPE: DNA
<213> ORGANISM: Artificial Sequence
<220> FEATURE:
<223> OTHER INFORMATION: TATA box

<400> SEQUENCE: 33 tataaa                                                               6
```